(12) United States Patent
Michieli

(10) Patent No.: US 11,834,507 B2
(45) Date of Patent: Dec. 5, 2023

(54) ANTI-MET AGONIST ANTIBODY FOR USE IN THE TREATMENT OF COLORECTAL CANCER

(71) Applicant: AGOMAB THERAPEUTICS, Ghent (BE)

(72) Inventor: Paolo Michieli, Rivalta di Torino (IT)

(73) Assignee: Agomab Therapeutics, Ghent (BE)

( * ) Notice: Subject to any disclaimer, the term of this patent is extended or adjusted under 35 U.S.C. 154(b) by 29 days.

(21) Appl. No.: 16/959,713

(22) PCT Filed: Jan. 3, 2019

(86) PCT No.: PCT/EP2019/050077
§ 371 (c)(1),
(2) Date: Jul. 2, 2020

(87) PCT Pub. No.: WO2019/134927
PCT Pub. Date: Jul. 11, 2019

(65) Prior Publication Data
US 2021/0087281 A1 Mar. 25, 2021

(30) Foreign Application Priority Data
Jan. 3, 2018 (IT) .................. 102018000000535

(51) Int. Cl.
| A61K 39/395 | (2006.01) |
| C07K 16/28 | (2006.01) |
| A61P 35/00 | (2006.01) |
| A61K 39/00 | (2006.01) |

(52) U.S. Cl.
CPC .......... *C07K 16/2863* (2013.01); *A61P 35/00* (2018.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 5,686,292 | A | 11/1997 | Schwall et al. |
| 5,892,019 | A | 4/1999 | Schlom et al. |
| 6,099,841 | A | 8/2000 | Hillan et al. |
| 6,468,529 | B1 | 10/2002 | Schwall et al. |
| 7,476,724 | B2 | 1/2009 | Dennis et al. |
| 7,498,420 | B2 | 3/2009 | Bedian et al. |
| 7,556,804 | B2 | 7/2009 | Prat et al. |
| 8,163,280 | B2 | 4/2012 | Bedian et al. |
| 8,388,958 | B2 | 3/2013 | Comoglio et al. |
| 8,562,985 | B2 | 10/2013 | Bedian et al. |
| 8,729,043 | B2 | 5/2014 | Comoglio et al. |
| 8,821,869 | B2 | 9/2014 | Bedian et al. |
| 8,835,607 | B2 | 9/2014 | Dreier et al. |
| 9,150,613 | B2 | 10/2015 | Harding et al. |
| 9,169,329 | B2 | 10/2015 | Johns et al. |
| 9,394,367 | B2 | 7/2016 | Cheong et al. |
| 9,540,437 | B2 | 1/2017 | Dreier et al. |
| 10,106,622 | B2 | 10/2018 | Yoo et al. |
| 10,221,248 | B2 | 3/2019 | Halberg et al. |
| 11,098,126 | B2 | 8/2021 | Michieli |
| 2005/0054019 | A1 | 3/2005 | Bedian et al. |
| 2009/0285807 | A1 | 11/2009 | Comoglio et al. |
| 2010/0040629 | A1 | 2/2010 | Bedian et al. |
| 2011/0165621 | A1 | 7/2011 | Dreier et al. |
| 2012/0134996 | A1 | 5/2012 | Comoglio et al. |
| 2012/0321614 | A1 | 12/2012 | Bedian et al. |
| 2014/0086914 | A1 | 3/2014 | Bedian et al. |
| 2014/0193431 | A1 | 7/2014 | Park et al. |
| 2015/0057436 | A1 | 2/2015 | Dreier et al. |
| 2017/0145088 | A1 | 5/2017 | Dreier et al. |
| 2018/0002444 | A1 | 1/2018 | Halberg et al. |
| 2019/0241676 | A1 | 8/2019 | Halberg et al. |
| 2019/0315872 | A1 | 10/2019 | Yu et al. |
| 2019/0315873 | A1 | 10/2019 | Michieli |

FOREIGN PATENT DOCUMENTS

| AU | 2013201789 | 4/2013 |
| CN | 103998929 A | 8/2014 |
| WO | 9638557 A1 | 12/1996 |
| WO | 9800543 A1 | 1/1998 |
| WO | WO-02/088354 | 11/2002 |
| WO | 2004108766 A2 | 12/2004 |
| WO | 2005016382 A1 | 2/2005 |
| WO | 2007090807 A1 | 8/2007 |
| WO | WO-2010/001251 | 1/2010 |
| WO | 2011080350 A1 | 7/2011 |
| WO | 2011150454 A1 | 12/2011 |
| WO | 2012138599 A2 | 10/2012 |
| WO | 2016106221 A1 | 6/2016 |
| WO | 2017135791 A1 | 8/2017 |
| WO | 2018001909 A1 | 1/2018 |
| WO | 2019134932 A1 | 7/2019 |

OTHER PUBLICATIONS

Mizuno et al. (Int. J. Mol. Sci. 14: 888-919, 2013).*
Liu et al. (Clin. Cancer Res. 20(23): 6059-6070, 2014).*
Kim, Ki-Hyun, and Hyori Kim. "Progress of Antibody-Based Inhibitors of the HGF-CMET Axis in Cancer Therapy." Experimental Molecular Medicine, vol. 49, No. 3, Mar. 2017, p. e307. doi:10.1038/emm.2017.17.
Koliaraki, Vasiliki et al., Tpl2 regulates intestinal myofibroblast HGF release to suppress colitis-associated tumorigenesis, Oct. 15, 2012, J Clin Invest. 2012;122(11):4231-4242. https://doi.org/10.1172/JCI63917.

(Continued)

*Primary Examiner* — Christine J Saoud
(74) *Attorney, Agent, or Firm* — Patent Law Works LLP

(57) ABSTRACT

The present invention relates to treatment of cancer using agonist anti-MET antibodies or fragments thereof. In particular, the invention relates to treatment of colorectal cancer using agonist anti-MET antibodies or fragments, typically colorectal cancer associated with chronic inflammation and/or gene mutations in the colon and in the gastrointestinal tract in general. The invention further relates to treating intestinal fibrosis using agonist anti-MET antibodies.

14 Claims, 17 Drawing Sheets

Figure 1A:
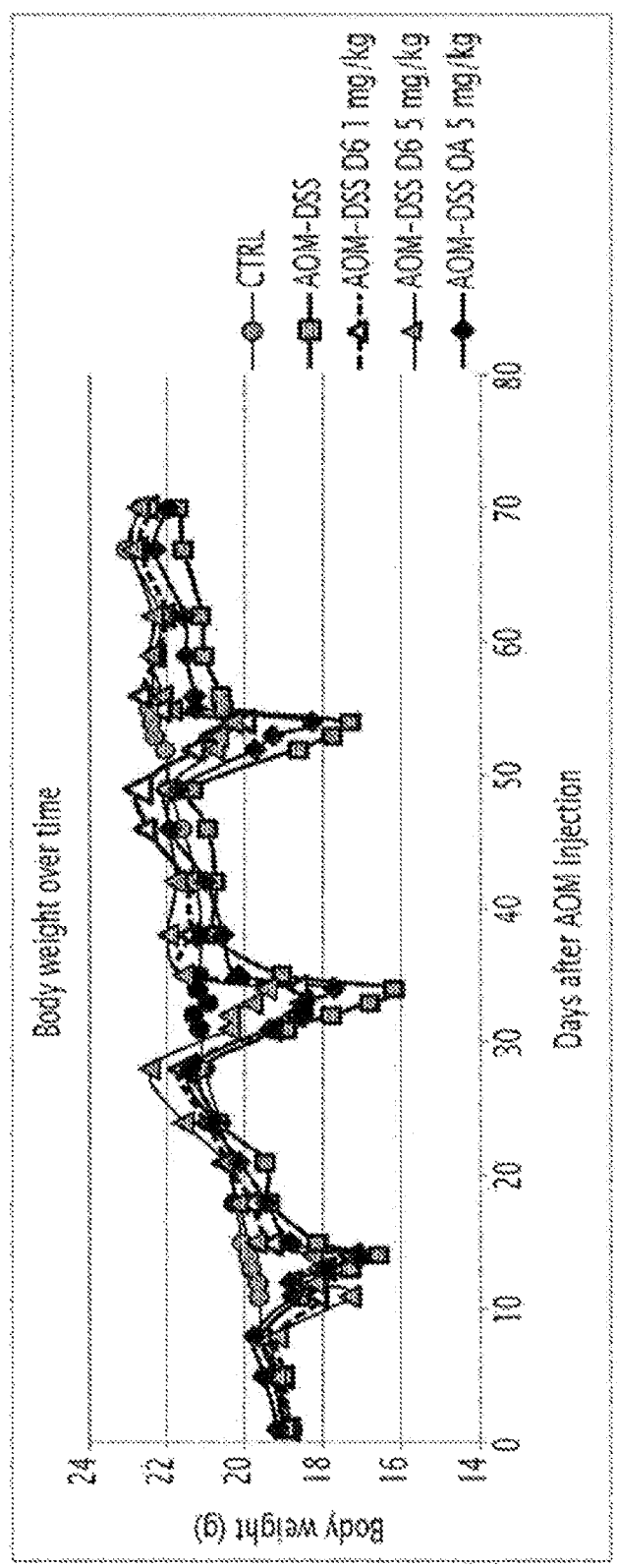

Specification includes a Sequence Listing.

(56) References Cited

OTHER PUBLICATIONS

Latella, Giovanni et al., Results of the 4th scientific workshop of the ECCO (I): Pathophysiology of intestinal fibrosis in IBD, Journal of Crohns and Colitis, vol. 8, Issue 10, Oct. 2014, pp. 1147-1165, https://doi.org/10.1016/j.crohns.2014.03.008.
Matsumoto, Kunio et al. "HGF-Met Pathway in Regeneration and Drug Discovery." Biomedicines., vol. 2, No. 4, Oct. 2014, pp. 275-300. EBSCOhost, doi:10.3390/biomedicines2040275.
Ohda, Y., et al. Effects of Hepatocyte Growth Factor on Rat Inflammatory Bowel Disease Models. Dig Dis Sci 50, 914-921 (2005). https://doi.org/10.1007/s10620-005-2664-z.
Owusu, Benjamin Yaw, et al. "Hepatocyte Growth Factor, a Key Tumor-Promoting Factor in the Tumor Microenvironment." Cancers, vol. 9, No. 4, Apr. 2017, p. 35. doi: 10.3390/cancers9040035.
PCT International Search Report and Written Opinion; Application No. PCT/EP2019/050077, Applicant AGOMAB Therapeutics BVBA, International filing date of Jan. 3, 2019, European Patent Office, dated Mar. 25, 2019, 13 pages.
Prat, Maria, et al. "Monoclonal Antibodies against the MET/HGF Receptor and Its Ligand: Multitask Tools with Applications from Basic Research to Therapy." Biomedicines, vol. 2, No. 4, Dec. 2014, pp. 359-383. doi:10.3390/biomedicines2040359.
"Seow H, Yip WK, Fifis T. ""Advances in targeted and immunobased therapies for colorectal cancer in the genomic era."" Onco Targets Therapy. 2016;9:1899-1920. https://doi.org/10.2147/OTT.S95101".
Van Der Horst, Edward Htun, et al. "Discovery of Fully Human Anti-MET Monoclonal Antibodies with Antitumor Activity against Colon Cancer Tumor Models In Vivo." Neoplasia, vol. 11, No. 4, Apr. 2009, p. 355. doi:10.1593/neo.81536.
Finkelshtein, A.V., et al. O.B. Ptitsyn, cf. Protein Physics: Series of lectures with colored stereoscopic illustrations and tasks: textbook, 4th edition revised and supplemented—Moscow: KDU (2012) p. 23. As cited on p. 2 of RU office action dated Sep. 30, 2020.
Russian Official Action Translation, Application No. 2018146419 Agomab Therapeutics BVBA, filing date Jun. 23, 2017, Russian Patent Office dated Sep. 30, 2020, 5 pgs.
Yarilin, A. A. "Principles of immunology." Moscow: Medicine (1999): 172-174. As cited on p. 2 of RU office action dated Sep. 30, 2020.
Pietronave, Stefano et al. "Agonist Monoclonal Antibodies against Hgf Receptor Protect Cardiac Muscle Cells from Apoptosis." American Journal of Physiology—Heart and Circulatory Physiology. 298.4 (2010).
Prat, Maria, et al. "Agonistic Monoclonal Antibodies against the Met Receptor Dissect the Biological Responses to Hgf." Journal of Cell Science. 111.2 (1998): 237-247.
Silvagno, Francesca et al. "In Vivo Activation of Met Tyrosine Kinase by Heterodimeric Hepatocyte Growth Factor Molecule Promotes Angiogenesis." Arteriosclerosis, Thrombosis, and Vascular Biology. 15.11 (1995): 1857-65.
Ohda, et al, "Effects of HepatocyteGrowth Factor on Rat Inflammatory Bowel Disease Models", (May 1, 2005), pp. 914-921, Digestive Diseases and Sciences., vol. 50, No. 5, XP055567387.
Latella, et al, "Results of the 4th scientific workshop of the ECCO (I): Pathophysiology of intestinal fibrosis in IBD", (Apr. 14, 2014), pp. 1147-1165, Journal of Crohn's and Colitis, Elsevier BV, NL, vol. 8, No. 10, XP029049187.
Matsumoto, et al, "HGF-Met Pathway in Regeneration and Drug Discovery", (Oct. 31, 2014), pp. 275-300, Biomedicines, vol. 2, No. 4, XP055412657.
Owusu, et al, "Hepatocyte Growth Factor, a Key Tumor-Promoting Factor in the Tumor Microenvironment", (Apr. 17, 2017), pp. 1-16, Cancers, vol. 9, No. 4, XP055568062.
Prat, et al, "Monoclonal Antibodies against the MET/HGF Receptor and Its Ligand: Multitask Tools with Applications from Basic Research to Therapy", (Mar. 12, 2014), pp. 359-383, Biomedicines, vol. 2, No. 4, XP055567764.

Kim, et al: "Progress of antibody-based inhibitors of the HGF-cMET axis in cancer therapy", (Mar. 1, 2017), pp. e307-e307, Experimental & Molecular Medicine, vol. 49, No. 3, XP055568049.
Seow, et al: "Advances in targeted and immunobased therapies for colorectal cancer in the genomic era.", (Mar. 31, 2016), pp. 1899-1920, Oncotargets and Therapy, vol. 9, XP055568076.
Htun Van Der Horst, et al, "Discovery of Fully Human Anti-MET Monoclonal Antibodies with Antitumor Activity against Colon Cancer Tumor Models In Vivo", (Apr. 1, 2009) pp. 355-INS, Neoplasia, vol. 11, No. 4, XP055565946.
Koliaraki,et al, "Tp12 regulates intestinal myofibroblast HGF release to suppress colitis-associated tumorigenesis", (Oct. 15, 2012) pp. 4231-4242, Journal of Clinical Investigation, vol. 122, No. 11, XP055566120.
Bardelli C et al: 11 Agonist Met antibodies define the signalling threshold required for a full mitogenic and invasive program of Kaposi's Sarcoma cells, Biochemical and Biophysical Research Communications, Elsevier, Amsterdam, NL, vol. 334, No. 4, Sep. 9, 2005 (Sep. 9, 2005), pp. 1172-1179, XP027459158, ISSN: 0006-291X, DOI: 10.1016/J.BBRC.2005.07.020 [retrieved on Jul. 29, 2005] the whole document.
Vargas Ga et al: "Hepatocyte Growth Factor in Renal Failure: Promise and Reality" , Kidney International, Nature Publishing Group, London, GB, vol. 57, No. 4, Apr. 1, 2000 (Apr. 1, 2000), pp. 1426-1436, XP001181170, ISSN: 0085-2538, DOI: 10.1046/J.1523-1755.2000.00987.X title.
J. Mellado-Gil et al: "Disruption of Hepatocyte Growth Factor/c-Met Signaling Enhances Pancreatic-Cell Death and Accelerates the Onset of Diabetes", Diabetes,vol. 60, No. 2, Oct. 27, 2010 (Oct. 27, 2010), pp. 525-536, XP055412664, us ISSN: 0012-1797, DOI: 10.2337/db09-1305 title.
Giovanni Pacchiana et al: "Monovalency Unleashes the Full Therapeutic Potential of the DN-30 Anti-Met Antibody", Journal of Biological Chemistry, American Society for Biochemistry and Molecular Biology, vol. 285, No. 46, Nov. 12, 2010 (Nov. 12, 2010), pp. 36149-36157, XP002621766, ISSN: 0021-9258, DOI: 10.1074/JBC.M110.134031 [retrieved on Sep. 10, 2010] the whole document.
International Search Report for PCT/EP2017/065599, dated Oct. 10, 2017.
Ohashi, et al, "Sustained survival of human hepatocytes in mice: A model for in vivo infection with human hepatitis B and hepatitis delta virus", Mar. 2000, pp. 327-331, vol. 6, No. 3, Nature Medicine.
Rudikoff, et al, "Single amino acid substitution altering antigen-binding specificity", Mar. 1982, pp. 1979-1983, vol. 79, Proc. Natl. Acad. Sci. USA.
Li, et al, "Anti-MET immunoPET for non-small cell lung cancer using novel fully human antibody fragments", Nov. 2014, pp. 2607-2617, vol. 13, No. 11, Mol Cancer Ther.
Ohno, et al, "Antigen-binding specificities of antibodies are primarily determined by sevel residues of $V_H$", May 1985, pp. 2945-2949, vol. 82, Proc. Natl. Acad. Sci. USA.
Diamond, et al, "Somatic mutation of the T15 heavy chain gives rise to an antibody with autoantibody specificity", Sep. 1984, pp. 5841-5844, vol. 81, Proc. Natl. Acad. Sci. USA.
Wei Zhou et al: "PAK1 mediates pancreatic cancer cell migration and resistance to MET inhibition : MET/PAKI signalling in pancreatic adenocarcinoma", The Journal of Pathology, vol. 234, No. 4, Oct. 6, 2014 (Oct. 6, 2014), pp. 502-513, XP055554664, ISSN: 0022-3417, DOI: 10.1002/path.4412 abstract.
Srinivasa P. Pothula et al: "Targeting the HGF/c-MET pathway: stromal remodelling in pancreatic cancer", Oncotarget, vol. 8, No. 44, Sep. 29, 2017 (Sep. 29, 2017), pp. 76722-76739, XP055554672, DOI: 10.18632/oncotarget.20822 abstract.
Jin Hongkui et al: "MetMAb, the one-armed 5D5 anti-c-Met antibody, inhibits orthotopic pancreatic tumor growth and improves survival", Cancer Research, AACR Annual Meeting 2017; Apr. 1-5, 2017; Washington, DC, US, vol. 68, No. 11, Jun. 1, 2008 (Jun. 1, 2008), pp. 4360-4368, XP002570057, ISSN: 0008-5472, DOI: 10.1158/0008-5472.CAN-07-5960 abstract.
Alexandre G. Oliveira et al: "The Role of Hepatocyte Growth Factor (HGF) in Insulin Resistance and Diabetes", Frontiers in

(56) References Cited

OTHER PUBLICATIONS

Endocrinology, vol. 9, Aug. 30, 2018 (Aug. 30, 2018), XP055554739, DOI: 10.3389/fendo.2018.00503 the whole document.

* cited by examiner

NUMBER OF TUMORS

MEAN TUMOR VOLUME

SEQUENCE LISTING

```
<160> NUMBER OF SEQ ID NOS: 210

<210> SEQ ID NO 1
<211> LENGTH: 30
<212> TYPE: PRT
<213> ORGANISM: Lama glama

<400> SEQUENCE: 1

Gln Leu Gln Leu Val Glu Ser Gly Gly Gly Leu Val Gln Pro Gly Gly
1               5                   10                  15

Ser Leu Arg Val Ser Cys Thr Ala Ser Gly Phe Thr Phe Asn
            20                  25                  30

<210> SEQ ID NO 2
<211> LENGTH: 5
<212> TYPE: PRT
<213> ORGANISM: Lama glama

<400> SEQUENCE: 2

Thr Tyr Tyr Met Thr
1               5

<210> SEQ ID NO 3
<211> LENGTH: 14
<212> TYPE: PRT
<213> ORGANISM: Lama glama

<400> SEQUENCE: 3

Trp Val Arg Gln Ala Pro Gly Lys Gly Leu Glu Trp Val Ser
1               5                   10

<210> SEQ ID NO 4
<211> LENGTH: 16
<212> TYPE: PRT
<213> ORGANISM: Lama glama

<400> SEQUENCE: 4

Asp Ile Asn Ser Gly Gly Gly Thr Tyr Tyr Ala Asp Ser Val Lys Gly
1               5                   10                  15

<210> SEQ ID NO 5
<211> LENGTH: 32
<212> TYPE: PRT
<213> ORGANISM: Lama glama

<400> SEQUENCE: 5
```

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Val Arg
            20                  25                  30

<210> SEQ ID NO 6
<211> LENGTH: 10
<212> TYPE: PRT
<213> ORGANISM: Lama glama

<400> SEQUENCE: 6

Val Arg Ile Trp Pro Val Gly Tyr Asp Tyr
1               5                   10

<210> SEQ ID NO 7
<211> LENGTH: 11
<212> TYPE: PRT
<213> ORGANISM: Lama glama

<400> SEQUENCE: 7

Trp Gly Gln Gly Thr Gln Val Thr Val Ser Ser
1               5                   10

<210> SEQ ID NO 8
<211> LENGTH: 30
<212> TYPE: PRT
<213> ORGANISM: Lama glama

<400> SEQUENCE: 8

Gln Val Gln Leu Val Glu Ser Gly Gly Gly Leu Val Gln Pro Gly Gly
1               5                   10                  15

Ser Leu Arg Val Ser Cys Ala Ala Ser Gly Phe Thr Phe Ser
            20                  25                  30

<210> SEQ ID NO 9
<211> LENGTH: 5
<212> TYPE: PRT
<213> ORGANISM: Lama glama

<400> SEQUENCE: 9

Thr Tyr Tyr Met Ser
1               5

<210> SEQ ID NO 10
<211> LENGTH: 14
<212> TYPE: PRT
<213> ORGANISM: Lama glama

<400> SEQUENCE: 10

Trp Val Arg Gln Ala Pro Gly Lys Gly Leu Glu Trp Val Ser
1               5                   10

<210> SEQ ID NO 11
<211> LENGTH: 16
<212> TYPE: PRT
<213> ORGANISM: Lama glama

<400> SEQUENCE: 11

Asp Ile Arg Thr Asp Gly Gly Thr Tyr Tyr Ala Asp Ser Val Lys Gly
1               5                   10                  15

<210> SEQ ID NO 12
<211> LENGTH: 32

```
<212> TYPE: PRT
<213> ORGANISM: Lama glama

<400> SEQUENCE: 12

Arg Phe Thr Met Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Arg
                20                  25                  30

<210> SEQ ID NO 13
<211> LENGTH: 10
<212> TYPE: PRT
<213> ORGANISM: Lama glama

<400> SEQUENCE: 13

Thr Arg Ile Phe Pro Ser Gly Tyr Asp Tyr
1               5                   10

<210> SEQ ID NO 14
<211> LENGTH: 11
<212> TYPE: PRT
<213> ORGANISM: Lama glama

<400> SEQUENCE: 14

Trp Gly Gln Gly Thr Gln Val Thr Val Ser Ser
1               5                   10

<210> SEQ ID NO 15
<211> LENGTH: 30
<212> TYPE: PRT
<213> ORGANISM: Lama glama

<400> SEQUENCE: 15

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 16
<211> LENGTH: 5
<212> TYPE: PRT
<213> ORGANISM: Lama glama

<400> SEQUENCE: 16

Ser His Ala Met Ser
1               5

<210> SEQ ID NO 17
<211> LENGTH: 14
<212> TYPE: PRT
<213> ORGANISM: Lama glama

<400> SEQUENCE: 17

Trp Val Arg Gln Ala Pro Gly Lys Gly Leu Glu Trp Val Ser
1               5                   10

<210> SEQ ID NO 18
<211> LENGTH: 17
<212> TYPE: PRT
<213> ORGANISM: Lama glama

<400> SEQUENCE: 18

Ala Ile Asn Ser Gly Gly Gly Ser Thr Ser Tyr Ala Asp Ser Val Lys
1               5                   10                  15
```

Gly

```
<210> SEQ ID NO 19
<211> LENGTH: 32
<212> TYPE: PRT
<213> ORGANISM: Lama glama

<400> SEQUENCE: 19
```

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

```
<210> SEQ ID NO 20
<211> LENGTH: 17
<212> TYPE: PRT
<213> ORGANISM: Lama glama

<400> SEQUENCE: 20
```

Glu Leu Arg Phe Asp Leu Ala Arg Tyr Thr Asp Tyr Glu Ala Trp Asp
1               5                   10                  15

Tyr

```
<210> SEQ ID NO 21
<211> LENGTH: 11
<212> TYPE: PRT
<213> ORGANISM: Lama glama

<400> SEQUENCE: 21
```

Trp Gly Gln Gly Thr Gln Val Thr Val Ser Ser
1               5                   10

```
<210> SEQ ID NO 22
<211> LENGTH: 30
<212> TYPE: PRT
<213> ORGANISM: Lama glama

<400> SEQUENCE: 22
```

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

```
<210> SEQ ID NO 23
<211> LENGTH: 5
<212> TYPE: PRT
<213> ORGANISM: Lama glama

<400> SEQUENCE: 23
```

Gly Tyr Gly Met Ser
1               5

```
<210> SEQ ID NO 24
<211> LENGTH: 14
<212> TYPE: PRT
<213> ORGANISM: Lama glama

<400> SEQUENCE: 24
```

Trp Val Arg Gln Ala Pro Gly Lys Gly Leu Glu Trp Val Ser
1               5                   10

```
<210> SEQ ID NO 25
```

```
<211> LENGTH: 17
<212> TYPE: PRT
<213> ORGANISM: Lama glama

<400> SEQUENCE: 25

Asp Ile Asn Ser Gly Gly Gly Ser Thr Ser Tyr Ala Asp Ser Val Lys
1               5                   10                  15
Gly

<210> SEQ ID NO 26
<211> LENGTH: 32
<212> TYPE: PRT
<213> ORGANISM: Lama glama

<400> SEQUENCE: 26

Arg Phe Thr Ile Ser Arg Asp Asn Ala Lys Asn Thr Leu Tyr Leu Gln
1               5                   10                  15
Met Asn Ser Leu Lys Pro Glu Asp Thr Ala Val Tyr Tyr Cys Ala Lys
            20                  25                  30

<210> SEQ ID NO 27
<211> LENGTH: 17
<212> TYPE: PRT
<213> ORGANISM: Lama glama

<400> SEQUENCE: 27

Asp Met Arg Leu Tyr Leu Ala Arg Tyr Asn Asp Tyr Glu Ala Trp Asp
1               5                   10                  15
Tyr

<210> SEQ ID NO 28
<211> LENGTH: 11
<212> TYPE: PRT
<213> ORGANISM: Lama glama

<400> SEQUENCE: 28

Trp Gly Gln Gly Thr Gln Val Thr Val Ser Ser
1               5                   10

<210> SEQ ID NO 29
<211> LENGTH: 30
<212> TYPE: PRT
<213> ORGANISM: Lama glama

<400> SEQUENCE: 29

Glu Leu Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser
            20                  25                  30

<210> SEQ ID NO 30
<211> LENGTH: 5
<212> TYPE: PRT
<213> ORGANISM: Lama glama

<400> SEQUENCE: 30

Ser Tyr Gly Met Ser
1               5

<210> SEQ ID NO 31
<211> LENGTH: 14
<212> TYPE: PRT
<213> ORGANISM: Lama glama
```

```
<400> SEQUENCE: 31

Trp Val Arg Gln Ala Pro Gly Lys Gly Leu Glu Trp Val Ser
1               5                   10

<210> SEQ ID NO 32
<211> LENGTH: 17
<212> TYPE: PRT
<213> ORGANISM: Lama glama

<400> SEQUENCE: 32

Ala Ile Asn Ser Tyr Gly Gly Ser Thr Ser Tyr Ala Asp Ser Val Lys
1               5                   10                  15

Gly

<210> SEQ ID NO 33
<211> LENGTH: 32
<212> TYPE: PRT
<213> ORGANISM: Lama glama

<400> SEQUENCE: 33

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
                20                  25                  30

<210> SEQ ID NO 34
<211> LENGTH: 17
<212> TYPE: PRT
<213> ORGANISM: Lama glama

<400> SEQUENCE: 34

Glu Val Arg Ala Asp Leu Ser Arg Tyr Asn Asp Tyr Glu Ser Tyr Asp
1               5                   10                  15

Tyr

<210> SEQ ID NO 35
<211> LENGTH: 11
<212> TYPE: PRT
<213> ORGANISM: Lama glama

<400> SEQUENCE: 35

Trp Gly Gln Gly Thr Gln Val Thr Val Ser Ser
1               5                   10

<210> SEQ ID NO 36
<211> LENGTH: 30
<212> TYPE: PRT
<213> ORGANISM: Lama glama

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Lys
                20                  25                  30

<210> SEQ ID NO 37
<211> LENGTH: 5
<212> TYPE: PRT
<213> ORGANISM: Lama glama

<400> SEQUENCE: 37
```

```
Asp Tyr Asp Ile Thr
1               5

<210> SEQ ID NO 38
<211> LENGTH: 14
<212> TYPE: PRT
<213> ORGANISM: Lama glama

<400> SEQUENCE: 38

Trp Val Arg Gln Ala Pro Gly Lys Gly Leu Glu Trp Val Ser
1               5                   10

<210> SEQ ID NO 39
<211> LENGTH: 17
<212> TYPE: PRT
<213> ORGANISM: Lama glama

<400> SEQUENCE: 39

Thr Ile Thr Ser Arg Ser Gly Ser Thr Ser Tyr Val Asp Ser Val Lys
1               5                   10                  15

Gly

<210> SEQ ID NO 40
<211> LENGTH: 32
<212> TYPE: PRT
<213> ORGANISM: Lama glama

<400> SEQUENCE: 40

Arg Phe Thr Ile Ser Gly Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 41
<211> LENGTH: 17
<212> TYPE: PRT
<213> ORGANISM: Lama glama

<400> SEQUENCE: 41

Val Tyr Ala Thr Thr Trp Asp Val Gly Pro Leu Gly Tyr Gly Met Asp
1               5                   10                  15

Tyr

<210> SEQ ID NO 42
<211> LENGTH: 11
<212> TYPE: PRT
<213> ORGANISM: Lama glama

<400> SEQUENCE: 42

Trp Gly Lys Gly Thr Leu Val Thr Val Ser Ser
1               5                   10

<210> SEQ ID NO 43
<211> LENGTH: 30
<212> TYPE: PRT
<213> ORGANISM: Lama glama

<400> SEQUENCE: 43

Glu Val Gln Leu Gln Glu Ser Gly Gly Gly Leu Val Gln Pro Gly Gly
1               5                   10                  15

Ser Leu Arg Leu Ser Cys Ala Ser Gly Phe Thr Phe Ser
            20                  25                  30
```

```
<210> SEQ ID NO 44
<211> LENGTH: 5
<212> TYPE: PRT
<213> ORGANISM: Lama glama

<400> SEQUENCE: 44

Ile Tyr Asp Met Ser
1               5

<210> SEQ ID NO 45
<211> LENGTH: 14
<212> TYPE: PRT
<213> ORGANISM: Lama glama

<400> SEQUENCE: 45

Trp Val Arg Gln Ala Pro Gly Lys Gly Leu Glu Trp Val Ser
1               5                   10

<210> SEQ ID NO 46
<211> LENGTH: 17
<212> TYPE: PRT
<213> ORGANISM: Lama glama

<400> SEQUENCE: 46

Thr Ile Asn Ser Asp Gly Ser Ser Thr Ser Tyr Val Asp Ser Val Lys
1               5                   10                  15

Gly

<210> SEQ ID NO 47
<211> LENGTH: 32
<212> TYPE: PRT
<213> ORGANISM: Lama glama

<400> SEQUENCE: 47

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Ala Lys
            20                  25                  30

<210> SEQ ID NO 48
<211> LENGTH: 17
<212> TYPE: PRT
<213> ORGANISM: Lama glama

<400> SEQUENCE: 48

Val Tyr Gly Ser Thr Trp Asp Val Gly Pro Met Gly Tyr Gly Met Asp
1               5                   10                  15

Tyr

<210> SEQ ID NO 49
<211> LENGTH: 11
<212> TYPE: PRT
<213> ORGANISM: Lama glama

<400> SEQUENCE: 49

Trp Gly Lys Gly Thr Leu Val Thr Val Ser Ser
1               5                   10

<210> SEQ ID NO 50
<211> LENGTH: 30
<212> TYPE: PRT
<213> ORGANISM: Lama glama
```

-continued

```
<400> SEQUENCE: 50

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 51
<211> LENGTH: 5
<212> TYPE: PRT
<213> ORGANISM: Lama glama

<400> SEQUENCE: 51

Asn Tyr Tyr Met Ser
1               5

<210> SEQ ID NO 52
<211> LENGTH: 14
<212> TYPE: PRT
<213> ORGANISM: Lama glama

<400> SEQUENCE: 52

Trp Val Arg Gln Ala Pro Gly Lys Gly Leu Glu Trp Val Ser
1               5                   10

<210> SEQ ID NO 53
<211> LENGTH: 17
<212> TYPE: PRT
<213> ORGANISM: Lama glama

<400> SEQUENCE: 53

Asp Ile Tyr Ser Asp Gly Ser Thr Thr Trp Tyr Ser Asp Ser Val Lys
1               5                   10                  15

Gly

<210> SEQ ID NO 54
<211> LENGTH: 32
<212> TYPE: PRT
<213> ORGANISM: Lama glama

<400> SEQUENCE: 54

Arg Phe Thr Ile Ser Arg Asp Asn Ala Lys Asn Thr Leu Ser Leu Gln
1               5                   10                  15

Met Asn Ser Leu Lys Ser Glu Asp Thr Ala Val Tyr Tyr Cys Ala Arg
            20                  25                  30

<210> SEQ ID NO 55
<211> LENGTH: 10
<212> TYPE: PRT
<213> ORGANISM: Lama glama

<400> SEQUENCE: 55

Val Lys Ile Tyr Pro Gly Gly Tyr Asp Ala
1               5                   10

<210> SEQ ID NO 56
<211> LENGTH: 11
<212> TYPE: PRT
<213> ORGANISM: Lama glama

<400> SEQUENCE: 56

Trp Gly Gln Gly Thr Gln Val Thr Val Ser Ser
1               5                   10
```

<210> SEQ ID NO 57
<211> LENGTH: 30
<212> TYPE: PRT
<213> ORGANISM: Lama glama

<400> SEQUENCE: 57

Gln Val Gln Leu Gln Glu Ser Gly Gly Asp Leu Val Gln Pro Gly Gly
1               5                   10                  15

Ser Leu Arg Val Ser Cys Val Val Ser Gly Phe Thr Phe Ser
            20                  25                  30

<210> SEQ ID NO 58
<211> LENGTH: 5
<212> TYPE: PRT
<213> ORGANISM: Lama glama

<400> SEQUENCE: 58

Arg Tyr Tyr Met Ser
1               5

<210> SEQ ID NO 59
<211> LENGTH: 14
<212> TYPE: PRT
<213> ORGANISM: Lama glama

<400> SEQUENCE: 59

Trp Val Arg Gln Ala Pro Gly Lys Gly Leu Glu Trp Val Ser
1               5                   10

<210> SEQ ID NO 60
<211> LENGTH: 17
<212> TYPE: PRT
<213> ORGANISM: Lama glama

<400> SEQUENCE: 60

Ser Ile Asp Ser Tyr Gly Tyr Ser Thr Tyr Tyr Thr Asp Ser Val Lys
1               5                   10                  15

Gly

<210> SEQ ID NO 61
<211> LENGTH: 32
<212> TYPE: PRT
<213> ORGANISM: Lama glama

<400> SEQUENCE: 61

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Arg
            20                  25                  30

<210> SEQ ID NO 62
<211> LENGTH: 9
<212> TYPE: PRT
<213> ORGANISM: Lama glama

<400> SEQUENCE: 62

Ala Lys Thr Thr Trp Ser Tyr Asp Tyr
1               5

<210> SEQ ID NO 63
<211> LENGTH: 11
<212> TYPE: PRT
<213> ORGANISM: Lama glama

```
<400> SEQUENCE: 63

Trp Gly Gln Gly Thr Gln Val Thr Val Ser Ser
1               5                   10

<210> SEQ ID NO 64
<211> LENGTH: 30
<212> TYPE: PRT
<213> ORGANISM: Lama glama

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg
            20                  25                  30

<210> SEQ ID NO 65
<211> LENGTH: 5
<212> TYPE: PRT
<213> ORGANISM: Lama glama

<400> SEQUENCE: 65

Asn Tyr His Met Ser
1               5

<210> SEQ ID NO 66
<211> LENGTH: 14
<212> TYPE: PRT
<213> ORGANISM: Lama glama

<400> SEQUENCE: 66

Trp Val Arg Gln Val Pro Gly Lys Gly Phe Glu Trp Ile Ser
1               5                   10

<210> SEQ ID NO 67
<211> LENGTH: 17
<212> TYPE: PRT
<213> ORGANISM: Lama glama

<400> SEQUENCE: 67

Asp Ile Asn Ser Ala Gly Gly Ser Thr Tyr Tyr Ala Asp Ser Val Lys
1               5                   10                  15

Gly

<210> SEQ ID NO 68
<211> LENGTH: 32
<212> TYPE: PRT
<213> ORGANISM: Lama glama

<400> SEQUENCE: 68

Arg Phe Thr Ile Ser Arg Asp Asn Ala Lys Asn Thr Leu Tyr Leu Glu
1               5                   10                  15

Met Asn Ser Leu Lys Pro Glu Asp Thr Ala Leu Tyr Tyr Cys Ala Arg
            20                  25                  30

<210> SEQ ID NO 69
<211> LENGTH: 8
<212> TYPE: PRT
<213> ORGANISM: Lama glama

<400> SEQUENCE: 69

Val Asn Val Trp Gly Val Asn Tyr
1               5
```

<210> SEQ ID NO 70
<211> LENGTH: 11
<212> TYPE: PRT
<213> ORGANISM: Lama glama

<400> SEQUENCE: 70

Trp Gly Lys Gly Thr Leu Val Ser Val Ser Ser
1               5                   10

<210> SEQ ID NO 71
<211> LENGTH: 30
<212> TYPE: PRT
<213> ORGANISM: Lama glama

<400> SEQUENCE: 71

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 72
<211> LENGTH: 5
<212> TYPE: PRT
<213> ORGANISM: Lama glama

<400> SEQUENCE: 72

Asn Tyr Val Met Ser
1               5

<210> SEQ ID NO 73
<211> LENGTH: 14
<212> TYPE: PRT
<213> ORGANISM: Lama glama

<400> SEQUENCE: 73

Trp Val Arg Gln Ala Pro Gly Lys Gly Leu Glu Trp Val Ser
1               5                   10

<210> SEQ ID NO 74
<211> LENGTH: 16
<212> TYPE: PRT
<213> ORGANISM: Lama glama

<400> SEQUENCE: 74

Asp Thr Asn Ser Gly Gly Ser Thr Ser Tyr Ala Asp Ser Val Lys Gly
1               5                   10                  15

<210> SEQ ID NO 75
<211> LENGTH: 32
<212> TYPE: PRT
<213> ORGANISM: Lama glama

<400> SEQUENCE: 75

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Leu Tyr Tyr Cys Ala Arg
            20                  25                  30

<210> SEQ ID NO 76
<211> LENGTH: 8
<212> TYPE: PRT
<213> ORGANISM: Lama glama

```
<400> SEQUENCE: 76

Ser Phe Phe Tyr Gly Met Asn Tyr
1               5

<210> SEQ ID NO 77
<211> LENGTH: 11
<212> TYPE: PRT
<213> ORGANISM: Lama glama

<400> SEQUENCE: 77

Trp Gly Lys Gly Thr Gln Val Thr Val Ser Ser
1               5                   10

<210> SEQ ID NO 78
<211> LENGTH: 22
<212> TYPE: PRT
<213> ORGANISM: Lama glama

<400> SEQUENCE: 78

Gln Ala Val Val Thr Gln Glu Pro Ser Leu Ser Val Ser Pro Gly Gly
1               5                   10                  15

Thr Val Thr Leu Thr Cys
            20

<210> SEQ ID NO 79
<211> LENGTH: 14
<212> TYPE: PRT
<213> ORGANISM: Lama glama

<400> SEQUENCE: 79

Gly Leu Ser Ser Gly Ser Val Thr Thr Ser Asn Tyr Pro Gly
1               5                   10

<210> SEQ ID NO 80
<211> LENGTH: 15
<212> TYPE: PRT
<213> ORGANISM: Lama glama

<400> SEQUENCE: 80

Trp Phe Gln Gln Thr Pro Gly Gln Ala Pro Arg Thr Leu Ile Tyr
1               5                   10                  15

<210> SEQ ID NO 81
<211> LENGTH: 7
<212> TYPE: PRT
<213> ORGANISM: Lama glama

<400> SEQUENCE: 81

Asn Thr Asn Asn Arg His Ser
1               5

<210> SEQ ID NO 82
<211> LENGTH: 32
<212> TYPE: PRT
<213> ORGANISM: Lama glama

<400> SEQUENCE: 82

Gly Val Pro Ser Arg Phe Ser Gly Ser Ile Ser Gly Asn Lys Ala Ala
1               5                   10                  15

Leu Thr Ile Thr Gly Ala Gln Pro Glu Asp Glu Ala Asp Tyr Tyr Cys
            20                  25                  30

<210> SEQ ID NO 83
```

```
<211> LENGTH: 10
<212> TYPE: PRT
<213> ORGANISM: Lama glama

<400> SEQUENCE: 83

Ser Leu Tyr Thr Gly Ser Tyr Thr Thr Val
1               5                   10

<210> SEQ ID NO 84
<211> LENGTH: 10
<212> TYPE: PRT
<213> ORGANISM: Lama glama

<400> SEQUENCE: 84

Phe Gly Gly Gly Thr His Leu Thr Val Leu
1               5                   10

<210> SEQ ID NO 85
<211> LENGTH: 22
<212> TYPE: PRT
<213> ORGANISM: Lama glama

<400> SEQUENCE: 85

Gln Ala Val Val Thr Gln Glu Pro Ser Leu Ser Val Ser Pro Gly Gly
1               5                   10                  15

Thr Val Thr Leu Thr Cys
            20

<210> SEQ ID NO 86
<211> LENGTH: 14
<212> TYPE: PRT
<213> ORGANISM: Lama glama

<400> SEQUENCE: 86

Gly Leu Ser Ser Gly Ser Val Thr Thr Ser Asn Tyr Pro Gly
1               5                   10

<210> SEQ ID NO 87
<211> LENGTH: 15
<212> TYPE: PRT
<213> ORGANISM: Lama glama

<400> SEQUENCE: 87

Trp Phe Gln Gln Thr Pro Gly Gln Ala Pro Arg Thr Leu Ile Tyr
1               5                   10                  15

<210> SEQ ID NO 88
<211> LENGTH: 7
<212> TYPE: PRT
<213> ORGANISM: Lama glama

<400> SEQUENCE: 88

Asn Thr Asn Ser Arg His Ser
1               5

<210> SEQ ID NO 89
<211> LENGTH: 32
<212> TYPE: PRT
<213> ORGANISM: Lama glama

<400> SEQUENCE: 89

Gly Val Pro Ser Arg Phe Ser Gly Ser Ile Ser Gly Asn Lys Ala Ala
1               5                   10                  15

Leu Thr Ile Met Gly Ala Gln Pro Glu Asp Glu Ala Asp Tyr Tyr Cys
```

<210> SEQ ID NO 90
<211> LENGTH: 9
<212> TYPE: PRT
<213> ORGANISM: Lama glama

<400> SEQUENCE: 90

Ser Leu Tyr Pro Gly Ser Thr Thr Val
1               5

<210> SEQ ID NO 91
<211> LENGTH: 10
<212> TYPE: PRT
<213> ORGANISM: Lama glama

<400> SEQUENCE: 91

Phe Gly Gly Gly Thr His Leu Thr Val Leu
1               5                   10

<210> SEQ ID NO 92
<211> LENGTH: 22
<212> TYPE: PRT
<213> ORGANISM: Lama glama

<400> SEQUENCE: 92

Ser Tyr Glu Leu Thr Gln Pro Ser Ala Leu Ser Val Thr Leu Gly Gln
1               5                   10                  15

Thr Ala Lys Ile Thr Cys
            20

<210> SEQ ID NO 93
<211> LENGTH: 11
<212> TYPE: PRT
<213> ORGANISM: Lama glama

<400> SEQUENCE: 93

Gln Gly Gly Ser Leu Gly Ser Ser Tyr Ala His
1               5                   10

<210> SEQ ID NO 94
<211> LENGTH: 15
<212> TYPE: PRT
<213> ORGANISM: Lama glama

<400> SEQUENCE: 94

Trp Tyr Gln Gln Lys Pro Gly Gln Ala Pro Val Leu Val Ile Tyr
1               5                   10                  15

<210> SEQ ID NO 95
<211> LENGTH: 7
<212> TYPE: PRT
<213> ORGANISM: Lama glama

<400> SEQUENCE: 95

Asp Asp Asp Ser Arg Pro Ser
1               5

<210> SEQ ID NO 96
<211> LENGTH: 32
<212> TYPE: PRT
<213> ORGANISM: Lama glama

<400> SEQUENCE: 96

Gly Ile Pro Glu Arg Phe Ser Gly Ser Ser Ser Gly Thr Ala Thr
1               5                   10                  15

Leu Thr Ile Ser Gly Ala Gln Ala Glu Asp Glu Gly Asp Tyr Tyr Cys
            20                  25                  30

<210> SEQ ID NO 97
<211> LENGTH: 11
<212> TYPE: PRT
<213> ORGANISM: Lama glama

<400> SEQUENCE: 97

Gln Ser Ala Asp Ser Ser Gly Asn Ala Ala Val
1               5                   10

<210> SEQ ID NO 98
<211> LENGTH: 10
<212> TYPE: PRT
<213> ORGANISM: Lama glama

<400> SEQUENCE: 98

Phe Gly Gly Gly Thr His Leu Thr Val Leu
1               5                   10

<210> SEQ ID NO 99
<211> LENGTH: 22
<212> TYPE: PRT
<213> ORGANISM: Lama glama

<400> SEQUENCE: 99

Ser Ser Ala Leu Thr Gln Pro Ser Ala Leu Ser Val Thr Leu Gly Gln
1               5                   10                  15

Thr Ala Lys Ile Thr Cys
            20

<210> SEQ ID NO 100
<211> LENGTH: 11
<212> TYPE: PRT
<213> ORGANISM: Lama glama

<400> SEQUENCE: 100

Gln Gly Gly Ser Leu Gly Ser Ser Tyr Ala His
1               5                   10

<210> SEQ ID NO 101
<211> LENGTH: 15
<212> TYPE: PRT
<213> ORGANISM: Lama glama

<400> SEQUENCE: 101

Trp Tyr Gln Gln Lys Pro Gly Gln Ala Pro Val Leu Val Ile Tyr
1               5                   10                  15

<210> SEQ ID NO 102
<211> LENGTH: 7
<212> TYPE: PRT
<213> ORGANISM: Lama glama

<400> SEQUENCE: 102

Asp Asp Asp Ser Arg Pro Ser
1               5

<210> SEQ ID NO 103
<211> LENGTH: 32
<212> TYPE: PRT

<213> ORGANISM: Lama glama

<400> SEQUENCE: 103

Gly Ile Pro Glu Arg Phe Ser Gly Ser Ser Ser Gly Thr Ala Thr
1               5                   10                  15

Leu Thr Ile Ser Gly Ala Gln Ala Glu Asp Glu Gly Asp Tyr Tyr Cys
            20                  25                  30

<210> SEQ ID NO 104
<211> LENGTH: 11
<212> TYPE: PRT
<213> ORGANISM: Lama glama

<400> SEQUENCE: 104

Gln Ser Ala Asp Ser Ser Gly Asn Ala Ala Val
1               5                   10

<210> SEQ ID NO 105
<211> LENGTH: 10
<212> TYPE: PRT
<213> ORGANISM: Lama glama

<400> SEQUENCE: 105

Phe Gly Gly Gly Thr His Leu Thr Val Leu
1               5                   10

<210> SEQ ID NO 106
<211> LENGTH: 22
<212> TYPE: PRT
<213> ORGANISM: Lama glama

<400> SEQUENCE: 106

Gln Pro Val Leu Asn Gln Pro Ser Ala Leu Ser Val Thr Leu Gly Gln
1               5                   10                  15

Thr Ala Lys Ile Thr Cys
            20

<210> SEQ ID NO 107
<211> LENGTH: 11
<212> TYPE: PRT
<213> ORGANISM: Lama glama

<400> SEQUENCE: 107

Gln Gly Gly Ser Leu Gly Ala Arg Tyr Ala His
1               5                   10

<210> SEQ ID NO 108
<211> LENGTH: 15
<212> TYPE: PRT
<213> ORGANISM: Lama glama

<400> SEQUENCE: 108

Trp Tyr Gln Gln Lys Pro Gly Gln Ala Pro Val Leu Val Ile Tyr
1               5                   10                  15

<210> SEQ ID NO 109
<211> LENGTH: 7
<212> TYPE: PRT
<213> ORGANISM: Lama glama

<400> SEQUENCE: 109

Asp Asp Asp Ser Arg Pro Ser
1               5

```
<210> SEQ ID NO 110
<211> LENGTH: 32
<212> TYPE: PRT
<213> ORGANISM: Lama glama

<400> SEQUENCE: 110

Gly Ile Pro Glu Arg Phe Ser Gly Ser Ser Ser Gly Thr Ala Thr
1               5                   10                  15

Leu Thr Ile Ser Gly Ala Gln Ala Glu Asp Glu Gly Asp Tyr Tyr Cys
            20                  25                  30

<210> SEQ ID NO 111
<211> LENGTH: 9
<212> TYPE: PRT
<213> ORGANISM: Lama glama

<400> SEQUENCE: 111

Gln Ser Ala Asp Ser Ser Gly Ser Val
1               5

<210> SEQ ID NO 112
<211> LENGTH: 10
<212> TYPE: PRT
<213> ORGANISM: Lama glama

<400> SEQUENCE: 112

Phe Gly Gly Gly Thr His Leu Thr Val Leu
1               5                   10

<210> SEQ ID NO 113
<211> LENGTH: 22
<212> TYPE: PRT
<213> ORGANISM: Lama glama

<400> SEQUENCE: 113

Ser Tyr Glu Leu Thr Gln Pro Ser Ala Leu Ser Val Thr Leu Gly Gln
1               5                   10                  15

Thr Ala Lys Ile Thr Cys
            20

<210> SEQ ID NO 114
<211> LENGTH: 11
<212> TYPE: PRT
<213> ORGANISM: Lama glama

<400> SEQUENCE: 114

Gln Gly Gly Ser Leu Gly Ser Ser Tyr Ala His
1               5                   10

<210> SEQ ID NO 115
<211> LENGTH: 15
<212> TYPE: PRT
<213> ORGANISM: Lama glama

<400> SEQUENCE: 115

Trp Tyr Gln Gln Lys Pro Gly Gln Ala Pro Val Leu Val Ile Tyr
1               5                   10                  15

<210> SEQ ID NO 116
<211> LENGTH: 7
<212> TYPE: PRT
<213> ORGANISM: Lama glama

<400> SEQUENCE: 116
```

```
Asp Asp Asp Ser Arg Pro Ser
1               5
```

```
<210> SEQ ID NO 117
<211> LENGTH: 32
<212> TYPE: PRT
<213> ORGANISM: Lama glama

<400> SEQUENCE: 117

Gly Ile Pro Glu Arg Phe Ser Gly Ser Ser Ser Gly Thr Ala Thr
1               5                   10                  15

Leu Thr Ile Ser Gly Ala Gln Ala Glu Asp Glu Gly Asp Tyr Tyr Cys
            20                  25                  30
```

```
<210> SEQ ID NO 118
<211> LENGTH: 11
<212> TYPE: PRT
<213> ORGANISM: Lama glama

<400> SEQUENCE: 118

Gln Ser Ala Asp Ser Ser Gly Asn Ala Ala Val
1               5                   10
```

```
<210> SEQ ID NO 119
<211> LENGTH: 10
<212> TYPE: PRT
<213> ORGANISM: Lama glama

<400> SEQUENCE: 119

Phe Gly Gly Gly Thr His Leu Thr Val Leu
1               5                   10
```

```
<210> SEQ ID NO 120
<211> LENGTH: 22
<212> TYPE: PRT
<213> ORGANISM: Lama glama

<400> SEQUENCE: 120

Ser Ser Ala Leu Thr Gln Pro Ser Ala Leu Ser Val Ser Leu Gly Gln
1               5                   10                  15

Thr Ala Arg Ile Thr Cys
            20
```

```
<210> SEQ ID NO 121
<211> LENGTH: 11
<212> TYPE: PRT
<213> ORGANISM: Lama glama

<400> SEQUENCE: 121

Gln Gly Gly Ser Leu Gly Ser Ser Tyr Ala His
1               5                   10
```

```
<210> SEQ ID NO 122
<211> LENGTH: 15
<212> TYPE: PRT
<213> ORGANISM: Lama glama

<400> SEQUENCE: 122

Trp Tyr Gln Gln Lys Pro Gly Gln Ala Pro Val Leu Val Ile Tyr
1               5                   10                  15
```

```
<210> SEQ ID NO 123
<211> LENGTH: 7
```

<212> TYPE: PRT
<213> ORGANISM: Lama glama

<400> SEQUENCE: 123

Gly Asp Asp Ser Arg Pro Ser
1               5

<210> SEQ ID NO 124
<211> LENGTH: 32
<212> TYPE: PRT
<213> ORGANISM: Lama glama

<400> SEQUENCE: 124

Gly Ile Pro Glu Arg Phe Ser Gly Ser Ser Ser Gly Thr Ala Thr
1               5                   10                  15

Leu Thr Ile Ser Gly Ala Gln Ala Glu Asp Glu Asp Tyr Tyr Cys
            20                  25                  30

<210> SEQ ID NO 125
<211> LENGTH: 10
<212> TYPE: PRT
<213> ORGANISM: Lama glama

<400> SEQUENCE: 125

Gln Ser Thr Asp Ser Ser Gly Asn Thr Val
1               5                   10

<210> SEQ ID NO 126
<211> LENGTH: 10
<212> TYPE: PRT
<213> ORGANISM: Lama glama

<400> SEQUENCE: 126

Phe Gly Gly Gly Thr Arg Leu Thr Val Leu
1               5                   10

<210> SEQ ID NO 127
<211> LENGTH: 22
<212> TYPE: PRT
<213> ORGANISM: Lama glama

<400> SEQUENCE: 127

Gln Ala Gly Leu Thr Gln Pro Pro Ser Val Ser Gly Ser Pro Gly Lys
1               5                   10                  15

Thr Val Thr Ile Ser Cys
            20

<210> SEQ ID NO 128
<211> LENGTH: 14
<212> TYPE: PRT
<213> ORGANISM: Lama glama

<400> SEQUENCE: 128

Ala Gly Asn Ser Ser Asp Val Gly Tyr Gly Asn Tyr Val Ser
1               5                   10

<210> SEQ ID NO 129
<211> LENGTH: 15
<212> TYPE: PRT
<213> ORGANISM: Lama glama

<400> SEQUENCE: 129

Trp Tyr Gln Gln Phe Pro Gly Met Ala Pro Lys Leu Leu Ile Tyr
1               5                   10                  15

<210> SEQ ID NO 130
<211> LENGTH: 7
<212> TYPE: PRT
<213> ORGANISM: Lama glama

<400> SEQUENCE: 130

Leu Val Asn Lys Arg Ala Ser
1               5

<210> SEQ ID NO 131
<211> LENGTH: 32
<212> TYPE: PRT
<213> ORGANISM: Lama glama

<400> SEQUENCE: 131

Gly Ile Thr Asp Arg Phe Ser Gly Ser Lys Ser Gly Asn Thr Ala Ser
1               5                   10                  15

Leu Thr Ile Ser Gly Leu Gln Ser Glu Asp Glu Ala Asp Tyr Tyr Cys
            20                  25                  30

<210> SEQ ID NO 132
<211> LENGTH: 10
<212> TYPE: PRT
<213> ORGANISM: Lama glama

<400> SEQUENCE: 132

Ala Ser Tyr Thr Gly Ser Asn Asn Ile Val
1               5                   10

<210> SEQ ID NO 133
<211> LENGTH: 10
<212> TYPE: PRT
<213> ORGANISM: Lama glama

<400> SEQUENCE: 133

Phe Gly Gly Gly Thr His Leu Thr Val Leu
1               5                   10

<210> SEQ ID NO 134
<211> LENGTH: 23
<212> TYPE: PRT
<213> ORGANISM: Lama glama

<400> SEQUENCE: 134

Glu Ile Val Leu Thr Gln Ser Pro Ser Val Thr Ala Ser Val Gly
1               5                   10                  15

Gly Lys Val Thr Ile Asn Cys
            20

<210> SEQ ID NO 135
<211> LENGTH: 17
<212> TYPE: PRT
<213> ORGANISM: Lama glama

<400> SEQUENCE: 135

Lys Ser Ser Gln Ser Val Phe Ile Ala Ser Asn Gln Lys Thr Tyr Leu
1               5                   10                  15

Asn

<210> SEQ ID NO 136
<211> LENGTH: 15
<212> TYPE: PRT

<213> ORGANISM: Lama glama

<400> SEQUENCE: 136

Trp Tyr Gln Gln Arg Pro Gly Gln Ser Pro Arg Leu Val Ile Ser
1               5                   10                  15

<210> SEQ ID NO 137
<211> LENGTH: 7
<212> TYPE: PRT
<213> ORGANISM: Lama glama

<400> SEQUENCE: 137

Tyr Ala Ser Thr Arg Glu Ser
1               5

<210> SEQ ID NO 138
<211> LENGTH: 32
<212> TYPE: PRT
<213> ORGANISM: Lama glama

<400> SEQUENCE: 138

Gly Ile Pro Asp Arg Phe Ser Gly Ser Gly Ser Thr Thr Asp Phe Thr
1               5                   10                  15

Leu Thr Ile Ser Ser Val Gln Pro Glu Asp Ala Ala Val Tyr Tyr Cys
                20                  25                  30

<210> SEQ ID NO 139
<211> LENGTH: 8
<212> TYPE: PRT
<213> ORGANISM: Lama glama

<400> SEQUENCE: 139

Gln Gln Ala Tyr Ser His Pro Thr
1               5

<210> SEQ ID NO 140
<211> LENGTH: 10
<212> TYPE: PRT
<213> ORGANISM: Lama glama

<400> SEQUENCE: 140

Phe Gly Gln Gly Thr Lys Val Glu Leu Lys
1               5                   10

<210> SEQ ID NO 141
<211> LENGTH: 22
<212> TYPE: PRT
<213> ORGANISM: Lama glama

<400> SEQUENCE: 141

Gln Thr Val Val Thr Gln Glu Pro Ser Leu Ser Val Ser Pro Gly Gly
1               5                   10                  15

Thr Val Thr Leu Thr Cys
                20

<210> SEQ ID NO 142
<211> LENGTH: 14
<212> TYPE: PRT
<213> ORGANISM: Lama glama

<400> SEQUENCE: 142

Gly Leu Ser Ser Gly Ser Val Thr Thr Ser Asn Tyr Pro Gly
1               5                   10

<210> SEQ ID NO 143
<211> LENGTH: 15
<212> TYPE: PRT
<213> ORGANISM: Lama glama

<400> SEQUENCE: 143

Trp Phe Gln Gln Thr Pro Gly Gln Ala Pro Arg Thr Leu Ile Tyr
1               5                   10                  15

<210> SEQ ID NO 144
<211> LENGTH: 7
<212> TYPE: PRT
<213> ORGANISM: Lama glama

<400> SEQUENCE: 144

Asn Thr Asn Ser Arg His Ser
1               5

<210> SEQ ID NO 145
<211> LENGTH: 32
<212> TYPE: PRT
<213> ORGANISM: Lama glama

<400> SEQUENCE: 145

Gly Val Pro Ser Arg Phe Ser Gly Ser Ile Ser Gly Asn Lys Ala Ala
1               5                   10                  15
Leu Thr Ile Thr Gly Ala Gln Pro Glu Asp Glu Ala Asp Tyr Tyr Cys
            20                  25                  30

<210> SEQ ID NO 146
<211> LENGTH: 10
<212> TYPE: PRT
<213> ORGANISM: Lama glama

<400> SEQUENCE: 146

Ser Leu Tyr Pro Gly Ser Tyr Thr Asn Val
1               5                   10

<210> SEQ ID NO 147
<211> LENGTH: 10
<212> TYPE: PRT
<213> ORGANISM: Lama glama

<400> SEQUENCE: 147

Phe Gly Gly Gly Thr His Leu Thr Val Leu
1               5                   10

<210> SEQ ID NO 148
<211> LENGTH: 22
<212> TYPE: PRT
<213> ORGANISM: Lama glama

<400> SEQUENCE: 148

Gln Ser Ala Leu Thr Gln Pro Pro Ser Leu Ser Ala Ser Pro Gly Ser
1               5                   10                  15
Ser Val Arg Leu Thr Cys
            20

<210> SEQ ID NO 149
<211> LENGTH: 14
<212> TYPE: PRT
<213> ORGANISM: Lama glama

<400> SEQUENCE: 149

-continued

```
Thr Leu Ser Ser Gly Asn Asn Ile Gly Ser Tyr Asp Ile Ser
1               5                   10
```

<210> SEQ ID NO 150
<211> LENGTH: 15
<212> TYPE: PRT
<213> ORGANISM: Lama glama

<400> SEQUENCE: 150

```
Trp Tyr Gln Gln Lys Ala Gly Ser Pro Pro Arg Tyr Leu Leu Asn
1               5                   10                  15
```

<210> SEQ ID NO 151
<211> LENGTH: 11
<212> TYPE: PRT
<213> ORGANISM: Lama glama

<400> SEQUENCE: 151

```
Tyr Tyr Thr Asp Ser Arg Lys His Gln Asp Ser
1               5                   10
```

<210> SEQ ID NO 152
<211> LENGTH: 34
<212> TYPE: PRT
<213> ORGANISM: Lama glama

<400> SEQUENCE: 152

```
Gly Val Pro Ser Arg Phe Ser Gly Ser Lys Asp Ala Ser Ala Asn Ala
1               5                   10                  15
Gly Leu Leu Leu Ile Ser Gly Leu Gln Pro Glu Asp Glu Ala Asp Tyr
            20                  25                  30
Tyr Cys
```

<210> SEQ ID NO 153
<211> LENGTH: 11
<212> TYPE: PRT
<213> ORGANISM: Lama glama

<400> SEQUENCE: 153

```
Ser Ala Tyr Lys Ser Gly Ser Tyr Arg Trp Val
1               5                   10
```

<210> SEQ ID NO 154
<211> LENGTH: 10
<212> TYPE: PRT
<213> ORGANISM: Lama glama

<400> SEQUENCE: 154

```
Phe Gly Gly Gly Thr His Val Thr Val Leu
1               5                   10
```

<210> SEQ ID NO 155
<211> LENGTH: 118
<212> TYPE: PRT
<213> ORGANISM: Lama glama

<400> SEQUENCE: 155

```
Gln Leu Gln Leu Val Glu Ser Gly Gly Gly Leu Val Gln Pro Gly Gly
1               5                   10                  15
Ser Leu Arg Val Ser Cys Thr Ala Ser Gly Phe Thr Phe Asn Thr Tyr
            20                  25                  30
Tyr Met Thr Trp Val Arg Gln Ala Pro Gly Lys Gly Leu Glu Trp Val
```

```
                35                  40                  45
Ser Asp Ile Asn Ser Gly Gly Gly Thr Tyr Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Leu Tyr Tyr Cys Val
                 85                  90                  95

Arg Val Arg Ile Trp Pro Val Gly Tyr Asp Tyr Trp Gly Gln Gly Thr
                100                 105                 110

Gln Val Thr Val Ser Ser
                115

<210> SEQ ID NO 156
<211> LENGTH: 110
<212> TYPE: PRT
<213> ORGANISM: Lama glama

<400> SEQUENCE: 156

Gln Ala Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Thr Ser
                20                  25                  30

Asn Tyr Pro Gly Trp Phe Gln Gln Thr Pro Gly Gln Ala Pro Arg Thr
                35                  40                  45

Leu Ile Tyr Asn Thr Asn Asn Arg His Ser Gly Val Pro Ser Arg Phe
 50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ser Leu Tyr Thr Gly Ser
                 85                  90                  95

Tyr Thr Thr Val Phe Gly Gly Gly Thr His Leu Thr Val Leu
                100                 105                 110

<210> SEQ ID NO 157
<211> LENGTH: 118
<212> TYPE: PRT
<213> ORGANISM: Lama glama

<400> SEQUENCE: 157

Gln Val Gln Leu Val Glu Ser Gly Gly Gly Leu Val Gln Pro Gly Gly
 1               5                  10                  15

Ser Leu Arg Val Ser Cys Ala Ala Ser Gly Phe Thr Phe Ser Thr Tyr
                20                  25                  30

Tyr Met Ser Trp Val Arg Gln Ala Pro Gly Lys Gly Leu Glu Trp Val
                35                  40                  45

Ser Asp Ile Arg Thr Asp Gly Gly Thr Tyr Tyr Ala Asp Ser Val Lys
 50                  55                  60

Gly Arg Phe Thr Met Ser Arg Asp Asn Ala Lys Asn Thr Leu Tyr Leu
 65                  70                  75                  80

Gln Met Asn Ser Leu Lys Pro Glu Asp Thr Ala Leu Tyr Tyr Cys Ala
                 85                  90                  95

Arg Thr Arg Ile Phe Pro Ser Gly Tyr Asp Tyr Trp Gly Gln Gly Thr
                100                 105                 110

Gln Val Thr Val Ser Ser
                115
```

```
<210> SEQ ID NO 158
<211> LENGTH: 109
<212> TYPE: PRT
<213> ORGANISM: Lama glama

<400> SEQUENCE: 158

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Met Gly Ala
65                  70                  75                  80

Gln Pro Glu Asp Glu Ala Asp Tyr Tyr Cys Ser Leu Tyr Pro Gly Ser
                85                  90                  95

Thr Thr Val Phe Gly Gly Gly Thr His Leu Thr Val Leu
            100                 105

<210> SEQ ID NO 159
<211> LENGTH: 126
<212> TYPE: PRT
<213> ORGANISM: Lama glama

<400> SEQUENCE: 159

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Leu Arg Phe Asp Leu Ala Arg Tyr Thr Asp Tyr Glu Ala
            100                 105                 110

Trp Asp Tyr Trp Gly Gln Gly Thr Gln Val Thr Val Ser Ser
        115                 120                 125

<210> SEQ ID NO 160
<211> LENGTH: 108
<212> TYPE: PRT
<213> ORGANISM: Lama glama

<400> SEQUENCE: 160

Ser Tyr Glu Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60
```

```
Ser Ser Gly Gly Thr Ala Thr Leu Thr Ile Ser Gly Ala Gln Ala Glu
 65                  70                  75                  80

Asp Glu Gly Asp Tyr Tyr Cys Gln Ser Ala Asp Ser Ser Gly Asn Ala
                 85                  90                  95

Ala Val Phe Gly Gly Gly Thr His Leu Thr Val Leu
            100                 105
```

<210> SEQ ID NO 161
<211> LENGTH: 126
<212> TYPE: PRT
<213> ORGANISM: Lama glama

<400> SEQUENCE: 161

```
Glu Leu Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Gly Tyr
                20                  25                  30

Gly Met Ser Trp Val Arg Gln Ala Pro Gly Lys Gly Leu Glu Trp Val
            35                  40                  45

Ser Asp Ile Asn Ser Gly Gly Gly Ser Thr Ser Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Lys Asp Met Arg Leu Tyr Leu Ala Arg Tyr Asn Asp Tyr Glu Ala
            100                 105                 110

Trp Asp Tyr Trp Gly Gln Gly Thr Gln Val Thr Val Ser Ser
        115                 120                 125
```

<210> SEQ ID NO 162
<211> LENGTH: 108
<212> TYPE: PRT
<213> ORGANISM: Lama glama

<400> SEQUENCE: 162

```
Ser Ser Ala Leu Thr Gln Pro Ser Ala Leu Ser Val Thr Leu Gly Gln
 1               5                   10                  15

Thr Ala Lys Ile Thr Cys Gln Gly Gly Ser Leu Gly Ser Ser Tyr Ala
                20                  25                  30

His Trp Tyr Gln Gln Lys Pro Gly Gln Ala Pro Val Leu Val Ile Tyr
            35                  40                  45

Asp Asp Asp Ser Arg Pro Ser Gly Ile Pro Glu Arg Phe Ser Gly Ser
 50                  55                  60

Ser Ser Gly Gly Thr Ala Thr Leu Thr Ile Ser Gly Ala Gln Ala Glu
 65                  70                  75                  80

Asp Glu Gly Asp Tyr Tyr Cys Gln Ser Ala Asp Ser Ser Gly Asn Ala
                 85                  90                  95

Ala Val Phe Gly Gly Gly Thr His Leu Thr Val Leu
            100                 105
```

<210> SEQ ID NO 163
<211> LENGTH: 126
<212> TYPE: PRT
<213> ORGANISM: Lama glama

<400> SEQUENCE: 163

-continued

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Ala Ile Asn Ser Tyr Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Glu Val Arg Ala Asp Leu Ser Arg Tyr Asn Asp Tyr Glu Ser
            100                 105                 110

Tyr Asp Tyr Trp Gly Gln Gly Thr Gln Val Thr Val Ser Ser
            115                 120                 125

<210> SEQ ID NO 164
<211> LENGTH: 106
<212> TYPE: PRT
<213> ORGANISM: Lama glama

<400> SEQUENCE: 164

Gln Pro Val Leu Asn Gln Pro Ser Ala Leu Ser Val Thr Leu Gly Gln
1               5                   10                  15

Thr Ala Lys Ile Thr Cys Gln Gly Gly Ser Leu Gly Ala Arg Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Ser Val
                85                  90                  95

Phe Gly Gly Gly Thr His Leu Thr Val Leu
            100                 105

<210> SEQ ID NO 165
<211> LENGTH: 126
<212> TYPE: PRT
<213> ORGANISM: Lama glama

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Lys Asp Tyr
            20                  25                  30

Asp Ile Thr Trp Val Arg Gln Ala Pro Gly Lys Gly Leu Glu Trp Val
        35                  40                  45

Ser Thr Ile Thr Ser Arg Ser Gly Ser Thr Ser Tyr Val Asp Ser Val
    50                  55                  60

Lys Gly Arg Phe Thr Ile Ser Gly Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

```
Ala Lys Val Tyr Ala Thr Thr Trp Asp Val Gly Pro Leu Gly Tyr Gly
            100                 105                 110

Met Asp Tyr Trp Gly Lys Gly Thr Leu Val Thr Val Ser Ser
        115                 120                 125

<210> SEQ ID NO 166
<211> LENGTH: 108
<212> TYPE: PRT
<213> ORGANISM: Lama glama

<400> SEQUENCE: 166

Ser Tyr Glu Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
            20                  25                  30

His Trp Tyr Gln Gln Lys Pro Gly Gln Ala Pro Val Leu Val Ile Tyr
        35                  40                  45

Asp Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

Ala Val Phe Gly Gly Gly Thr His Leu Thr Val Leu
            100                 105

<210> SEQ ID NO 167
<211> LENGTH: 126
<212> TYPE: PRT
<213> ORGANISM: Lama glama

<400> SEQUENCE: 167

Glu Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met Ser Trp Val Arg Gln Ala Pro Gly Lys Gly Leu Glu Trp Val
        35                  40                  45

Ser Thr Ile Asn Ser Asp Gly Ser Ser Thr Ser Tyr Val Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Val Tyr Gly Ser Thr Trp Asp Val Gly Pro Met Gly Tyr Gly
            100                 105                 110

Met Asp Tyr Trp Gly Lys Gly Thr Leu Val Thr Val Ser Ser
        115                 120                 125

<210> SEQ ID NO 168
<211> LENGTH: 107
<212> TYPE: PRT
<213> ORGANISM: Lama glama

<400> SEQUENCE: 168

Ser Ser Ala Leu Thr Gln Pro Ser Ala Leu Ser Val Ser Leu Gly Gln
1               5                   10                  15

Thr Ala Arg Ile Thr Cys Gln Gly Gly Ser Leu Gly Ser Ser Tyr Ala
```

```
            20                  25                  30

His Trp Tyr Gln Gln Lys Pro Gly Gln Ala Pro Val Leu Val Ile Tyr
        35                  40                  45

Gly Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Asp Asp Tyr Tyr Cys Gln Ser Thr Asp Ser Ser Gly Asn Thr
                85                  90                  95

Val Phe Gly Gly Gly Thr Arg Leu Thr Val Leu
            100                 105

<210> SEQ ID NO 169
<211> LENGTH: 119
<212> TYPE: PRT
<213> ORGANISM: Lama glama

<400> SEQUENCE: 169

Gln Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Ser Trp Val Arg Gln Ala Pro Gly Lys Gly Leu Glu Trp Val
        35                  40                  45

Ser Asp Ile Tyr Ser Asp Gly Ser Thr Thr Trp Tyr Ser Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Ser Glu Asp Thr Ala Val Tyr Tyr Cys
                85                  90                  95

Ala Arg Val Lys Ile Tyr Pro Gly Gly Tyr Asp Ala Trp Gly Gln Gly
            100                 105                 110

Thr Gln Val Thr Val Ser Ser
        115

<210> SEQ ID NO 170
<211> LENGTH: 110
<212> TYPE: PRT
<213> ORGANISM: Lama glama

<400> SEQUENCE: 170

Gln Ala Gly Leu Thr Gln Pro Pro Ser Val Ser Gly Ser Pro Gly Lys
1               5                   10                  15

Thr Val Thr Ile Ser Cys Ala Gly Asn Ser Ser Asp Val Gly Tyr Gly
            20                  25                  30

Asn Tyr Val Ser Trp Tyr Gln Gln Phe Pro Gly Met Ala Pro Lys Leu
        35                  40                  45

Leu Ile Tyr Leu Val Asn Lys Arg Ala Ser Gly Ile Thr Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Thr Gly Ser
                85                  90                  95

Asn Asn Ile Val Phe Gly Gly Gly Thr His Leu Thr Val Leu
            100                 105                 110
```

-continued

<210> SEQ ID NO 171
<211> LENGTH: 118
<212> TYPE: PRT
<213> ORGANISM: Lama glama

<400> SEQUENCE: 171

Gln Val Gln Leu Gln Glu Ser Gly Gly Asp Leu Val Gln Pro Gly Gly
1               5                   10                  15

Ser Leu Arg Val Ser Cys Val Val Ser Gly Phe Thr Phe Ser Arg Tyr
            20                  25                  30

Tyr Met Ser Trp Val Arg Gln Ala Pro Gly Lys Gly Leu Glu Trp Val
        35                  40                  45

Ser Ser Ile Asp Ser Tyr Gly Tyr Ser Thr Tyr Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg Ala Lys Thr Thr Trp Ser Tyr Asp Tyr Trp Gly Gln Gly Thr
            100                 105                 110

Gln Val Thr Val Ser Ser
        115

<210> SEQ ID NO 172
<211> LENGTH: 112
<212> TYPE: PRT
<213> ORGANISM: Lama glama

<400> SEQUENCE: 172

Glu Ile Val Leu Thr Gln Ser Pro Ser Ser Val Thr Ala Ser Val Gly
1               5                   10                  15

Gly Lys Val Thr Ile Asn Cys Lys Ser Ser Gln Ser Val Phe Ile Ala
            20                  25                  30

Ser Asn Gln Lys Thr Tyr Leu Asn Trp Tyr Gln Gln Arg Pro Gly Gln
        35                  40                  45

Ser Pro Arg Leu Val Ile Ser Tyr Ala Ser Thr Arg Glu Ser Gly Ile
    50                  55                  60

Pro Asp Arg Phe Ser Gly Ser Gly Ser Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser His Pro Thr Phe Gly Gln Gly Thr Lys Val Glu Leu Lys
            100                 105                 110

<210> SEQ ID NO 173
<211> LENGTH: 117
<212> TYPE: PRT
<213> ORGANISM: Lama glama

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

His Met Ser Trp Val Arg Gln Val Pro Gly Lys Gly Phe Glu Trp Ile
        35                  40                  45

Ser Asp Ile Asn Ser Ala Gly Gly Ser Thr Tyr Tyr Ala Asp Ser Val
    50                  55                  60

```
Lys Gly Arg Phe Thr Ile Ser Arg Asp Asn Ala Lys Asn Thr Leu Tyr
 65                  70                  75                  80

Leu Glu Met Asn Ser Leu Lys Pro Glu Asp Thr Ala Leu Tyr Tyr Cys
                 85                  90                  95

Ala Arg Val Asn Val Trp Gly Val Asn Tyr Trp Gly Lys Gly Thr Leu
            100                 105                 110

Val Ser Val Ser Ser
            115

<210> SEQ ID NO 174
<211> LENGTH: 110
<212> TYPE: PRT
<213> ORGANISM: Lama glama

<400> SEQUENCE: 174

Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Thr Ser
             20                  25                  30

Asn Tyr Pro Gly Trp Phe Gln Gln Thr Pro Gly Gln Ala Pro Arg Thr
             35                  40                  45

Leu Ile Tyr Asn Thr Asn Ser Arg His Ser Gly Val Pro Ser Arg Phe
 50                  55                  60

Ser Gly Ser Ile Ser Gly Asn Lys Ala Ala Leu Thr Ile Thr Gly Ala
 65                  70                  75                  80

Gln Pro Glu Asp Glu Ala Asp Tyr Tyr Cys Ser Leu Tyr Pro Gly Ser
                 85                  90                  95

Tyr Thr Asn Val Phe Gly Gly Gly Thr His Leu Thr Val Leu
            100                 105                 110

<210> SEQ ID NO 175
<211> LENGTH: 116
<212> TYPE: PRT
<213> ORGANISM: Lama glama

<400> SEQUENCE: 175

Glu Leu Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Val Met Ser Trp Val Arg Gln Ala Pro Gly Lys Gly Leu Glu Trp Val
             35                  40                  45

Ser Asp Thr Asn Ser Gly Gly Ser Thr Ser Tyr Ala Asp Ser Val Lys
 50                  55                  60

Gly Arg Phe Thr Ile Ser Arg Asp Asn Ala Lys Asn Thr Leu Tyr Leu
 65                  70                  75                  80

Gln Met Asn Ser Leu Lys Pro Glu Asp Thr Ala Leu Tyr Tyr Cys Ala
                 85                  90                  95

Arg Ser Phe Phe Tyr Gly Met Asn Tyr Trp Gly Lys Gly Thr Gln Val
            100                 105                 110

Thr Val Ser Ser
        115

<210> SEQ ID NO 176
<211> LENGTH: 117
<212> TYPE: PRT
<213> ORGANISM: Lama glama
```

<400> SEQUENCE: 176

```
Gln Ser Ala Leu Thr Gln Pro Pro Ser Leu Ser Ala Ser Pro Gly Ser
1               5                   10                  15

Ser Val Arg Leu Thr Cys Thr Leu Ser Ser Gly Asn Asn Ile Gly Ser
            20                  25                  30

Tyr Asp Ile Ser Trp Tyr Gln Gln Lys Ala Gly Ser Pro Pro Arg Tyr
        35                  40                  45

Leu Leu Asn Tyr Tyr Thr Asp Ser Arg Lys His Gln Asp Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ser Ala Tyr Lys Ser Gly Ser Tyr Arg Trp Val Phe Gly Gly Gly Thr
            100                 105                 110

His Val Thr Val Leu
        115
```

<210> SEQ ID NO 177
<211> LENGTH: 354
<212> TYPE: DNA
<213> ORGANISM: Lama glama

<400> SEQUENCE: 177

```
cagttgcagc tggtggagtc tgggggaggc ttggtgcagc ctggggggtc tctgagagtt    60
tcctgtacag cctctggatt caccttcaat acctactaca tgacctgggt ccgccaggct   120
ccagggaagg ggctcgagtg gtctcgagat attaatagtg gtggtggtac atactatgca   180
gactccgtga agggccgatt caccatctcc agagacaacg ccaagaacac gctatatctg   240
caaatgaaca gcctgaaacc tgaggacacg gccctgtatt actgtgtaag agttcgtatt   300
tggccagtgg gatatgacta ctggggccag gggacccagg tcaccgtttc ctca         354
```

<210> SEQ ID NO 178
<211> LENGTH: 330
<212> TYPE: DNA
<213> ORGANISM: Lama glama

<400> SEQUENCE: 178

```
caggctgtgg tgacccagga gccgtccctg tcagtgtctc caggagggac ggtcacactc    60
acctgcggcc tcagctctgg gtctgtcact accagtaact ccctggttg gttccagcag   120
acaccgggcc aggctccacg cactcttatc tacaacacaa acaaccgcca ctctggggtc   180
cccagtcgct tctccggatc catctctggg aacaaagccg ccctcaccat cacgggggcc   240
cagcccgagg acgaggccga ctattactgt tctctatata ctggcagtta cactactgtg   300
ttcggcggag ggaccatctt gaccgtcctg                                   330
```

<210> SEQ ID NO 179
<211> LENGTH: 354
<212> TYPE: DNA
<213> ORGANISM: Lama glama

<400> SEQUENCE: 179

```
caggtgcagc tggtggagtc tgggggaggc ttggtgcagc ctggggggtc tctgagagtc    60
tcctgtgcag cctctggatt caccttcagt acctactaca tgagctgggt ccgccaggct   120
```

```
ccagggaagg ggctcgagtg ggtctcagat attcgtactg atggtggcac atactatgca    180
gactccgtga agggccgatt caccatgtcc agagacaacg ccaagaacac gctgtatcta    240
caaatgaaca gcctgaaacc tgaggacacg gccctgtatt actgtgcaag aactcgaatt    300
ttcccctcgg ggtatgacta ctggggccag gggacccagg tcaccgtctc ctca          354
```

<210> SEQ ID NO 180
<211> LENGTH: 327
<212> TYPE: DNA
<213> ORGANISM: Lama glama

<400> SEQUENCE: 180

```
caggctgtgg tgacccagga gccgtccctg tcagtgtctc caggagggac ggtcacactc    60
acctgcggcc tcagctctgg gtctgtcact accagtaact ccctggttg gttccagcag    120 acaccaggcc aggctccgcg cactcttatc tacaacacaa acagccgcca ctctggggtc    180
cccagtcgct tctccggatc catctctggg aacaaagccg ccctcaccat catggggcc    240 cagcccgagg acgaggccga ctattactgt tctctgtacc tggtagtac cactgtgttc    300 ggcggaggga cccatctgac cgtcctg                                         327
```

<210> SEQ ID NO 181
<211> LENGTH: 378
<212> TYPE: DNA
<213> ORGANISM: Lama glama

<400> SEQUENCE: 181

```
cagttgcagc tggtggagtc tgggggaggc ttggtgcagc ctggggggtc tctgagactc    60
tcctgtgcag cctctggatt caccttcagt agccatgcca tgagctgggt ccgccaggct    120
ccaggaaagg ggctcgagtg gtctcagct attaatagtg gtggtggtag cacaagctat    180
gcagactccg tgaagggccg attcaccatc tccagagaca cgccaagaa cacgctgtac    240 ctgcaaatga acagcctgaa acctgaggac acggccgtgt attactgtgc aaaagagctg    300
agattcgacc tagcaaggta taccgactat gaggcctggg actactgggg ccaggggacc    360
caggtcaccg tctcctca                                                   378
```

<210> SEQ ID NO 182
<211> LENGTH: 324
<212> TYPE: DNA
<213> ORGANISM: Lama glama

<400> SEQUENCE: 182

```
tcctatgagc tgactcagcc ctccgcgctg tccgtaacct gggacagac ggccaagatc    60 acctgccaag gtggcagctt aggtagcagt tatgctcact ggtaccagca gaagccaggc    120
caggcccctg tgctggtcat ctatgatgat gacagcaggc cctcagggat ccctgagcgg    180
ttctctggct ccagctctgg ggcacagcc accctgacca tcagcggggc ccaggccgag    240
gacgagggtg actattactg tcagtcagca gacagcagtg taatgctgc tgtgttcggc    300 ggagggaccc atctgaccgt cctg                                            324
```

<210> SEQ ID NO 183
<211> LENGTH: 378
<212> TYPE: DNA
<213> ORGANISM: Lama glama

<400> SEQUENCE: 183

```
gagttgcagc tggtggagtc tgggggaggc ttggtgcagc ctggggggtc tctgagactc    60
```

```
tcctgtgcag cctctggatt caccttcagt ggctatggca tgagctgggt ccgccaggct    120
ccaggaaagg ggctcgagtg ggtctcagat attaatagtg gtggtggtag cacaagctat    180
gcagactccg tgaagggccg attcaccatc tccagagaca acgccaagaa cacgctgtat    240
ctgcaaatga acagcctgaa acctgaggac acggccgtgt attactgtgc aaaagatatg    300
agattatacc tagcaaggta taacgactat gaggcctggg actactgggg ccaggggacc    360
caggtcaccg tctcctca                                                  378
```

<210> SEQ ID NO 184
<211> LENGTH: 324
<212> TYPE: DNA
<213> ORGANISM: Lama glama

<400> SEQUENCE: 184

```
tcctctgcac tgactcagcc ctccgcgctg tccgtaacct gggacagac ggccaagatc     60 acctgccaag gtggcagctt aggtagcagt tatgctcact ggtaccagca gaagccaggc    120
caggcccctg tgctggtcat ctatgatgat gacagcaggc cctcagggat ccctgagcgg    180
ttctctggct ccagctctgg ggcacagcc accctgacca tcagcggggc ccaggccgag    240
gacgagggtg actattactg tcagtcagca gacagcagtg gtaatgctgc tgtgttcggc    300
ggagggaccc atctgaccgt cctg                                           324
```

<210> SEQ ID NO 185
<211> LENGTH: 378
<212> TYPE: DNA
<213> ORGANISM: Lama glama

<400> SEQUENCE: 185

```
gagttgcagc tggtggagtc tgggggaggc ttggtgcagc ctggggggtc tctgagactc     60
tcctgtgcag cctctggatt caccttcagt agctatggca tgagctgggt ccgccaggct    120
ccaggaaagg ggctcgagtg ggtctcagct attaatagtt atggtggtag cacaagctat    180
gcagactccg tgaagggccg attcaccatc tccagagaca acgccaagaa cacgctgtat    240
ctgcaaatga acagcctgaa acctgaggac acggccgtgt attactgtgc aaaagaagtg    300
cgggccgacc taagccgcta taacgactat gagtcgtatg actactgggg ccaggggacc    360
caggtcaccg tctcctca                                                  378
```

<210> SEQ ID NO 186
<211> LENGTH: 318
<212> TYPE: DNA
<213> ORGANISM: Lama glama

<400> SEQUENCE: 186

```
cagccggtgc tgaatcagcc ctccgcgctg tccgtaacct gggacagac ggccaagatc     60 acctgccaag gtggcagctt aggtgcgcgt tatgctcact ggtaccagca gaagccaggc    120
caggcccctg tgctggtcat ctatgatgat gacagcaggc cctcagggat ccctgagcgg    180
ttctctggct ccagctctgg ggcacagcc accctgacca tcagcggggc ccaggccgag    240
gacgagggtg actattactg tcagtcagca gacagcagtg gttctgtgtt cggcggaggg    300
acccatctga ccgtcctg                                                  318
```

<210> SEQ ID NO 187
<211> LENGTH: 378
<212> TYPE: DNA

<213> ORGANISM: Lama glama

<400> SEQUENCE: 187

| | | | | | |
|---|---|---|---|---|---|
| gaggtgcagc | tcgtggagtc | tgggggaggc | ttggtgcagc | ctggggggtc | tctgagactc | 60 |
| tcctgtgcag | cctctggatt | cagcttcaag | gactatgaca | taacctgggt | ccgccaggct | 120 |
| ccgggaaagg | ggctcgagtg | ggtctcaact | attactagtc | gtagtggtag | cacaagctat | 180 |
| gtagactccg | taaagggccg | attcaccatc | tccggagaca | acgccaagaa | cacgctgtat | 240 |
| ctgcaaatga | acagcctgaa | acctgaggac | acggccgtgt | attactgtgc | aaaagtttac | 300 |
| gcgactacct | gggacgtcgg | ccctctgggc | tacggcatgg | actactgggg | caaggggacc | 360 |
| ctggtcaccg | tctcctca | | | | | 378 |

<210> SEQ ID NO 188
<211> LENGTH: 324
<212> TYPE: DNA
<213> ORGANISM: Lama glama

<400> SEQUENCE: 188

| | | | | | |
|---|---|---|---|---|---|
| tcctatgagc | tgactcagcc | ctccgcgctg | tccgtaacct | tgggacagac | ggccaagatc | 60 |
| acctgccaag | gtggcagctt | aggtagcagt | tatgctcact | ggtaccagca | gaagccaggc | 120 |
| caggcccctg | tgctggtcat | ctatgatgat | gacagcaggc | cctcagggat | ccctgagcgg | 180 |
| ttctctggct | ccagctctgg | ggcacagcc | accctgacca | tcagcggggc | ccaggccgag | 240 |
| gacgagggtg | actattactg | tcagtcagca | gacagcagtg | gtaatgctgc | tgtgttcggc | 300 |
| ggagggaccc | atctgaccgt | cctg | | | | 324 |

<210> SEQ ID NO 189
<211> LENGTH: 378
<212> TYPE: DNA
<213> ORGANISM: Lama glama

<400> SEQUENCE: 189

| | | | | | |
|---|---|---|---|---|---|
| gaggtgcagc | tgcaggagtc | gggggaggc | ttggtgcagc | ctggggggtc | tctgagactc | 60 |
| tcctgtgcag | cctctggatt | caccttcagt | atatatgaca | tgagctgggt | ccgccaggct | 120 |
| ccaggaaagg | ggctcgagtg | ggtctcaact | attaatagtg | atggtagtag | cacaagctat | 180 |
| gtagactccg | tgaagggccg | attcaccatc | tccagagaca | acgccaagaa | cacgctgtat | 240 |
| ctgcaaatga | acagcctgaa | acctgaggac | acggccgtgt | attactgtgc | gaaagtttac | 300 |
| ggtagtacct | gggacgtcgg | ccctatgggc | tacggcatgg | actactgggg | caaagggacc | 360 |
| ctggtcactg | tctcctca | | | | | 378 |

<210> SEQ ID NO 190
<211> LENGTH: 321
<212> TYPE: DNA
<213> ORGANISM: Lama glama

<400> SEQUENCE: 190

| | | | | | |
|---|---|---|---|---|---|
| tcctctgcac | tgactcagcc | ctccgcgctg | tccgtgtcct | tgggacagac | ggccaggatc | 60 |
| acctgccaag | gtggcagctt | aggtagcagt | tatgctcact | ggtaccagca | gaagccaggc | 120 |
| caggcccctg | tgctggtcat | ctatggtgat | gacagcaggc | cctcagggat | ccctgagcgg | 180 |
| ttctctggct | ccagctctgg | ggcacagcc | accctgacca | tcagcggggc | ccaggccgag | 240 |
| gacgaggatg | actattactg | tcagtcaaca | gacagcagtg | gtaatactgt | gttcggcgga | 300 |
| gggacccgac | tgaccgtcct | g | | | | 321 |

<210> SEQ ID NO 191
<211> LENGTH: 357
<212> TYPE: DNA
<213> ORGANISM: Lama glama

<400> SEQUENCE: 191

```
caggtgcagc tggtggagtc tgggggaaac ttggtgcagc ctgggggttc tctgagactc      60
tcctgtgcag cctctggatt caccttcagt aactactaca tgagctgggt ccgccaggct     120
ccagggaagg ggctggaatg ggtgtccgat atttatagtg acggtagtac cacatggtat     180
tcagactccg tcaagggccg attcaccatc tccagagaca cgccaagaa cacgctgtct      240
ctgcaaatga acagtctgaa atctgaggac acggccgtct attactgtgc gcgcgtgaag     300
atctatccgg ggggtatga cgcctggggc caggggaccc aggtcaccgt ctcctca         357
```

<210> SEQ ID NO 192
<211> LENGTH: 330
<212> TYPE: DNA
<213> ORGANISM: Lama glama

<400> SEQUENCE: 192

```
caggcagggc tgactcagcc tccctccgtg tctgggtctc caggaaagac ggtcaccatc      60
tcctgtgcag gaaacagcag tgatgttggg tatggaaact atgtctcctg gtaccagcag     120
ttcccaggaa tggccccaa actcctgata tatctcgtca ataaacgggc ctcagggatc       180
actgatcgct ctctggctc caagtcaggc aacacggcct ccctgaccat ctctgggctc      240
cagtctgagg acgaggctga ttattactgt gcctcatata caggtagcaa caatatcgtg     300
ttcggcggag ggacccatct aaccgtcctc                                      330
```

<210> SEQ ID NO 193
<211> LENGTH: 354
<212> TYPE: DNA
<213> ORGANISM: Lama glama

<400> SEQUENCE: 193

```
caggtgcagc tgcaggagtc gggggaagac ttggtgcagc ctggggggtc tctgagagtc      60
tcctgtgtag tctctggatt caccttcagt cgctactaca tgagctgggt ccgccaggct     120
ccagggaagg ggctcgagtg gtctcatct attgatagtt atggttacag cacatactat      180
acagactccg tgaagggccg attcaccatc tccagagaca cgccaagaa cacgctgtat      240
ctgcaaatga acagcctgaa acctgaggac acggccctgt attactgtgc aagagcgaaa    300
acgacttgga gttatgacta ctggggccag gggacccagg tcaccgtctc ctca           354
```

<210> SEQ ID NO 194
<211> LENGTH: 336
<212> TYPE: DNA
<213> ORGANISM: Lama glama

<400> SEQUENCE: 194

```
gaaattgtgt tgacgcagtc tcccagctcc gtgactgcat ctgtaggagg gaaggtcact      60
atcaactgta agtccagcca gagcgtcttc atagcttcta tcagaaaaac ctacttaaac     120
tggtaccagc agagacctgg acagtctccg aggttggtca tcagctatgc gtccacccgt     180
gaatcgggga tccctgatcg attcagcggc agtgggtcca acagatttt cactctcacg      240
atcagcagtg tccagcctga agatgcggcc gtgtattact gtcagcaggc ttatagccat    300
```

```
ccaacgttcg gccaggggac caaggtggaa ctcaaa                              336
```

<210> SEQ ID NO 195
<211> LENGTH: 351
<212> TYPE: DNA
<213> ORGANISM: Lama glama

<400> SEQUENCE: 195

```
gaggtgcagc tcgtggagtc tgggggaggc ttggtgcaac ctgggggttc tctgagactc    60
tcctgtgcag cctctggatt caccttcagg aattaccaca tgagttgggt ccgccaggtt   120
ccagggaagg ggttcgagtg gatctcagat attaatagtg caggtggtag cacatactat   180
gcagactccg tgaagggccg attcaccatc tccagagaca acgccaagaa cacgctgtat   240
ctggaaatga acagcctgaa acctgaggac acggccctgt attactgtgc aagagtcaac   300
gtctgggggg tgaactactg gggcaaaggg accctggtca gcgtctcctc a            351
```

<210> SEQ ID NO 196
<211> LENGTH: 330
<212> TYPE: DNA
<213> ORGANISM: Lama glama

<400> SEQUENCE: 196

```
cagactgtgg tgactcagga gccgtccctg tcagtgtctc caggagggac ggtcacactc    60
acctgcggcc tcagctctgg gtctgtcact accagtaact accctggttg gttccagcag   120
acaccaggcc aggctccacg cactcttatc tacaacacaa acagccgcca ctctggggtc   180
cccagtcgct ctccggatc catctctggg aacaaagccg ccctcaccat cacggggggcc   240
cagcccgagg acgaggccga ctattactgt tctctgtacc tggtagtta cactaatgtg   300
ttcggcggag ggacccatct gaccgtcctg                                    330
```

<210> SEQ ID NO 197
<211> LENGTH: 348
<212> TYPE: DNA
<213> ORGANISM: Lama glama

<400> SEQUENCE: 197

```
gagttgcagc tggtggagtc tgggggaggc ttggtgcagc ctgggggggtc tctgagactc    60
tcctgtgcag cctctggatt caccttcagc aactatgtca tgagctgggt ccgccaggct   120
ccaggaaagg ggctcgagtg ggtctcagat actaatagtg gtggtagcac aagctatgca   180
gactccgtga agggccgatt caccatctct agagacaacg ccaagaacac gctgtatttg   240
caaatgaaca gcctgaaacc tgaggacacg gcattgtatt actgtgcgag atcatttttc   300
tacggcatga actactgggg caaagggacc caggtcaccg tgtcctca               348
```

<210> SEQ ID NO 198
<211> LENGTH: 351
<212> TYPE: DNA
<213> ORGANISM: Lama glama

<400> SEQUENCE: 198

```
cagtctgccc tgactcagcc gccctccctc tctgcatctc cgggatcatc tgtcagactc    60
acctgcaccc tgagcagtgg aaacaatatt ggcagctatg cataagttg gtaccagcag   120
aaggcaggga gccctccccg gtaccctctg aactactaca ccgactcacg caagcaccag   180
gactccgggg tcccgagccg cttctctggg tccaaagatg cctcggccaa cgcagggctt   240
ctgctcatct ctgggcttca gcccgaggac gaggctgact attactgttc tgcatacaag   300
```
agtggttctt accgttgggt gttcggcgga gggacgcacg tgaccgtcct g 351

<210> SEQ ID NO 199
<211> LENGTH: 10
<212> TYPE: PRT
<213> ORGANISM: Homo sapiens

<400> SEQUENCE: 199

Glu Pro Lys Ser Cys Asp Lys Thr His Thr
1               5                   10

<210> SEQ ID NO 200
<211> LENGTH: 5
<212> TYPE: PRT
<213> ORGANISM: Homo sapiens

<400> SEQUENCE: 200

Cys Pro Pro Cys Pro
1               5

<210> SEQ ID NO 201
<211> LENGTH: 8
<212> TYPE: PRT
<213> ORGANISM: Homo sapiens

<400> SEQUENCE: 201

Ala Pro Glu Leu Leu Gly Gly Pro
1               5

<210> SEQ ID NO 202
<211> LENGTH: 12
<212> TYPE: PRT
<213> ORGANISM: Homo sapiens

<400> SEQUENCE: 202

Glu Leu Lys Thr Pro Leu Gly Asp Thr Thr His Thr
1               5                   10

<210> SEQ ID NO 203
<211> LENGTH: 5
<212> TYPE: PRT
<213> ORGANISM: Homo sapiens

<400> SEQUENCE: 203

Cys Pro Arg Cys Pro
1               5

<210> SEQ ID NO 204
<211> LENGTH: 8
<212> TYPE: PRT
<213> ORGANISM: Homo sapiens

<400> SEQUENCE: 204

Ala Pro Glu Leu Leu Gly Gly Pro
1               5

<210> SEQ ID NO 205
<211> LENGTH: 7
<212> TYPE: PRT
<213> ORGANISM: Homo sapiens

<400> SEQUENCE: 205

Glu Ser Lys Tyr Gly Pro Pro
1               5

```
<210> SEQ ID NO 206
<211> LENGTH: 5
<212> TYPE: PRT
<213> ORGANISM: Homo sapiens

<400> SEQUENCE: 206

Cys Pro Ser Cys Pro
1               5

<210> SEQ ID NO 207
<211> LENGTH: 8
<212> TYPE: PRT
<213> ORGANISM: Homo sapiens

<400> SEQUENCE: 207

Ala Pro Glu Phe Leu Gly Gly Pro
1               5

<210> SEQ ID NO 208
<211> LENGTH: 3
<212> TYPE: PRT
<213> ORGANISM: Homo sapiens

<400> SEQUENCE: 208

Glu Arg Lys
1

<210> SEQ ID NO 209
<211> LENGTH: 10
<212> TYPE: PRT
<213> ORGANISM: Homo sapiens

<400> SEQUENCE: 209

Cys Cys Val Glu Cys Pro Pro Pro Cys Pro
1               5                   10

<210> SEQ ID NO 210
<211> LENGTH: 7
<212> TYPE: PRT
<213> ORGANISM: Homo sapiens

<400> SEQUENCE: 210

Ala Pro Pro Val Ala Gly Pro
1               5
```

ANTI-MET AGONIST ANTIBODY FOR USE IN THE TREATMENT OF COLORECTAL CANCER

FIELD OF THE INVENTION

The present invention relates to treatment of cancer using agonist anti-MET antibodies or fragments thereof. In particular, the invention relates to treatment of colorectal cancer using agonist anti-MET antibodies or fragments, typically colorectal cancer associated with chronic inflammation and/or gene mutations in the colon and in the gastrointestinal tract in general. The invention further relates to treating intestinal fibrosis using agonist anti-MET antibodies.

BACKGROUND

HGF is a pleiotropic cytokine of mesenchymal origin that mediates a characteristic array of biological functions including cell proliferation, motility, differentiation and survival. The HGF receptor, also known as MET, is expressed by a variety of tissues including all epithelia, the endothelium, muscle cells, neuronal cells, osteoblasts, hematopoietic cells and various components of the immune system. HGF and MET signalling plays an essential role during embryo development, where it guides migration of precursor cells and determines cell survival or death.

In adults, HGF/MET signalling is ordinarily quiescent and is resumed during wound healing and tissue regeneration. Some cancers and tumours hijack HGF/MET signalling in order to promote the survival and proliferation of the tumour in the host organism.

Therefore, inhibiting the HGF-MET axis has become a popular target for anti-cancer treatment. Use of an agonist of HGF-MET as an anti-cancer therapy has not previously been demonstrated.

Colorectal cancer is the third most common cancer in terms of incidence, with a 5 year survival rate of approximately 65%. Subjects particularly at risk include those with inflammatory bowel disease, or genetic predispositions (e.g. those with a history of hereditary nonpolyposis colorectal cancer (HNPCC or Lynch syndrome), Gardner syndrome, or familial adenomatous polyposis (FAP)). Treatment with surgery (e.g. colectomy) and/or chemotherapy and radiotherapy can be effective, but lead to significant loss in standard of living. There is therefore a need for effective therapies for colorectal cancer.

SUMMARY OF THE INVENTION

HGF is a known pro-oncogenic factor that plays a key role in tumorigenesis of various tissues and organs, including the gastro-intestinal tract (Gherardi et al. Nat Rev Cancer 12:89-103, 2012; Vermeulen et al. Nat Cell Biol. 12:468-476, 2010; Samamé Pérez-Vargas et al. Int J Mol Sci. 14:18056-18077, 2013; Stein et al. Nat Med. 15: 59-67, 2009, each of which is incorporated herein by reference). As a result, inhibiting HGF-MET has become a popular target for anti-cancer treatment. However, it is surprisingly identified herein that an agonist of HGF-MET acts as an effective anti-cancer therapy.

Therefore, in a first aspect, the invention provides a method of treating cancer in a subject, the method comprising administering to the subject an HGF-MET agonist. In certain preferred embodiments, the HGF-MET agonist is an anti-MET agonist antibody or antigen fragment thereof.

Surprisingly, an HGF-MET agonist (e.g. an anti-MET agonist antibody) is particularly effective as a therapy for colorectal cancer, as demonstrated herein. Without wishing to be bound by theory, it is hypothesised that stimulation of the HGF-MET signalling promotes regeneration and homeostatic mechanisms of intestinal epithelial cells, thereby dampening potentially oncogenic mechanisms (Nakamura et al., J Gastroenterol Hepatol. 1:188-202, 2011, incorporated herein by reference).

In a further aspect, the invention provides a method of treating colorectal fibrosis in a subject, the method comprising administering to a subject an HGF-MET agonist.

Advantageously, it is also demonstrated herein that HGF-MET agonists are surprisingly effective at treating colorectal cancer in inflamed guts. Further advantageously, it is also demonstrated herein that HGF-MET agonists are surprisingly effective at treating colorectal fibrosis in inflamed guts.

This is particularly advantageous since patients suffering from colorectal inflammation are at increased risk of colorectal cancer and also from fibrosis. For instance, patients suffering from inflammatory bowel disease (IBD; i.e. Crohn's Disease or ulcerative colitis) are predisposed to colorectal cancer and will advantageously benefit from the methods described herein. Furthermore, HGF-MET agonists can also relieve the symptoms of the underlying IBD itself. Therefore the methods of the invention will lead to a synergistic effect in IBD patients whereby colorectal cancer in these patients can be treated and, furthermore, the patient's IBD is also treated. Similarly, the methods of the invention will lead to a synergistic effect in IBD patients whereby colorectal fibrosis in these patients can be treated and, furthermore, the patient's IBD is also treated.

Therefore, in a further preferred embodiment, the method of the invention is a method of treating colorectal cancer in a patient or subject identified as at increased risk of colorectal cancer. In certain embodiments, the subject has been diagnosed with colorectal inflammation prior to administration of the HGF-MET agonist. In certain embodiments of the methods described herein, the subject has IBD (ulcerative colitis or Crohn's Disease). In preferred such embodiments, the HGF-MET agonist administered to the subject is an anti-MET agonist antibody.

Similarly, in a further preferred embodiment, the method of the invention is a method of treating colorectal fibrosis in a patient or subject identified as at increased risk of colorectal fibrosis. In certain embodiments, the subject has been diagnosed with colorectal inflammation prior to administration of the HGF-MET agonist. In certain embodiments of the methods described herein, the subject has IBD (ulcerative colitis or Crohn's Disease). In preferred such embodiments, the HGF-MET agonist administered to the subject is an anti-MET agonist antibody.

In a further aspect is provided an HGF-MET agonist for use in methods of treatment of cancer (e.g. colorectal cancer) in a subject as described herein. In preferred such embodiments, the HGF-MET agonist is an anti-MET agonist antibody or antigen fragment thereof.

In a further aspect is provided an HGF-MET agonist for use in methods of treatment of colorectal fibrosis in a subject as described herein. In preferred such embodiments, the HGF-MET agonist is an anti-MET agonist antibody or antigen fragment thereof.

In a further aspect is provided a pharmaceutical composition for use in methods of treating cancer (e.g. colorectal cancer) as described herein, wherein the pharmaceutical composition comprises an HGF-MET agonist and a pharmaceutically acceptable excipient or carrier. In preferred such embodiments, the HGF-MET agonist is an anti-MET agonist antibody or antigen fragment thereof.

In a further aspect is provided a pharmaceutical composition for use in methods of treating colorectal fibrosis as described herein, wherein the pharmaceutical composition comprises an HGF-MET agonist and a pharmaceutically acceptable excipient or carrier. In preferred such embodiments, the HGF-MET agonist is an anti-MET agonist antibody or antigen fragment thereof.

In a preferred embodiment of all aspects of the invention, the subject or patient is a human.

In a preferred embodiment of all aspects of the invention, the HGF-MET agonist is a full agonist.

In a preferred embodiment of all aspects of the invention, the HGF-MET agonist is an anti-MET agonist antibody.

DRAWINGS

Figure 1B:
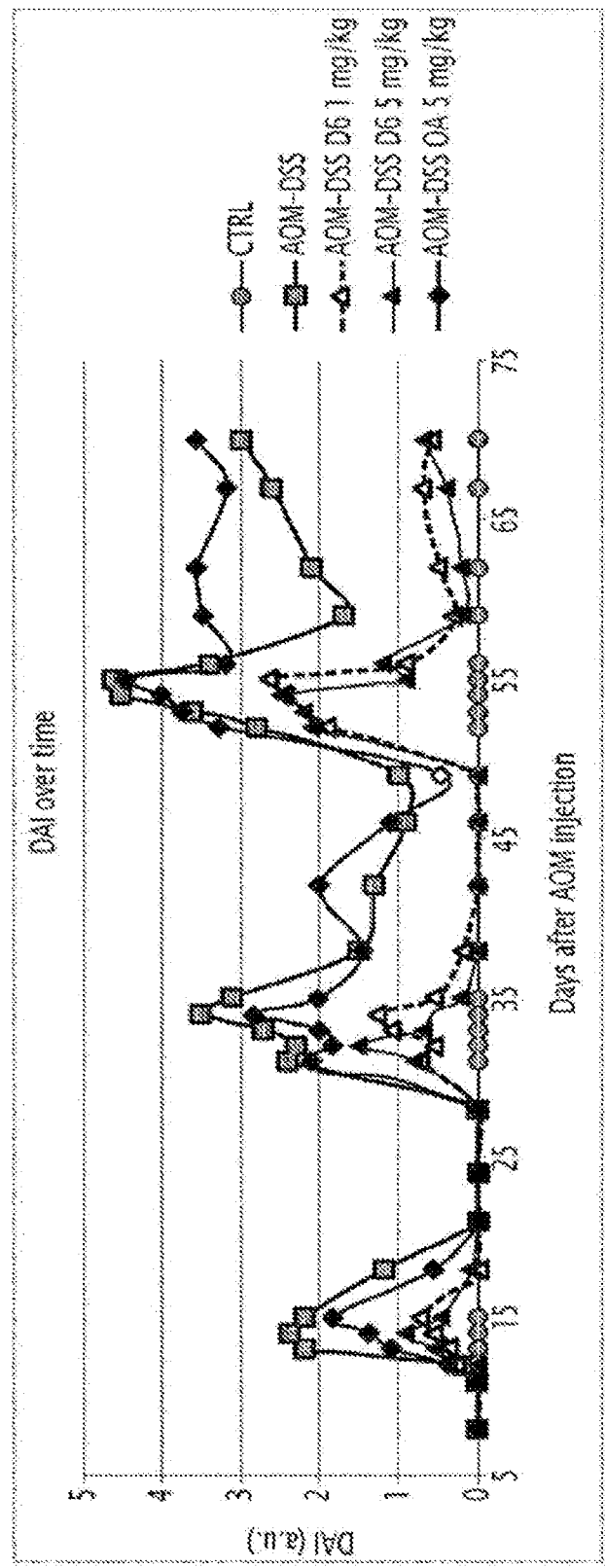

FIGS. 1A and 1B. AOM/DSS colon carcinogenesis model: body weight and disease activity index (DAI) overtime. Colitis-associated colorectal cancer was induced in BALB/c mice by i.p. administration of azoxymethane (AOM) at a dose of 12.5 mg/kg followed by three cycles of dextran sodium sulphate (DSS) in the drinking water at a concentration of 6%. Each cycle consisted of 7 days of DSS treatment followed by 14 days of regular water. Starting from day 1, mice were randomized into 4 arms which received treatment with: (i) vehicle only (PBS); (ii) the MET agonistic 71 D6 antibody at a dose of 1 mg/kg; (iii) the MET agonistic 71 D6 antibody at a dose of 5 mg/kg; (iv) the MET antagonistic antibody 74C8-OA at a dose of 5 mg/kg. An additional, fifth control arm contained 7 mice that received no AOM-DSS or antibody and served as healthy control. Antibodies were delivered by i.p. injection two times a week. During the whole course of the experiment, mouse weight was monitored on a regular basis, and the clinical symptoms of ulcerative colitis were assessed by determining fecal blood, rectal bleeding and stool consistency. Each parameter was given a score from 0 (absence of the symptom) to 3 (maximal manifestation of the symptom). Scores relative to the single parameters were summed together to give rise to the DAI ranging from 0 to 9. (FIG. 1A) Body weight over time. (FIG. 1B) DAI over time.

Figure 2:
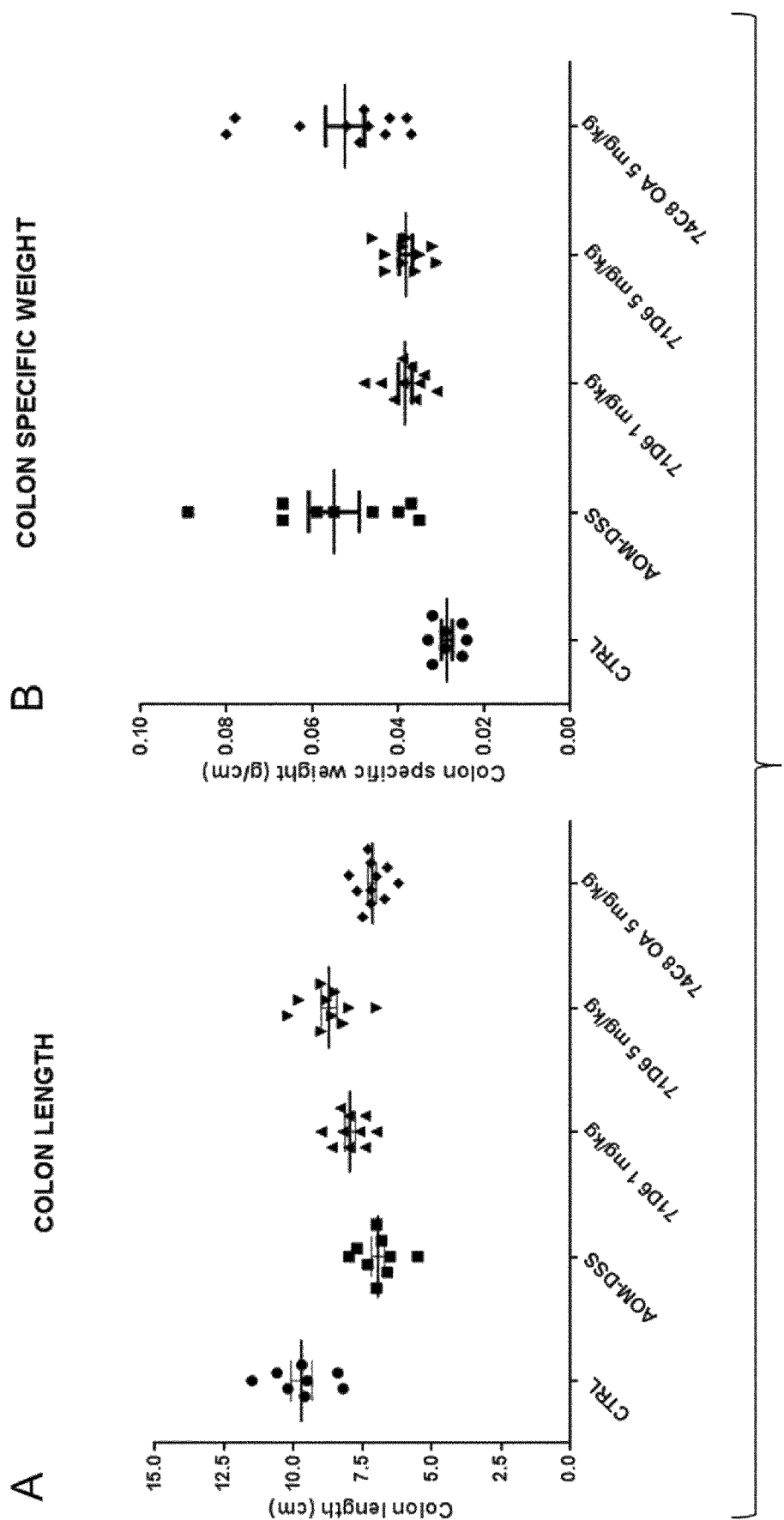

FIG. 2. AOM/DSS colon carcinogenesis model: colon length and specific weight. Colitis-associated cancer was induced in BALB/c mice as described in FIG. 1 legend. At autopsy, colon specimens were collected and washed through. Tissues were weighed and their length was determined using a ruler. (A) Colon length. (B) Colon specific weight.

Figure 3:
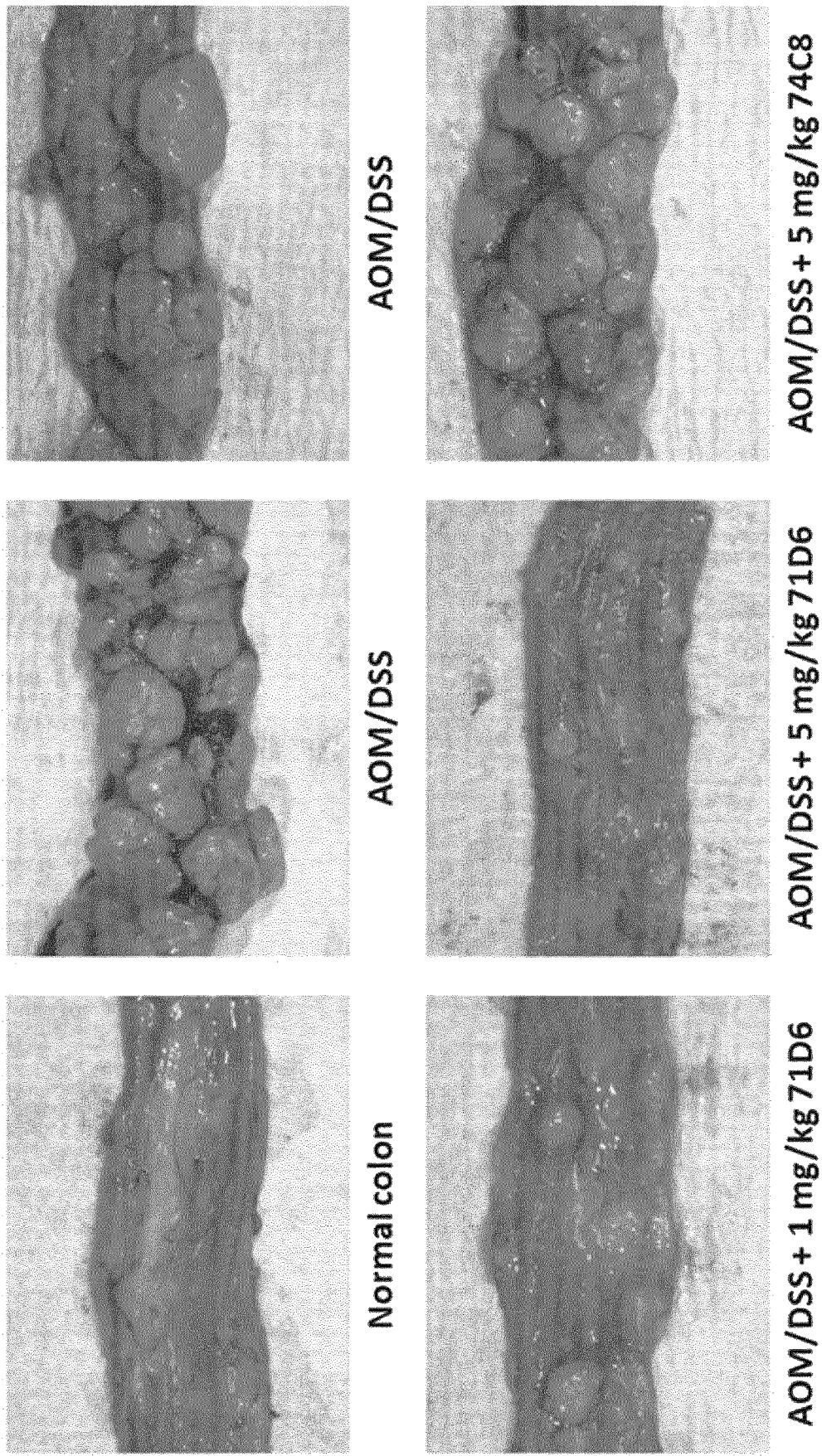

FIG. 3. AOM/DSS colon carcinogenesis model: representative images of intestinal tumours. Colitis-associated cancer was induced in BALB/c mice as described in FIG. 1 legend. At autopsy, colon specimens were collected and washed through. Following length and weight measurement, colons were opened with a longitudinal cut and stained with 1% Alcian Blue solution to highlight tumour borders. Colon specimens were analyzed by placing the flattened tissue under a stereo-microscope with their inner (lumen) side towards the lens, and photographed. Magnification: 1×.

Figure 4A:
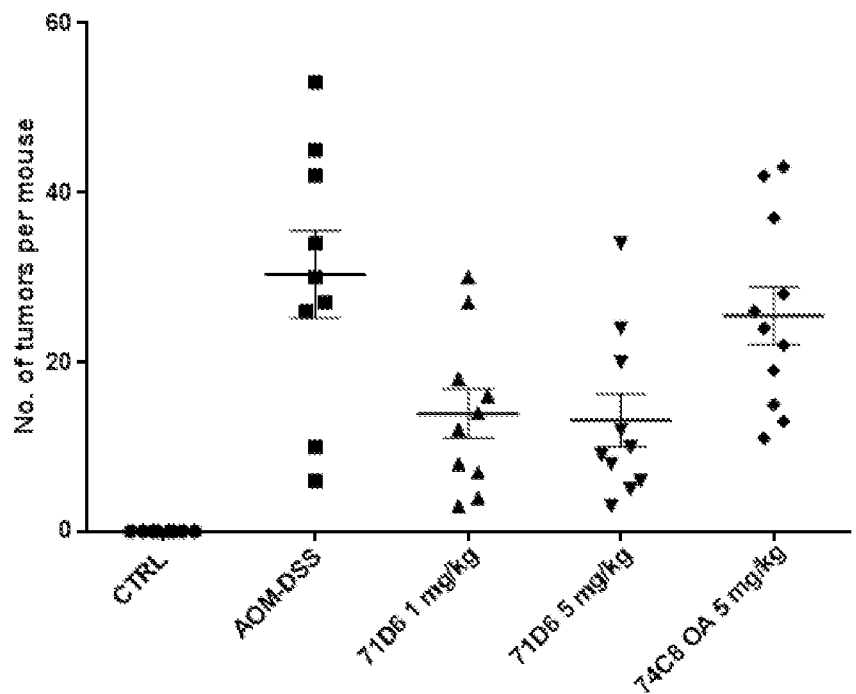
Figure 4B:
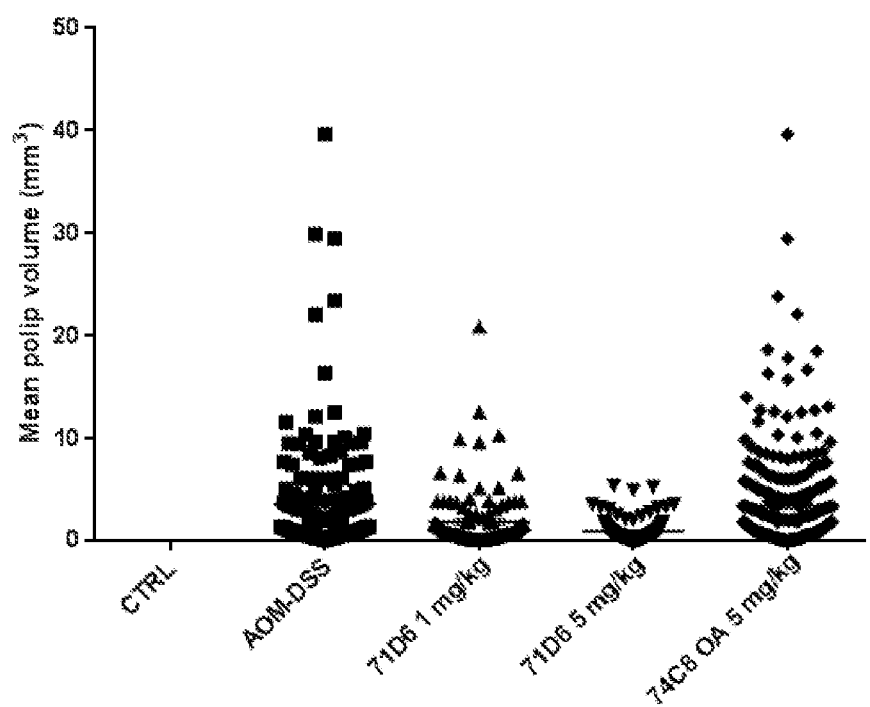
Figure 4C:
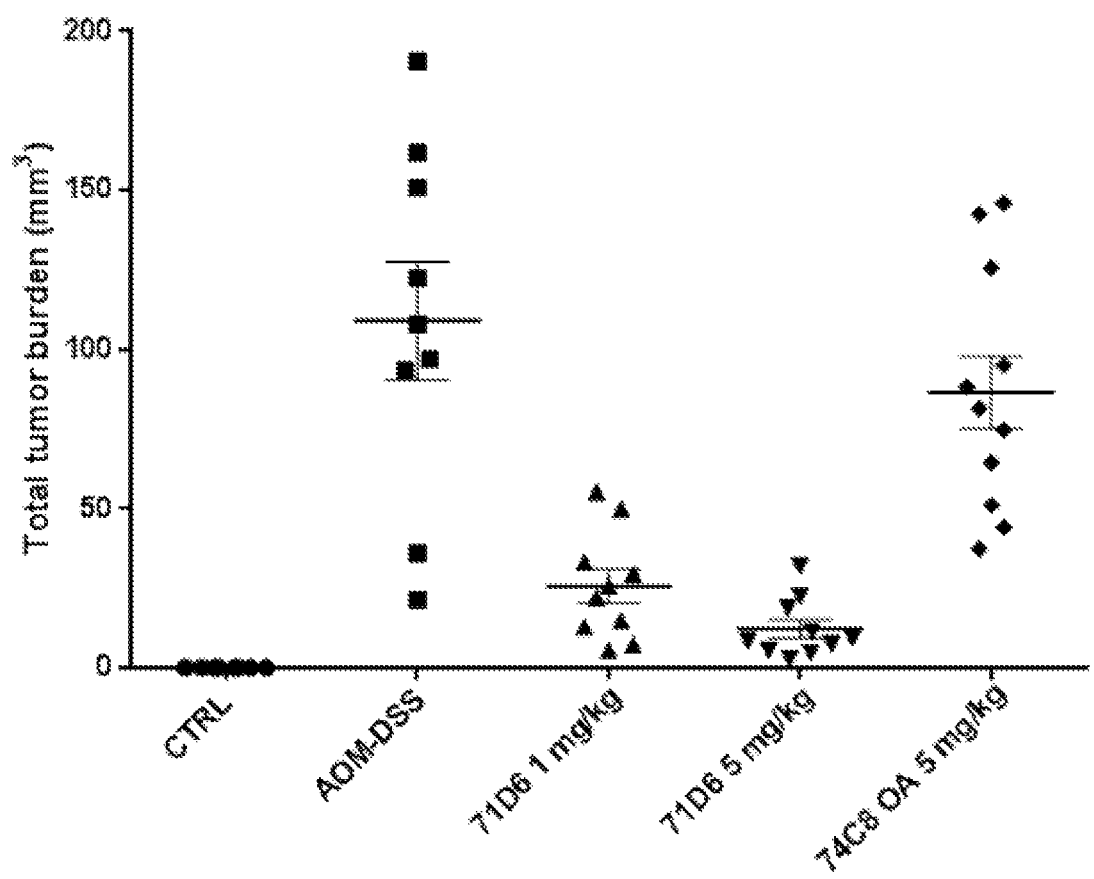

FIGS. 4A-4C. AOM/DSS colon carcinogenesis model: analysis of mean tumour number, mean tumour volume and total tumour burden. Colitis-associated cancer was induced in BALB/c mice as described in FIG. 1 legend, and carcinogenesis was quantified using a stereo-microscope. (FIG. 4A) Tumour number. The number of polyps in each colon sample was scored directly. (FIG. 4B) Mean tumour volume.

Tumour photographs were analyzed using Image J software (National Instututes of Health) and the volume of the polips was calculated using the formula $V=\frac{3}{4}\pi(X/2)-(Y/2)^2$, where V is the volume of the polip, and X and Y are the major and minor dimensions of the polip section, respectively (in mm). (FIG. 4C) Total tumour burden. Total tumour burden (volume) was calculated by multiplying the mean tumour volume by the number of tumours in each mouse.

Figure 5:
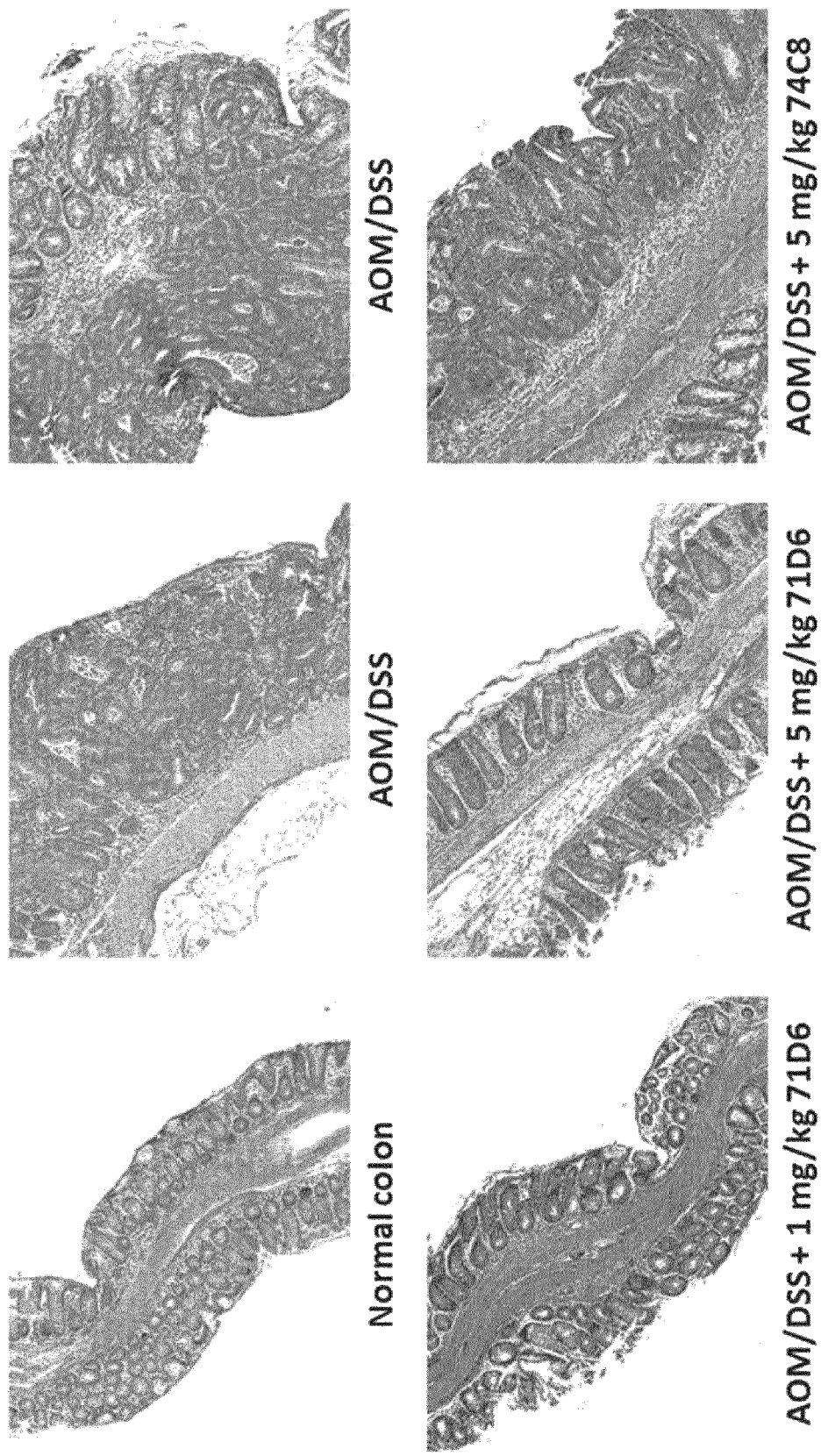

FIG. 5. AOM/DSS colon carcinogenesis model: histological analysis of colon samples. Colitis-associated cancer was induced in BALB/c mice as described in FIG. 1 legend. Following tissue processing and paraffin embedding, colon specimens were cut using a microtome and prepared for histological and immunohistochemical analysis. Here, we show representative images of colon sections stained with hematoxylin and eosin. Magnification: 100×.

Figure 6:
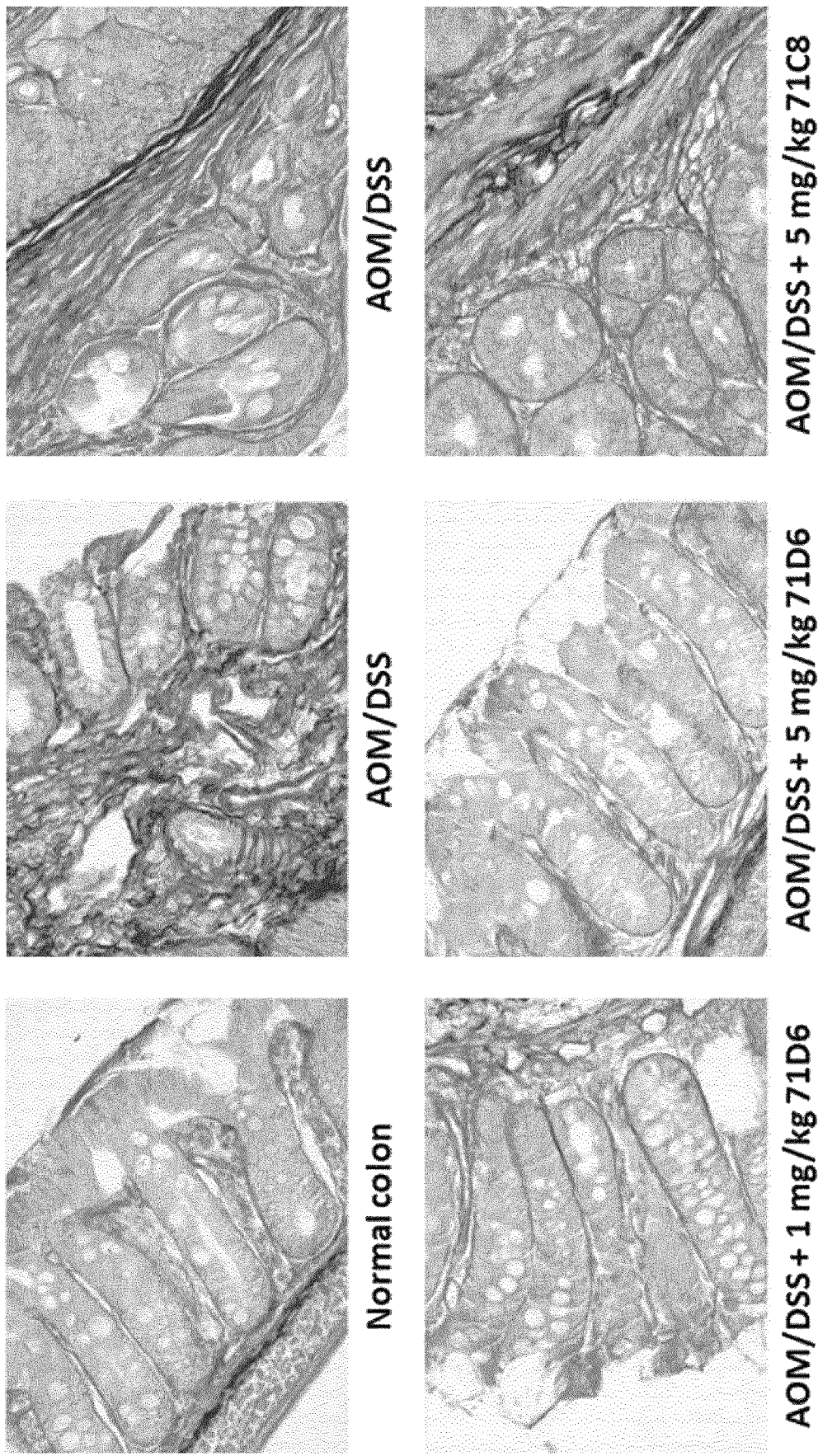

FIG. 6. AOM/DSS colon carcinogenesis model: immunohistochemical analysis of collagen deposition. Colitis-associated cancer was induced in BALB/c mice as described in FIG. 1 legend. Colon sections were analyzed by immunohistochemistry. Here, we show representative images of colon sections stained with picro-sirius red, which highlights collagen deposition, a hallmark of tissue fibrosis. Magnification: 400×.

Figure 7:
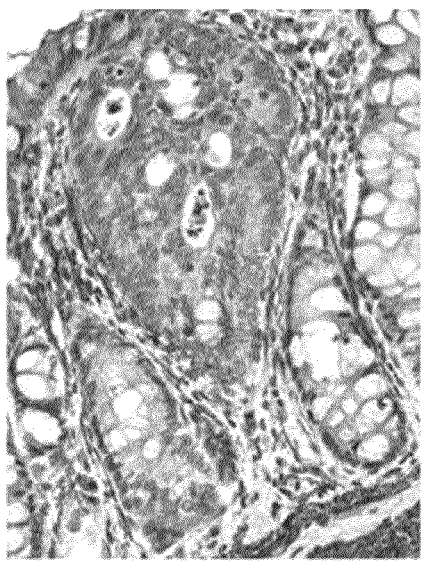
Figure 7:
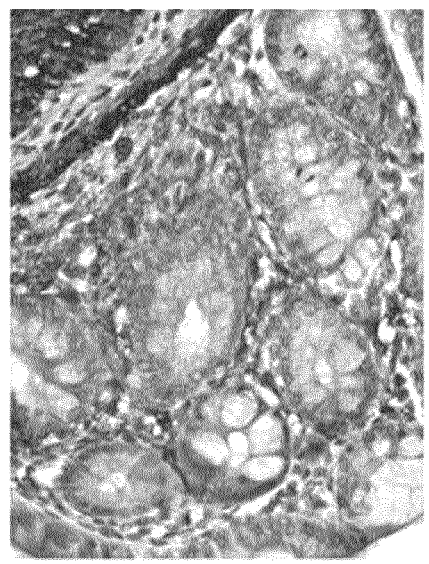
Figure 7:
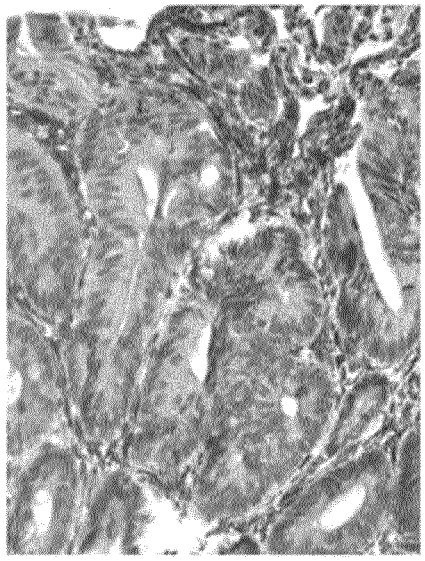
Figure 7:
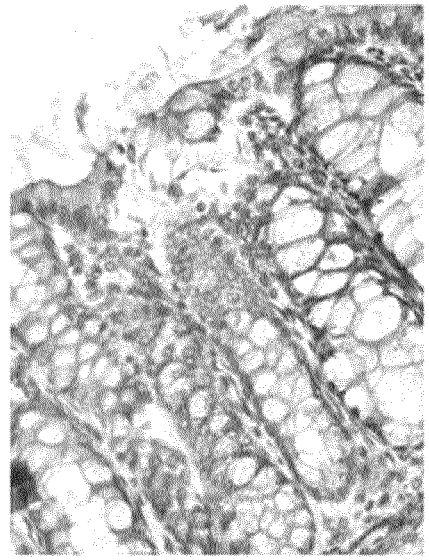
Figure 7:
Figure 7:
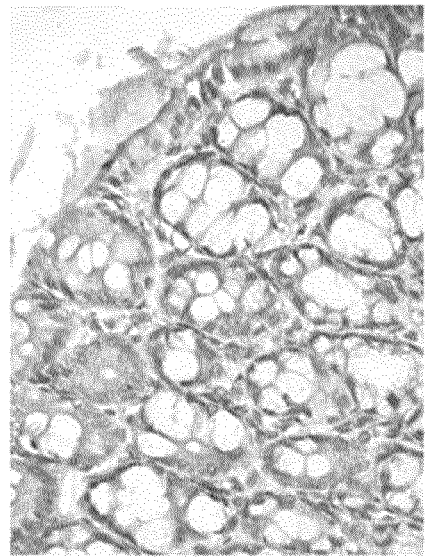

FIG. 7. AOM/DSS colon carcinogenesis model: immunohistochemical analysis of myofibroblast content. Colitis-associated cancer was induced in BALB/c mice as described in FIG. 1 legend. Colon sections were analyzed by immunohistochemistry. Here, we show representative images of colon sections stained with anti-alpha smooth muscle actin ($\alpha$-SMA) antibodies, which specifically identify myofibroblasts. Myofibroblast accumulation is a hallmark of fibrosis. Magnification: 400×.

Figure 8:
Figure 8:
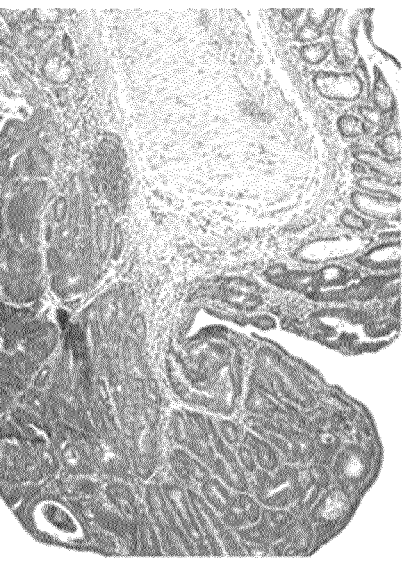
Figure 8:
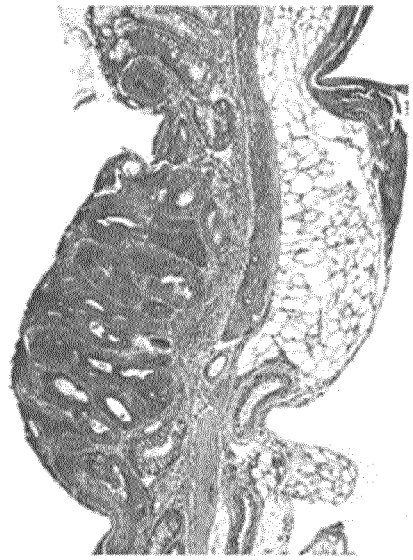
Figure 8:
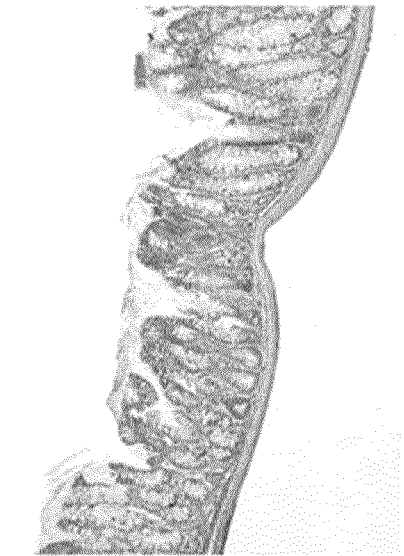
Figure 8:

FIG. 8. AOM/DSS colon carcinogenesis model: immunohistochemical analysis of TGF-$\beta$ expression. Colitis-associated cancer was induced in BALB/c mice as described in FIG. 1 legend. Colon sections were analyzed by immunohistochemistry. Here, we show representative images of colon sections stained with anti-transforming growth factor beta (TGF-$\beta$) antibodies. TGF-$\beta$ signalling has been demonstrated to be frequently deregulated in human cancers, including colorectal cancer. While in normal or premalignant cells it usually acts as a tumour suppressor, in advanced cancer it is frequently overexpressed and the growth inhibitory function switch to an oncogenic one thus promoting tumour cell proliferation and invasion.

Figure 9:
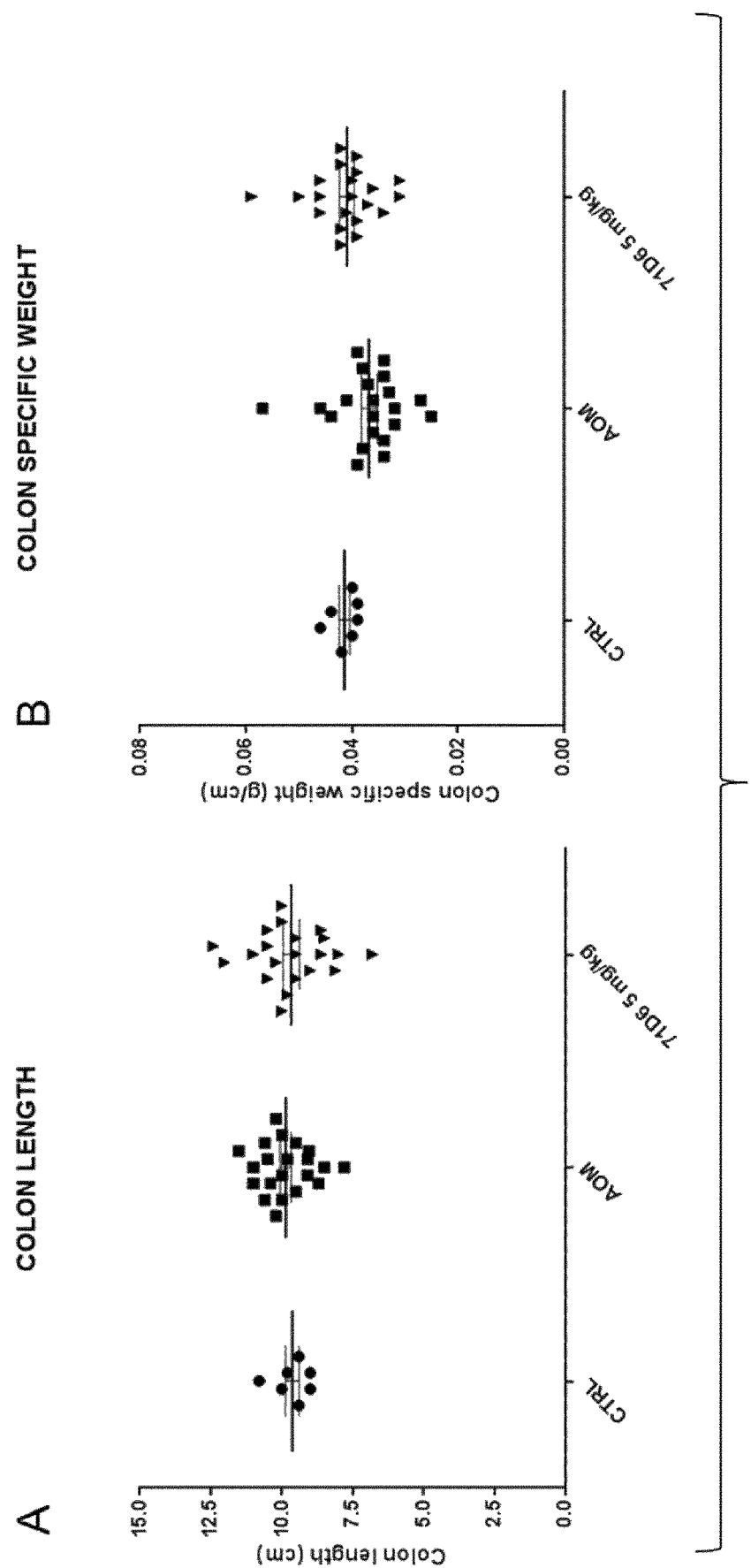

FIG. 9. AOM colon carcinogenesis model: colon length and specific weight. Mutagenesis-induced colorectal cancer was induced in BALB/c mice by i.p. administration of azoxymethane (AOM) at a dose of 5 mg/kg once a week for 6 weeks. Starting from day 1, mice were randomized into 2 arms of 21 mice each which received treatment with 71 D6 (at a dose of 5 mg/kg) or vehicle only (PBS). Antibody was administered two times a week by i.p. injection. An additional, third control arm contained 7 mice that received no AOM or antibody and served as healthy control. Mice were sacrificed 8 weeks after the last AOM injection, i.e. 14 weeks after the experiment started. At autopsy, colons were collected and washed through. Explanted colons were measured using a ruler and weighed. (A) Colon length. (B) Colon specific weight.

Figure 10:
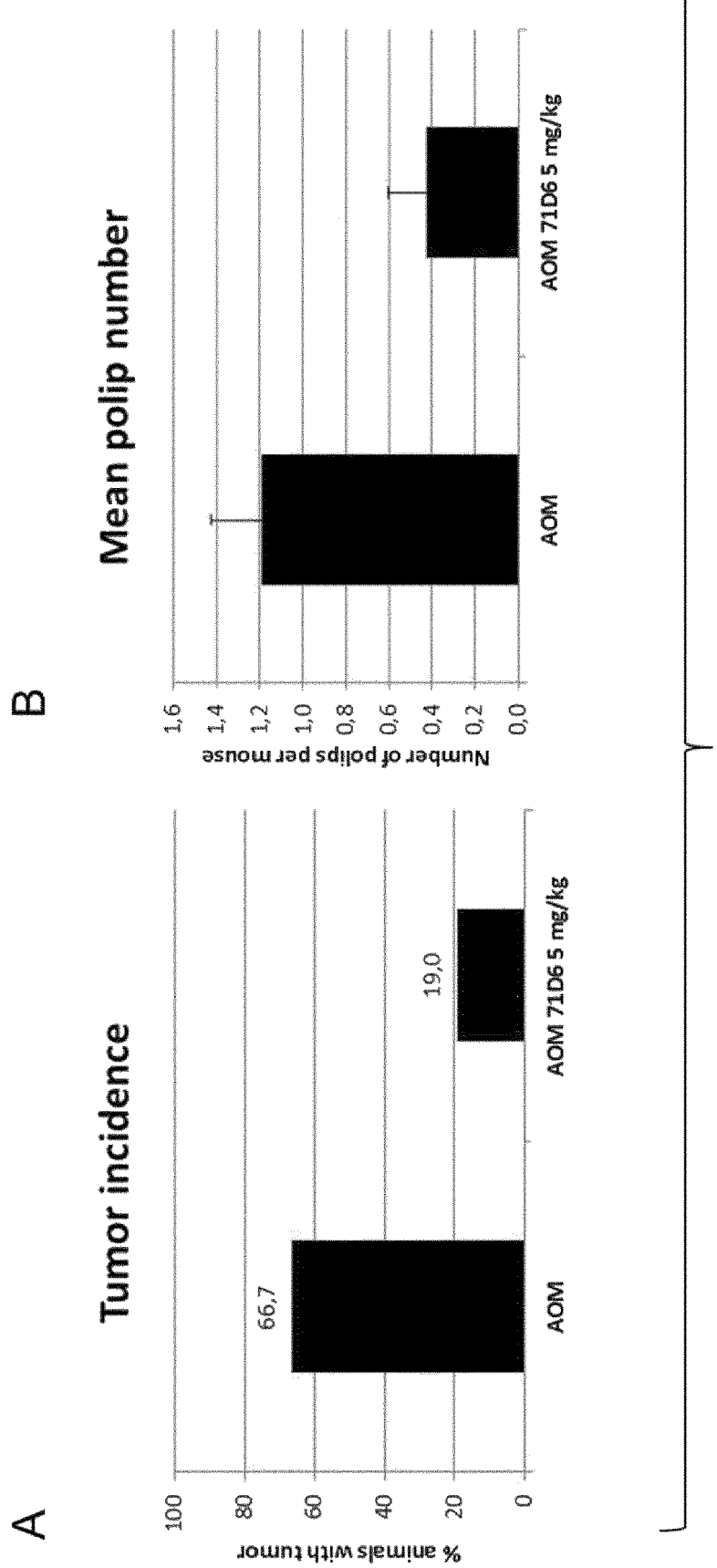

FIG. 10. AOM colon carcinogenesis model: tumour incidence and number. Mutagenesis-induced colorectal cancer was induced in BALB/c mice as described in FIG. 9 legend. Following measurements, colons were cut open longitudinally to expose tumour masses. Tissues were stained ex vivo with a 1% Alcian Blue solution in order to highlight tumour borders. Polips were counted using a stereo-microscope. (A) Tumour incidence. (B) Mean tumour number.

Figure 11:
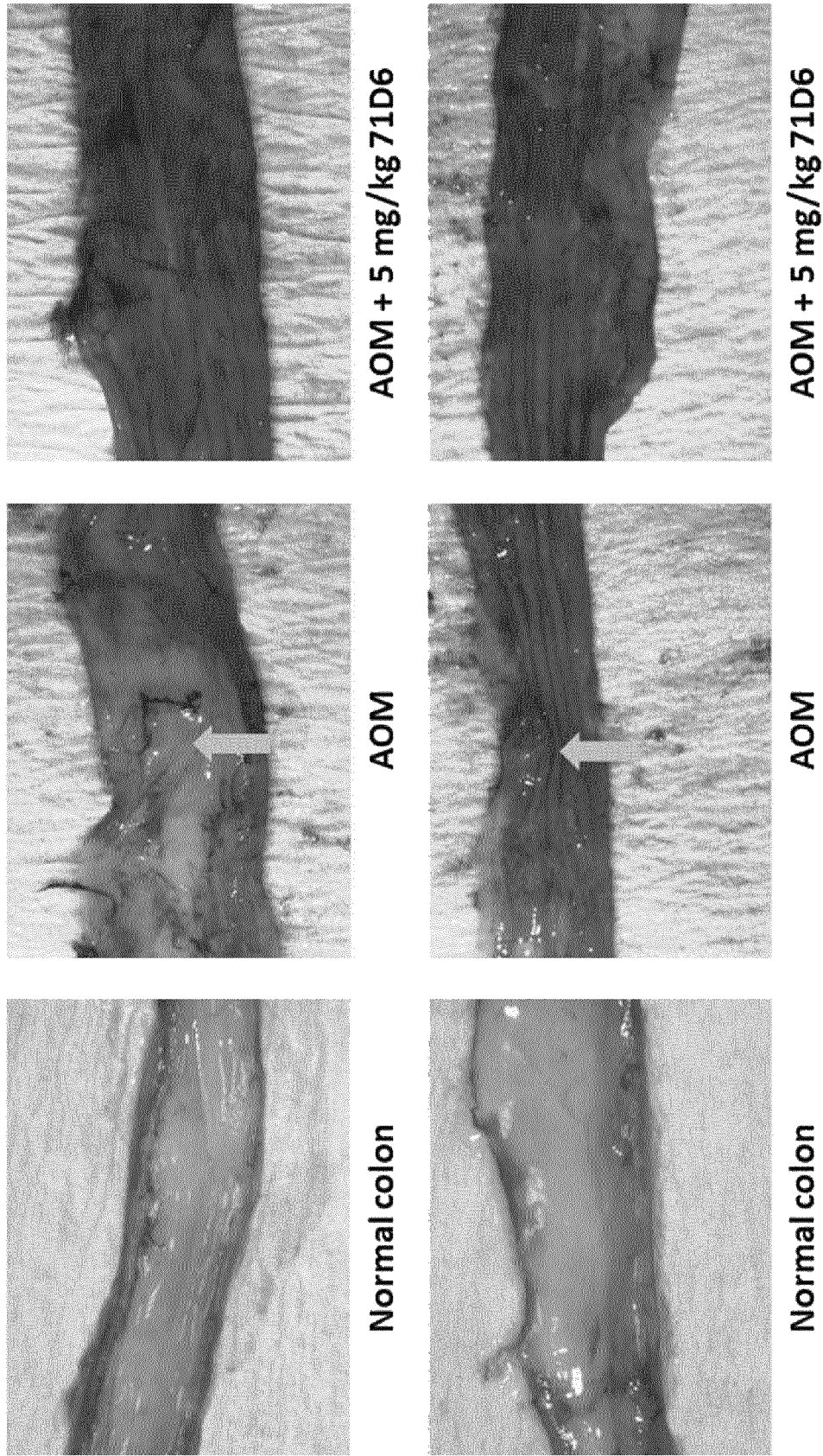

FIG. 11. AOM colon carcinogenesis model: representative images of colon tumours. Representative images of the tumours quantified in FIG. 10. Arrows indicate macroscopically evident tumour masses. Magnification: 1×.

Figure 12A:
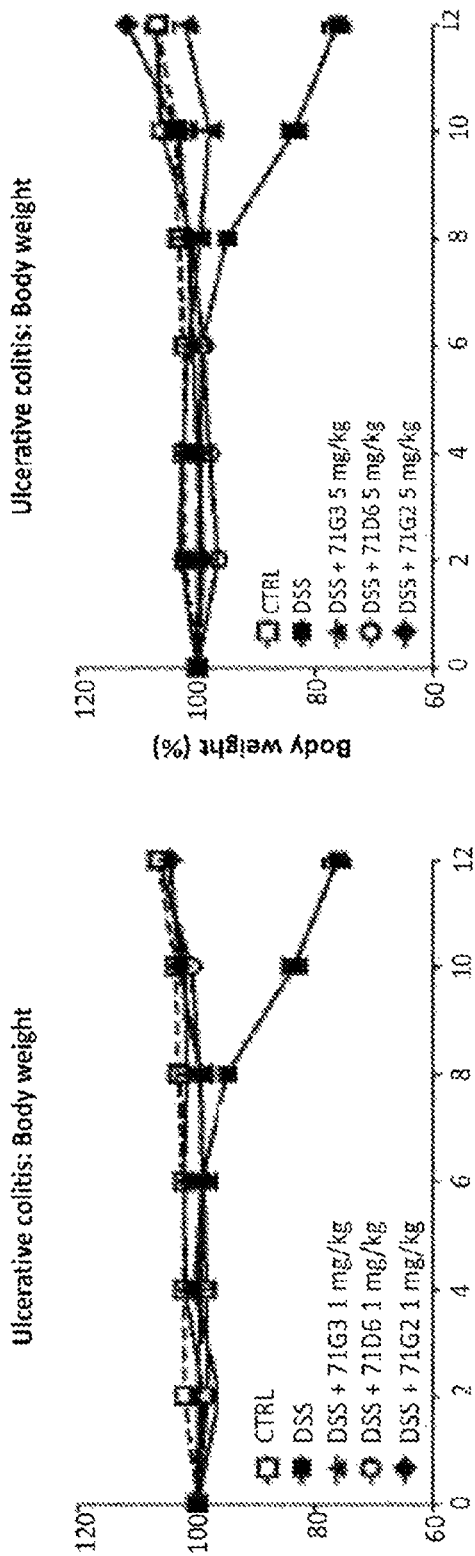
Figure 12B:
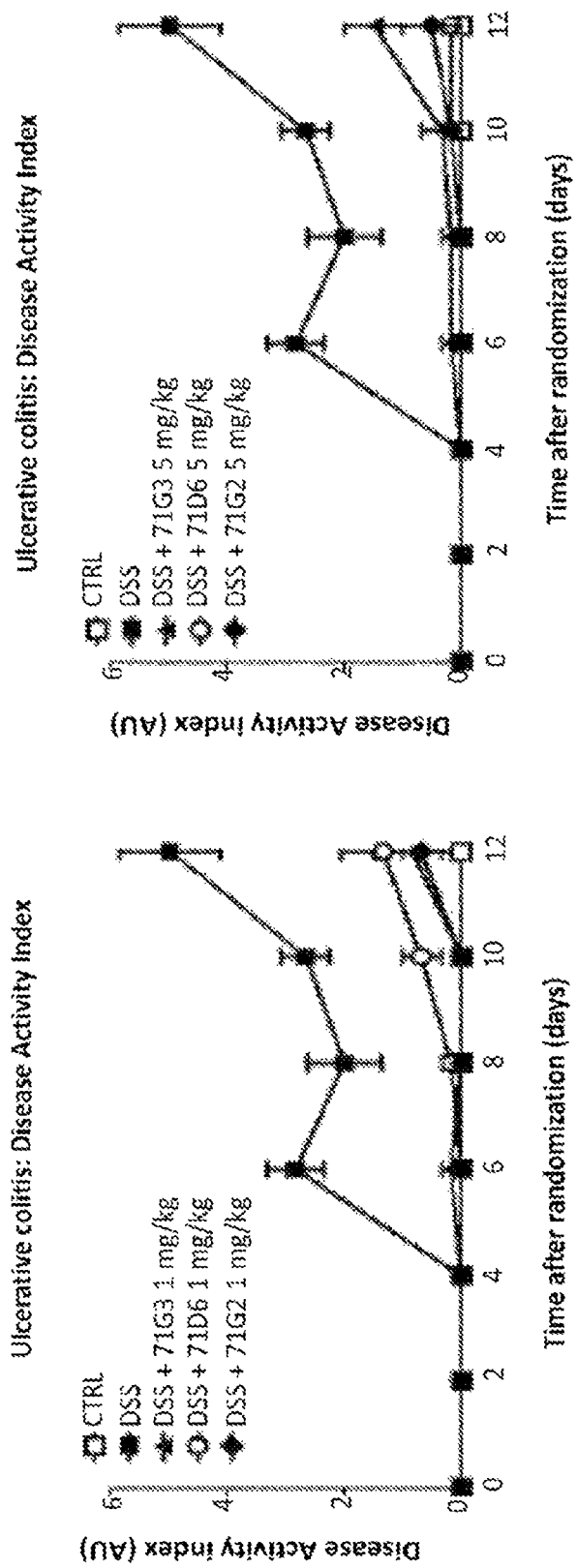
Figure 12C:
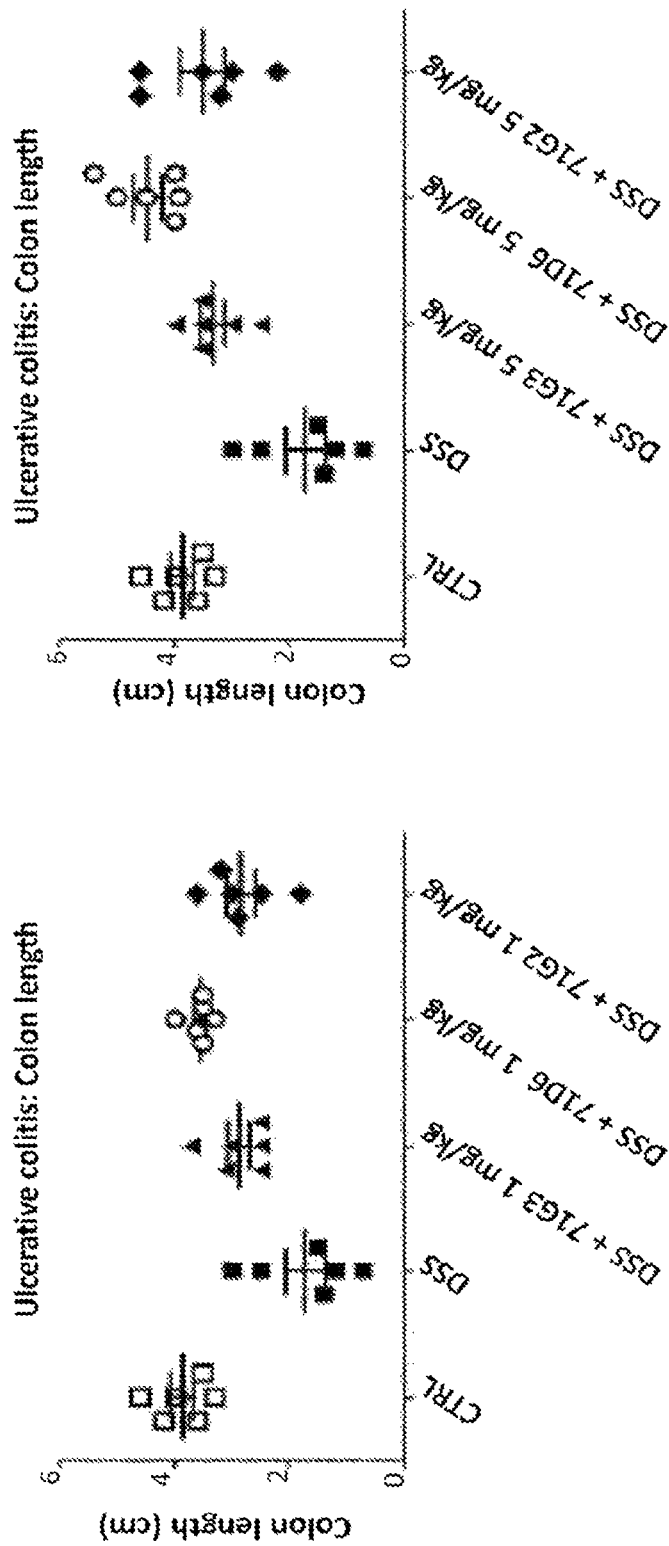

FIGS. 12A-12C. Intestinal (colorectal) inflammation model. Dextran sodium sulphate (DSS) was added to the drinking water of Balb/c mice for 10 days. On day 10, DSS treatment was interrupted and mice were put back on normal water. Starting from day 1, mice were randomized into 7 arms which received treatment with 71G3, 71 D6, 71G2 (at a dose of 1 mg/kg or 5 mg/kg) or vehicle only (PBS). An additional, eighth control arm received no DSS or antibody and served as healthy control. Mice were sacrificed on day 12, i.e. 2 days after DSS administration was interrupted. At autopsy, colons were collected, washed through, and their length was determined using a ruler. Following measurement, colons were embedded in paraffin and processed for histological analysis. During the whole course of the experiment, mouse weight was monitored on a regular basis, and the clinical symptoms of ulcerative colitis were assessed by determining faecal blood, rectal bleeding and stool consistency. Each parameter was given a score from 0 (absence of the symptom) to 3 (maximal manifestation of the symptom). Scores relative to the single parameters were summed together to give rise to the DAI ranging from 0 to 9. (FIG. 12A) Body weight over time (% relative to time 0). (FIG. 12B) DAI over time. (FIG. 12C) Colon length at autopsy. Data of the 1 mg/kg arms and of the 5 mg/kg arms are shown in separate graphs for clarity.

Figure 13:
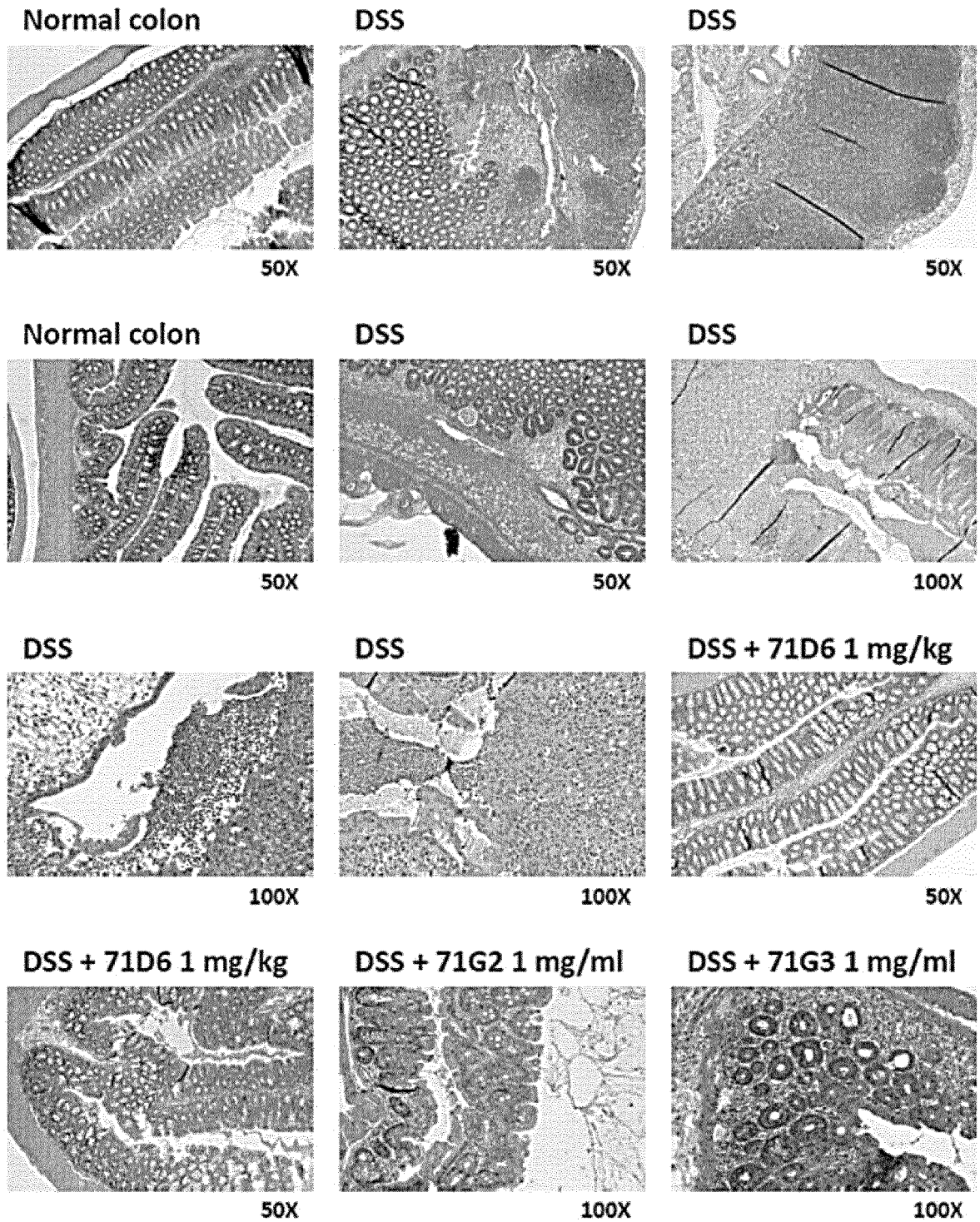

FIG. 13. Intestinal (colorectal) inflammation model. BALB/c mice were exposed to dextran sodium sulphate (DSS) as described in FIG. 12 legend. At autopsy, colons were collected, measured, and then embedded in paraffin and processed for histological analysis. Colon sections were stained with hematoxylin and eosin, examined by microscopy, and photographed. Experimental arm, antibody dose and magnification are indicated close to each image.

DETAILED DESCRIPTION

As used herein, the terms "MET protein" or "MET antigen" or "MET" are used interchangeably and refer to the receptor tyrosine kinase that, in its wild-type form, binds Hepatocyte Growth Factor (HGF). "MET" as used herein refers to human MET unless otherwise specified. The terms "human MET protein" or "human MET receptor" or "human MET" or "hMET" are used interchangeably to refer to human MET (GenBank accession number: X54559), including the native human MET protein naturally expressed in the human host and/or on the surface of human cultured cell lines, as well as recombinant forms and fragments thereof and also naturally occurring mutant forms. The terms "mouse MET protein" or "mouse MET receptor" or "mouse MET" or "mMET" are used interchangeably to refer to mouse MET (GenBank accession number: NM_008591), including the native mouse MET protein naturally expressed in the mouse host and/or on the surface of mouse cultured cell lines, as well as recombinant forms and fragments thereof and also naturally occurring mutant forms.

As used herein, "HGF-MET agonist" and "MET agonist" are used interchangeably to refer to non-native agents that promote signalling via the MET protein—i.e. agents other than HGF that bind MET and increase MET signalling. Agonist activity on binding of MET by MET agonists is indicated by molecular and/or cellular responses that (at least partially) mimic the molecular and cellular responses induced upon HGF-MET binding. Suitable methods for measuring MET agonist activity are described herein, including the Examples. A "full agonist" is a MET agonist that increases MET signalling in response to binding to an extent at least similar, and optionally exceeding, the extent to which MET signalling increases in response to binding of the native HGF ligand. Examples of the level of MET signalling induced by "full agonists", as measured by different methods of determining MET signalling, are provided herein.

HGF-MET agonists may be small molecules, binding proteins such as antibodies or antigen binding fragments, aptamers or fusion proteins. A particular example of a MET agonist is an anti-MET agonist antibody.

As used herein, "treatment" or "treating" refers to effective therapy of the relevant condition (cancer (e.g. colorectal cancer) or fibrosis)—that is, an improvement in the health of the subject. Treatment may be therapeutic or prophylactic treatment—that is, therapeutic treatment of subjects suffering from the condition, or prophylactic treatment of a subject so as to reduce their risk of contracting the condition or the severity of the condition once contracted. Therapeutic treatment may be characterised by improvement in the health of the subject compared to prior to treatment. Therapeutic treatment may be characterised by improvement in the health of the subject compared to a comparable control subject that has not received treatment. Prophylactic treatment may be characterised by improvement in the health of the subject compared to a control subject (or population of control subjects) that has not been treated.

As used herein, the term "antibody" includes an immunoglobulin having a combination of two heavy and two light chains which have significant specific immuno-reactive activity to an antigen of interest (e.g. human MET). The terms "anti-MET antibodies" or "MET antibodies" are used interchangeably herein to refer to antibodies which exhibit immunological specificity for human MET protein. "Specificity" for human MET does not exclude cross-reaction with species homologues of MET. In particular, "agomAbs" as used herein refers MET antibodies that bind to both human MET and mouse MET.

"Antibody" as used herein encompasses antibodies of any human class (e.g. IgG, IgM, IgA, IgD, IgE) as well as subclasses/isotypes thereof (e.g. IgG1, IgG2, IgG3, IgG4, IgA1). Antibody as used herein also refers to modified antibodies. Modified antibodies include synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. In addition, the term "modified antibody" includes multivalent forms of antibodies (e.g., trivalent, tetravalent, etc., antibodies that bind to three or more copies of the same antigen).

Antibodies described herein may possess antibody effector function, for example one or more of antibody dependent cell-mediated cytotoxicity (ADCC), complement dependent cytotoxicity (CDC) and antibody dependent cellular phagocytosis (ADCP). Alternatively, in certain embodiments antibodies for use according to the invention have an Fc region that has been modified such that one or more effector functions, for example all effector functions, are abrogated.

Antibodies comprise light and heavy chains, with or without an interchain covalent linkage between them. An antigen-binding fragment of an antibody includes peptide fragments that exhibit specific immuno-reactive activity to the same antigen as the antibody (e.g. MET). Examples of antigen-binding fragments include scFv fragments, Fab fragments, and F(ab')2 fragments.

As used herein, the terms "variable region" and "variable domain" are used interchangeably and are intended to have equivalent meaning. The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1 (λ), L2(λ) and L3(λ) and may be defined as comprising residues 24-33 (L1(λ), consisting of 9, 10 or 11 amino acid residues), 49-53 (L2(λ), consisting of 3 residues) and 90-96 (L3(λ), consisting of 5 residues) in the VL domain (Morea et al., Methods 20, 267-279, 2000). The first, second and third hypervariable loops of the VKappa light chain domain are referred to herein as L1 (κ), L2(κ) and L3(κ) and may be defined as comprising residues 25-33 (L1(κ), consisting of 6, 7, 8, 11, 12 or 13 residues), 49-53 (L2(κ), consisting of 3 residues) and 90-97 (L3(κ), consisting of 6 residues) in the VL domain (Morea et al., Methods 20, 267-279, 2000). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20, 267-279, 2000).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, M D, 1991) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, M D, 1991). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a p-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227, 799-817, 1992; Tramontano et al., J. Mol. Biol, 215, 175-182, 1990). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616, 1977, by Kabat et al., Sequences of Proteins of Immunological Interest, 5th Ed. Public Health Service, National Institutes of Health, Bethesda, M D, 1991, by Chothia et al., J. Mol. Biol. 196, 901-917, 1987, and by MacCallum et al., J. Mol. Biol. 262, 732-745, 1996, where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions.

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework region" or "FR region" includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable domain and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a p-sheet conformation and the CDRs form loops which connect, and in some cases form part of, the p-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161, 4083-4090, 1998). MET antibodies comprising a "fully human" hinge region may contain one of the hinge region sequences shown in Table 2 below.

Table 2

| | Human hinge sequences. | | |
|---|---|---|---|
| IgG | Upper hinge | Middle hinge | Lower hinge |
| IgG1 | EPKSC DKTHT (SEQ ID NO: 199) | CPPCP (SEQ ID NO: 200) | APEL LGGP (SEQ ID NO: 201) |
| IgG3 | ELKTPL GDTTHT (SEQ ID NO: 202) | CPRCP (EPKSCDT PPPCPRCP)3 (SEQ ID NO: 203) | APEL LGGP (SEQ ID NO: 204) |
| IgG4 | ESKYGPP (SEQ ID NO: 205) | CPSCP (SEQ ID NO: 206) | APEF LGGP (SEQ ID NO: 207) |
| IgG42 | ERK (SEQ ID NQ: 208) | CCVEC PPPCP (SEQ ID NO: 209) | APPVAGP (SEQ ID NO: 210) |

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; Kabat et al., Sequences of Proteins of Immunological Interest, 5th Ed. Public Health Service, National Institutes of Health, Bethesda, MD (1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to MET). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

As used herein, "subject" and "patient" are used interchangeably to refer to a human individual.

Method of Treating Cancer

Effective treatment of cancer with an HGF-MET agonist has not been previously demonstrated. It is surprisingly demonstrated herein that administration of an HGF-MET agonist (i.e. an agonist of MET that is not HGF) effectively treats cancer in two models. In particular, the MET agonist treated colorectal cancer in a mutagenesis model, where mice with genetic mutations were treated such that the tumour incidence and number of tumours was reduced compared to untreated controls, and also, further advantageously, compared to administration of the native MET ligand (HGF). Furthermore, administration of a MET agonist also prevented development of tumours in a model of intestinal (colorectal) inflammation-induced tumour formation. Notably, a MET antagonist agent failed to treat cancer in either model.

Accordingly, in a first aspect there is provided a method of treating cancer comprising administering to a subject in need thereof an HGF-MET agonist. Also provided is an HGF-Met agonist (e.g. a MET agonist antibody) for use in treating cancer.

Cancers particularly suitable to be treated according to the methods described herein include cancers of epithelial origin. Cancers particularly suitable to be treated according to the claimed methods are gastrointestinal cancers, for example: oesophageal cancer, stomach cancer, pancreatic cancer, liver cancer, gallbladder cancer, colorectal cancer and anal cancer.

Cancers associated with chronic inflammation are also particularly suited to being treated according to the provided methods. For example, liver cancer is associated with inflammation caused by hepatitis virus infection, stomach cancer is associated with inflammation caused by *Helico-* bacter pylori infection, and colorectal cancer is associated with intestinal inflammation. Accordingly, in certain embodiments, the method is a method of treating a cancer associated with chronic inflammation. In certain embodiments, the method is a method of treating liver cancer. In certain embodiments, the method is a method of treating stomach cancer.

As demonstrated herein, HGF-MET agonists are particularly effective at treating colorectal cancer. Therefore, in a preferred embodiment of the methods described herein, the method is a method of treating colorectal cancer.

Also provided is an HGF-Met agonist (e.g. a MET agonist antibody) for use in treating colorectal cancer.

Treatment of cancer, such as colorectal cancer, can be therapeutic or prophylactic treatment—that is, therapeutic treatment of subjects suffering from the condition, or prophylactic treatment of a subject so as to reduce their risk of contracting the condition or the severity of the condition once contracted. Therefore, in certain embodiments, treatment of cancer (such as colorectal cancer) is therapeutic. In certain embodiments, therapeutic treatment can be characterised by a decrease in the number of tumours or cancerous polyps in a subject that has been administered a MET agonist compared to before administration of the MET agonist. In certain embodiments, treatment of cancer (such as colorectal cancer) can be characterised by a decrease in the size or volume of tumours or cancerous polyps compared to before administration of the MET agonist. In certain embodiments, treatment can be characterised by decrease in the number, size and/or volume of tumours or cancerous polyps in the subject compared to a control subject that has not been administered a MET agonist.

In further embodiments of methods for treatment of colorectal cancer, therapeutic treatment may be further characterised by a decrease in the extent of colon fibrosis in the subject compared to before administration of the MET agonist. Means for determining the extent of fibrosis would be familiar to the skilled person and include, for example, determining the extent of collagen deposition in a representative biopsy.

In certain embodiments, treatment of cancer, for example colorectal cancer, may be prophylactic treatment. In certain embodiments, prophylactic treatment may be characterized by a decrease in the number of tumours or cancerous polyps in a subject (or population of subjects) that has been administered a Met agonist compared to a control subject (or population of control subjects) that has not been administered a MET agonist. In certain embodiments, prophylactic treatment of cancer, for example colorectal cancer, can be characterized by a decrease in the size or volume of tumours or cancerous polyps in a subject (or population of subjects) that has been administered a Met agonist compared to a control subject (or population of control subjects) that has not received a MET agonist.

In further embodiments, prophylactic treatment of colorectal cancer can be further characterised by a decrease in the extent of colon fibrosis in a subject (or population of subjects) that has been administered a MET agonist compared to a control subject (or population of control subjects) that has not been administered a MET agonist. Means for determining the extent of fibrosis would be familiar to the skilled person and include, for example, determining the extent of collagen deposition in a representative biopsy.

As will be appreciated by the skilled person, a "control subject" as used herein refers to a subject of comparable disease state to the subject being administered the HGF-MET agonist.

Method of Treating Colorectal Fibrosis

It is further surprisingly demonstrated herein that administration of an HGF-MET agonist (i.e. an agonist of MET that is not HGF) effectively treats colorectal fibrosis. A subject is particularly susceptible to colorectal fibrosis when suffering from intestinal inflammation.

Accordingly, in a further aspect is provided a method of treating colorectal fibrosis, comprising administering to a subject an HGF-MET agonist. Means for determining the extent of fibrosis in a subject would be familiar to the skilled person and include, for example, determining the extent of collagen deposition in a representative biopsy.

In certain embodiments of methods for treatment of colorectal fibrosis, treatment may be therapeutic treatment. In certain embodiments, therapeutic treatment can be characterised by a decrease in the extent of colon fibrosis in the subject compared to before administration of the MET agonist. In certain embodiments, therapeutic treatment can be characterised by a decrease in the extent of colon fibrosis in the subject compared to a control subject that has not been administered a MET agonist.

In certain embodiments, treatment of colorectal cancer can be prophylactic treatment. In certain embodiments, prophylactic treatment may be characterised by a decrease in the extent of colon fibrosis in a subject (or population of subjects) that has been administered a MET agonist compared to a control subject (or population of control subjects) that has not been administered a MET agonist.

As will be appreciated by the skilled person, a "control subject" as used herein refers to a subject of comparable disease state to the subject being administered the HGF-MET agonist.

Subject or Patient

As surprisingly demonstrated herein, administration of an HGF-MET agonist effectively treats cancer in a subject. It is further demonstrated that HGF-MET agonists are particularly effective at treating colorectal cancer, especially in patients predisposed or at risk of developing colorectal cancer.

Patients at increased risk of colorectal cancer are those who are more likely to develop colorectal cancer compared to an otherwise comparable healthy individual. Factors known to increase risk for colorectal cancer include, for example, age of >65 years, male gender, smoking, obesity, increased alcohol intake, increased red or processed meat intake. Methods described herein for treating colorectal cancer will be particularly effective at treating subjects having one or more of these risk factors.

Accordingly, in certain embodiments is provided a method of treating colorectal cancer comprising administering to a subject in need thereof an HGF-MET agonist, wherein the subject has been identified as at increased risk of colorectal cancer. In certain such embodiments, the subject has one or more risk factors selected from the group consisting of: age of >65 years, male gender, smoking, obesity, increased alcohol intake, increased red or processed meat intake.

Certain genetic conditions are also known risk factors for developing colorectal cancer. For example, hereditary non-polyposis colorectal cancer (HNPCC or Lynch syndrome), Gardner syndrome, and familial adenomatous polyposis (FAP) are syndromes known to increase risk of a subject developing colorectal cancer. Accordingly, in certain embodiments, the subject has a predisposition to developing colorectal cancer. In certain such embodiments, the subject has FAP, HNPCC or Gardner syndrome.

A significant risk factor for colorectal cancer and also for colorectal fibrosis is intestinal inflammation, in particular colorectal inflammation. Identifying subjects with colorectal inflammation would be within the ability of the skilled person. For example, colorectal inflammation can be identified visually via endoscope, histologically via biopsy, or by measuring a marker of colorectal inflammation such as faecal calprotectin. Colorectal inflammation is characteristic of patients suffering from inflammatory bowel disease, for example Crohn's Disease or ulcerative colitis.

As demonstrated in the Examples, methods described herein are particularly effective in subjects with colorectal inflammation. In a model of gut inflammation, a HGF-MET agonist effectively reduced both tumour burden and colorectal fibrosis.

Accordingly, in embodiments of all aspects of the claimed methods, the subject has been diagnosed with colorectal inflammation prior to administration of the HGF-MET agonist. In certain embodiments, the subject has inflammatory bowel disease (IBD), for example Crohn's Disease or ulcerative colitis.

Administration

It will be appreciated that, as used herein, administration of an HGF-MET agonist (for example an anti-MET agonist antibody) to a subject refers to administration of an effective amount of the agonist.

In certain embodiments, the HGF-MET agonist is administered at a dose in the range of from about 0.1 mg/kg to about 10 mg/kg per dose. In certain embodiments, the HGF-MET agonist is administered at a dose in the range of from 0.5 mg/kg to about 10 mg/kg. That is, a dose of about 0.5, 1, 2, 3, 4, 5, 6, 7, 8, 9 or 10 mg/kg. In certain preferred embodiments, the HGF-MET agonist is administered at a dose in the range of from about 1 mg/kg to about 5 mg/kg. In certain preferred embodiments, the HGF-MET agonist is administered at a dose of 1 mg/kg or 5 mg/kg.

Suitable routes for administration of the HGF-MET agonist (for example an anti-MET agonist antibody) to a subject would be familiar to the skilled person. Preferably the MET agonist is administered parenterally. In certain preferred embodiments, the HGF-MET agonist is administered subcutaneously (s.c.), intravenously (i.v.), intradermally (i.d.), intramuscularly (i.m.) or intraperitoneally (i.p.). In certain preferred embodiments, the HGF-MET agonist is a MET agonist antibody and is administered intravenously.

The HGF-MET agonist (for example anti-MET agonist antibody) can be administered according to a regimen that maintains an effective level of the agonist in the subject. The skilled person is familiar with suitable dosage regimens. For example, in certain embodiments, the HGF-MET agonist (e.g. MET agonist antibody) is administered according to a dosage regimen of at least once per week—that is, a dose is administered approximately every 7 days or more frequently. In certain embodiments, the HGF-MET agonist (e.g. MET agonist antibody) is administered 1-3 times a week (i.e. 1, 2 or 3 times a week). In certain preferred embodiments, the HGF-MET agonist (e.g. MET agonist antibody) is administered twice per week. In certain preferred embodiments, the HGF-MET agonist is a MET agonist antibody and is administered once per week or twice per week.

For the methods described herein, the HGF-MET agonist (e.g. MET agonist antibody) is administered for a period sufficient to achieve effective treatment. The skilled person is able to determine the necessary treatment period for any individual patient. In certain embodiments, the HGF-MET agonist (e.g. a MET agonist antibody) is administered for a treatment period of at least 1 week. In certain embodiments, the HGF-MET agonist (e.g. a MET agonist antibody) is administered for a treatment period of at least 2 weeks, at least 3 weeks, or at least 4 weeks. In certain embodiments, the HGF-MET agonist (e.g. a MET agonist antibody) is administered for a treatment period of at least 1 month, at least 2 months or at least 3 months. In certain preferred embodiments, the HGF-MET agonist is a MET agonist antibody and is administered for a treatment period of 3 months.

It will be appreciated that the HGF-MET agonist (e.g. a MET agonist antibody) may be administered according to any combination of the described doses, dosage regimens and treatment periods. For example, in certain embodiments, the HGF-MET agonist (e.g. a MET agonist antibody) may be administered according to a dosage regimen of twice per week, at a dose of from 1 mg/kg to 5 mg/kg, for a period of at least 3 months. Other embodiments of the methods explicitly include other combinations of the recited doses, dosage regimens and treatment periods.

HGF-MET Agonist

It is demonstrated in the Examples below that an HGF-Met agonist effectively treats cancer, in particular colorectal cancer. It is also demonstrated that an HGF-Met agonist effectively treats colorectal fibrosis. Therefore, in all aspects of the invention, an HGF-MET agonist is to be administered to a subject or patient to treat the indicated condition (i.e. cancer (e.g. colorectal cancer) or colorectal fibrosis). "HGF-MET agonist" and "MET agonist" are used interchangeably to refer to non-native agents that promote signalling via the MET protein—i.e. agents other than HGF that bind MET and increase MET signalling. Such agents may be small molecules, binding proteins such as antibodies or antigen binding fragments, aptamers or fusion proteins. A particular example of a MET agonist is an anti-MET agonist antibody.

Agonist activity on binding of MET by the MET agonists described herein is indicated by molecular and/or cellular responses that (at least partially) mimic the molecular and cellular responses induced upon HGF-MET binding.

Methods for determining MET agonism according to the invention, for example by MET agonist antibodies and antigen binding fragments, would be familiar to the skilled person. For example, MET agonism may be indicated by molecular responses such as phosphorylation of the MET receptor and/or cellular responses, for example those detectable in a cell scattering assay, an anti-apoptosis assay and/or a branching morphogenesis assay.

MET agonism may be determined by the level of phosphorylation of the MET receptor upon binding. In this context, a MET agonist antibody or antigen binding fragment, for example, causes auto-phosphorylation of MET in the absence of receptor-ligand binding—that is, binding of the antibody or antigen binding fragment to MET results in phosphorylation of MET in the absence of HGF. Phosphorylation of MET may be determined by assays known in the art, for example Western Blotting or phospho-MET ELISA (as described in Basilico et al., *J Clin Invest.* 124, 3172-3186, 2014, incorporated herein by reference).

MET agonism may alternatively be measured by induction of HGF-like cellular responses. MET agonism can be measured using assays such as a cell scattering assay, an anti-apoptosis assay and/or a branching morphogenesis assay. In this context, a MET agonist, for example an antibody or antigen binding fragment, induces a response in cellular assays such as these that resembles (at least partially) the response observed following exposure to HGF.

For example, a MET agonist (for example a MET agonist antibody) may increase cell scattering in response to the antibody compared to cells exposed to a control antibody (e.g. IgG1).

By way of further example, a MET agonist (for example a MET agonist antibody) may exhibit a protective potency against drug-induced apoptosis with an $EC_{50}$ of less than 32 nM. By way of further example, a MET agonist (for example a MET agonist antibody) may exhibit an $E_{max}$ cellular viability of greater than 20% compared to untreated cells.

By way of further example, a MET agonist (for example a MET agonist antibody) may increase the number of branches per spheroid in cell spheroid preparations exposed to the antibody or antigen binding fragment.

It is preferred that the MET agonists used according to the invention promote MET signalling to a magnitude of at least 70% of the natural ligand, HGF—that is, that the agonists are "full agonists". In certain embodiments, the MET agonists promote signalling to a magnitude of at least 80%, optionally at least 85%, at least 90%, at least 95% or at least 96%, at least 97%, at least 98%, at least 99% or at least 100% of HGF.

In certain embodiments, if MET agonism is determined using a phosphorylation assay, the MET agonist, e.g. a MET antibody, exhibits a potency for MET with an $EC_{50}$ of <1 nM. In certain embodiments, the MET agonist, e.g. a MET antibody, exhibits a potency for MET agonism of an $E_{MAX}$ of at least 80% (as a percentage of maximal HGF-induced activation).

In certain embodiments, if MET agonism is measured in a cell scattering assay, the MET agonist, for example a MET antibody or antigen binding fragment, induces an increase in cell scattering at least equivalent to 0.1 nM homologous HGF when the antibody concentration is 0.1-1 nM.

In certain embodiments, if MET agonism is measured in an anti-apoptosis assay, the MET agonist (for example a MET antibody or fragment thereof) exhibits an $EC_{50}$ no more than 1.1× that of HGF.

In certain embodiments, if MET agonism is measured in an anti-apoptosis assay, the MET agonist (for example a MET antibody or fragment thereof) exhibits an $E_{max}$ cellular viability of greater than 90% that observed for HGF.

In certain embodiments, if MET agonism is measured in a branching morphogenesis assay, cells treated with the MET agonist (e.g. a MET antibody or antigen binding fragment) exhibit greater than 90% of the number of branches per spheroid induced by the same (non-zero) concentration of HGF.

HGF-MET agonists particularly preferred in all aspects of the invention are anti-MET agonist antibodies, also referred to herein as "MET agonist antibodies", "agonist antibodies" and grammatical variations thereof. In other words, MET agonist antibodies (or antigen binding fragments thereof) for use according to the invention bind MET and promote cellular signalling via MET.

As demonstrated in the Examples, 71 D6 is a MET agonist antibody that effectively treats cancer (in particular colorectal cancer) and also colorectal fibrosis. 71 D6 binds an epitope on the SEMA domain of MET, in particular an epitope on blade 4-5 of the SEMA p-propeller. MET agonists binding an epitope on the SEMA domain of MET, in particular blade 4-5 of the SEMA p-propeller have therefore been demonstrated to lead to effective treatment of (colorectal) cancer. Antibody 71G2 has similar effects to 71 D6 and also binds the SEMA domain of MET, in particular blade 4-5 of the SEMA β-propeller.

Thus, in certain embodiments is provided a method of treating cancer (for example colorectal cancer), or a method of treating colorectal fibrosis, comprising administering a MET agonist antibody or antigen binding fragment thereof, wherein the antibody or antigen binding fragment binds an epitope in the SEMA domain of MET. In certain preferred embodiments, the antibodies or fragments thereof binds an epitope located on a blade of the SEMA β-propeller. In certain embodiments, the epitope is located on blade 4 or 5 of SEMA β-propeller. In certain preferred embodiments, the antibody or antigen binding fragment binds an epitope located between amino acids 314-372 of MET.

As shown in the Examples, MET agonist antibodies binding the SEMA domain of MET, including 71D6 and 71G2, have been shown to bind to an epitope on MET that includes residue Ile367 and residue Asp371. Mutation at either of these residues impairs binding of the antibodies to MET, with mutation of both residues completely abrogating binding.

Therefore, in certain preferred embodiments is provided a method of treating cancer (e.g. colorectal cancer), or a method of treating colorectal fibrosis, comprising administering a MET agonist antibody or antigen binding fragment thereof, wherein the antibody or antigen binding fragment recognises an epitope comprising the amino acid residue Ile367. In certain preferred embodiments is provided a method of treating cancer (e.g. colorectal cancer), or a method of treating colorectal fibrosis, comprising administering a MET agonist antibody or antigen binding fragment thereof, wherein the antibody or antigen binding fragment recognises an epitope comprising the amino acid residue Asp371.

In certain preferred embodiments, the antibody or antigen binding fragment binds an epitope comprising the amino acid residues Ile367 and Asp372 of MET.

As well as MET agonist antibodies binding the SEMA domain, also described herein are agonist antibodies binding other MET domains. For example, 71G3 binds an epitope on the PSI domain of MET. As demonstrated in the Examples, antibody 71G3 exhibits similar potency to 71 D6 for reducing intestinal inflammation. 71G3 will therefore also be effective at treating colorectal cancer in a manner similar to 71 D6. Similarly, 71G3 will also be effective at treating colorectal fibrosis in a manner similar to 71 D6.

Thus, in certain embodiments is provided a method of treating cancer (for example colorectal cancer), or a method of treating colorectal fibrosis, comprising administering a MET agonist antibody or antigen binding fragment thereof, wherein the antibody or antigen binding fragment binds an epitope in the PSI domain of MET. In certain preferred embodiments, the antibody or antigen binding fragment binds an epitope located between amino acids 546 and 562 of MET.

As shown in the Examples, MET agonist antibodies binding the PSI domain of MET, including 71G3, have been shown to bind to an epitope on MET that includes residue Thr555. Mutation at this residue completely abrogated binding of the PSI-binding agonist antibodies to MET.

Therefore, in certain preferred embodiments is provided a method of treating cancer (e.g. colorectal cancer), or a method of treating colorectal fibrosis, comprising administering a MET agonist antibody or antigen binding fragment thereof, wherein the antibody or antigen binding fragment recognises an epitope comprising the amino acid residue Thr555.

Examples of MET agonist antibodies particularly suitable for use in treating cancer (for example colorectal cancer), or for use in treating colorectal fibrosis, are those having a combination of CDRs corresponding to the CDRs of an anti-MET antibody described herein. Therefore, in certain embodiments, the antibody or antigen binding fragment comprises a combination of VH and VL CDR sequences corresponding to a combination of VH CDRs from a MET agonist antibody described in Table 3 and the corresponding combination of VL CDRs for the same antibody in Table 4.

In certain such embodiments, the antibody or antigen binding fragment comprises a combination of CDRs corresponding to a combination of VH CDRs from a MET agonist antibody described in Table 3 and the corresponding combination of VL CDRs for the same antibody in Table 4, and further having VH and VL domains with at least 90%, optionally at least 95%, optionally at least 99%, preferably 100% sequence identity with the corresponding VH and VL sequences of the antibody described in Table 6. By way of clarification, in such embodiments the permitted variation in percentage identity of the VH and VL domain sequences is not in the CDR regions.

As demonstrated in the Examples, 71 D6 is a MET agonist antibody that is a "full agonist" of MET. That is, on binding of 71D6 to MET, the signalling response is similar to or even exceeds the response to binding of the native HGF ligand. 71 D6 is demonstrated to effectively treat (colorectal) cancer. Therefore in certain preferred embodiments is provided a method of treating cancer (e.g. colorectal cancer) comprising administering an HGF-MET agonist that is a full agonist—that is, an agonist that upon binding promotes MET signalling to an extent of at least 70% of MET signalling upon HGF binding. Examples for measuring MET agonism and examples of the effects of full agonists have already been described herein.

Examples of MET full agonists, such as anti-MET antibodies that are full agonists include 71 D6 and 71G2, as demonstrated in the Examples. Therefore in particularly preferred embodiments is provided a method of treating cancer (e.g. colorectal cancer), or a method of treating colorectal fibrosis, comprising administering a MET agonist antibody or antigen binding fragment thereof that is a full agonist of MET. In preferred such embodiments, the antibody or fragment comprises a combination of CDRs having the corresponding CDR sequences of antibody 71 D6 (SEQ ID Nos: 30, 32, 34, 107, 109, and 111), of antibody 71G2 (SEQ ID NOs: 44, 46, 48, 121, 123, and 125), or of antibody 71G3 (SEQ ID Nos: 9, 11, 13, 86, 88, and 90).

In preferred embodiments of all aspects, the MET agonist is a MET agonist antibody or antigen binding fragment thereof having HCDR1 of [71 D6] SEQ ID NO: 30, HCDR2 of SEQ ID NO: 32, HCDR3 of SEQ ID NO: 34, LCDR1 of SEQ ID NO: 107, LCDR2 of SEQ ID NO: 109, and LCDR3 of SEQ ID NO: 111. In preferred such embodiments, the antibody or antigen binding fragment comprises: a VH domain comprising SEQ ID NO: 163 or a sequence at least 90% identical thereto, optionally at least 95%, at least 98% or at least 99% identical thereto; and a VL domain comprising SEQ ID NO: 164 or a sequence at least 95% thereto optionally at least 98% or at least 99% identical thereto. By way of clarification, in such embodiments the permitted variation in percentage identity of the VH and VL domain sequences is not in the CDR regions.

MET agonist antibodies for use as described herein can take various different embodiments in which both a VH domain and a VL domain are present. The term "antibody" herein is used in the broadest sense and encompasses, but is not limited to, monoclonal antibodies (including full length monoclonal antibodies), polyclonal antibodies, multispecific antibodies (e.g., bispecific antibodies), so long as they exhibit the appropriate immunological specificity for a human MET protein and for a mouse MET protein. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

"Antibody fragments" comprise a portion of a full length antibody, generally the antigen binding or variable domain thereof. Examples of antibody fragments include Fab, Fab', F(ab')2, bi-specific Fab's, and Fv fragments, diabodies, linear antibodies, single-chain antibody molecules, a single chain variable fragment (scFv) and multispecific antibodies formed from antibody fragments (see Holliger and Hudson, Nature Biotechnol. 23:1126-1136, 2005, the contents of which are incorporated herein by reference).

In preferred embodiments of all aspects provided herein, the MET agonist antibody or antigen-binding fragment thereof is bivalent.

In non-limiting embodiments, the MET antibodies provided herein may comprise CH1 domains and/or CL domains, the amino acid sequence of which is fully or substantially human. Therefore, one or more or any combination of the CH1 domain, hinge region, CH2 domain, CH3 domain and CL domain (and CH4 domain if present) may be fully or substantially human with respect to its amino acid sequence. Such antibodies may be of any human isotype, for example IgG1 or IgG4.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. Such antibodies may be of any human isotype, with human IgG4 and IgG1 being particularly preferred.

MET agonist antibodies may also comprise constant domains of "human" sequence which have been altered, by one or more amino acid additions, deletions or substitutions with respect to the human sequence, excepting those embodiments where the presence of a "fully human" hinge region is expressly required. The presence of a "fully human" hinge region in the MET antibodies of the invention may be beneficial both to minimise immunogenicity and to optimise stability of the antibody.

The MET agonist antibodies may be of any isotype, for example IgA, IgD, IgE IgG, or IgM. In preferred embodiments, the antibodies are of the IgG type, for example IgG1, IgG2a and b, IgG3 or IgG4. IgG1 and IgG4 are particularly preferred. Within each of these sub-classes it is permitted to make one or more amino acid substitutions, insertions or deletions within the Fc portion, or to make other structural modifications, for example to enhance or reduce Fc-dependent functionalities.

In non-limiting embodiments, it is contemplated that one or more amino acid substitutions, insertions or deletions may be made within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the MET antibody, it may be desirable to modify the antibody of the invention with respect to its binding properties to Fc receptors, for example to modulate effector function.

In certain embodiments, the MET antibodies may comprise an Fc region of a given antibody isotype, for example human IgG1, which is modified in order to reduce or substantially eliminate one or more antibody effector functions naturally associated with that antibody isotype. In non-limiting embodiments, the MET antibody may be substantially devoid of any antibody effector functions. In this context, "antibody effector functions" include one or more or all of antibody-dependent cellular cytotoxicity (ADCC), complement-dependent cytotoxicity (CDC) and antibody-dependent cellular phagocytosis (ADCP).

The amino acid sequence of the Fc portion of the MET antibody may contain one or more mutations, such as amino acid substitutions, deletions or insertions, which have the effect of reducing one or more antibody effector functions (in comparison to a wild type counterpart antibody not having said mutation). Several such mutations are known in the art of antibody engineering. Non-limiting examples, suitable for inclusion in the MET antibodies described herein, include the following mutations in the Fc domain of human IgG4 or human IgG1: N297A, N297Q, LALA (L234A, L235A), AAA (L234A, L235A, G237A) or D265A (amino acid residues numbering according to the EU numbering system in human IgG1).

In certain embodiments of all aspects of the invention, therefore, the anti-MET agonist antibody is an agonist antibody of both human MET and mouse MET.

Pharmaceutical Compositions

Also provided in accordance with the invention are pharmaceutical compositions for use in the methods described herein. Therefore in a further aspect of the invention is provided a pharmaceutical composition comprising an HGF-MET agonist, for example an anti-MET agonist antibody, and a pharmaceutically acceptable excipient or carrier for use in a method according to the invention. Suitable pharmaceutically acceptable carriers and excipients would be familiar to the skilled person. Examples of pharmaceutically acceptable carriers and excipients suitable for inclusion in pharmaceutical compositions of the invention include sodium citrate, glycine, polysorbate (e.g. polysorbate 80) and saline solution.

In certain embodiments, the MET agonist, for example anti-MET agonist antibody, is administered to the subject parenterally, preferably intravenously (i.v.). In certain embodiments the MET agonist, for example anti-MET agonist antibody, is administered as a continuous i.v. infusion until the desired dose is achieved.

EXAMPLES

The invention will be further understood with reference to the following non-limiting experimental examples.

Example 1: Generation of Ant-MET Agonist Antibodies—Immunization of Llamas

Immunizations of llamas and harvesting of peripheral blood lymphocytes (PBLs) as well as the subsequent extraction of RNA and amplification of antibody fragments were performed as described (De Haard et al., J. Bact. 187:4531-4541, 2005). Two adult llamas (*Lama glama*) were immunized by intramuscular injection of a chimeric protein consisting of the extracellular domain (ECD) of human MET fused to the Fc portion of human IgG1 (MET-Fc; R&D Systems). Each llama received one injection per week for six weeks, for a total of six injections. Each injection consisted in 0.2 mg protein in Freund's Incomplete Adjuvant in the neck divided over two spots.

Blood samples of 10 ml were collected pre- and post-immunization to investigate the immune response. Approximately one week after the last immunization, 400 ml of blood was collected and PBLs were obtained using the Ficoll-Paque method. Total RNA was extracted by the phenol-guanidine thiocyanate method (Chomczynski et al., Anal. Biochem. 162:156-159, 1987) and used as template for random cDNA synthesis using the SuperScript™ III First-Strand Synthesis System kit (Life Technologies). Amplification of the cDNAs encoding the VH-CH1 regions of llama IgG1 and VL-CL domains (K and A) and subcloning into the phagemid vector pCB3 was performed as described (de Haard et al., J Biol Chem. 274:18218-18230, 1999). The *E. coli* strain TG1 (Netherland Culture Collection of Bacteria) was transformed using recombinant phagemids to generate 4 different Fab-expressing phage libraries (one A and one K library per immunized llama). Diversity was in the range of 103-109.

The immune response to the antigen was investigated by ELISA. To this end, we obtained the ECDs of human MET (UniProtKB #P08581; aa 1-932) and of mouse MET (UniProtKB #P16056.1; aa 1-931) by standard protein engineering techniques. Human or mouse MET ECD recombinant protein was immobilized in solid phase (100 ng/well in a 96-well plate) and exposed to serial dilutions of sera from llamas before (day 0) or after (day 45) immunization. Binding was revealed using a mouse anti-llama IgG1 (Daley et al., Clin. Vaccine Immunol. 12, 2005) and a HRP-conjugated donkey anti-mouse antibody (Jackson Laboratories). Both llamas displayed an immune response against human MET ECD. Consistent with the notion that the extracellular portion of human MET displays 87% homology with its mouse orthologue, a fairly good extent of cross-reactivity was also observed with mouse MET ECD.

Example 2: Selections and Screenings of Fabs Binding to Both Human and Mouse MET Fab-expressing phages from the libraries described above were produced according to standard phage display protocols. For selection, phages were first adsorbed to immobilized recombinant human MET ECD, washed, and then eluted using trypsin. After two cycles of selection with human MET ECD, two other cycles were performed in the same fashion using mouse MET ECD. In parallel, we also selected phages alternating a human MET ECD cycle with a mouse MET ECD cycle, for a total of four cycles. Phages selected by the two approaches were pooled together and then used to infect TG1 *E. coli*. Individual colonies were isolated and secretion of Fabs was induced using IPTG (Fermentas). The Fab-containing periplasmic fraction of bacteria was collected and tested for its ability to bind human and mouse MET ECD by Surface Plasmon Resonance (SPR). Human or mouse MET ECD was immobilized on a CM-5 chip using amine coupling in sodium acetate buffer (GE Healthcare). The Fab-containing periplasmic extracts were loaded into a BIACORE 3000 apparatus (GE Healthcare) with a flow rate of 30 μl/min. The Fab off-rates (korr) were measured over a two minute period. Binding of Fabs to human and mouse MET was further characterized by ELISA using MET ECD in solid phase and periplasmic crude extract in solution. Because Fabs are engineered with a MYC flag, binding was revealed using HRP-conjugated anti-MYC antibodies (ImTec Diagnostics).

Fabs that bound to both human and mouse MET in both SPR and ELISA were selected and their corresponding phages were sequenced (LGC Genomics). Cross-reactive Fab sequences were divided into families based on VH CDR3 sequence length and content. VH families were given an internal number not based on IMTG (International Immunogenetics Information System) nomenclature. Altogether, we could identify 11 different human/mouse cross-reactive Fabs belonging to 8 VH families. The CDR and FR sequences of heavy chain variable regions are shown in Table 3. The CDR and FR sequences of light chain variable regions are shown in Table 4. The full amino acid sequences of heavy chain and light chain variable regions are shown in Table 5. The full DNA sequences of heavy chain and light chain variable regions are shown in Table 6.

TABLE 3

Framework regions and CDR sequences for VH domains of Fabs binding to both human and mouse MET.

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 76H10 | QLQLVESGGGLVQPGGSLRVSCTASGFTFN | 1 | TYYMT | 2 | WVRQAPGKGLEWVS | 3 | DINSGGTYYADSVKG | 4 | RFTISRDNAKNTLYLQMNSLKPEDTALYYCVR | 5 | VRIWPVGYDY | 6 | WGQGTQVTVSS | 7 |
| 71G3 | QVQLVESGGGLVQPGGSLRVSCAASGFTFS | 8 | TYYMS | 9 | WVRQAPGKGLEWVS | 10 | DIRTDGGTYYADSVKG | 11 | RFTMSRDNAKNTLYLQMNSLKPEDTALYYCAR | 12 | TRIFPSGYDY | 13 | WGQGTQVTVSS | 14 |
| 71C3 | QLQLVESGGGLVQPGGSLRLSCAASGFTFS | 15 | SHAMS | 16 | WVRQAPGKGLEWVS | 17 | AINSGGSTSYADSVKG | 18 | RFTISRDNAKNTLYLQMNSLKPEDTAVYYCAK | 19 | ELRFDLARYTDYEAWDY | 20 | WGQGTQVTVSS | 21 |
| 71D4 | ELQLVESGGGLVQPGGSLRLSCAASGFTFS | 22 | GYGMS | 23 | WVRQAPGKGLEWVS | 24 | DINSGGSTSYADSVKG | 25 | RFTISRDNAKNTLYLQMNSLKPEDTAVYYCAK | 26 | DMRLYLARYNDYEAWDY | 27 | WGQGTQVTVSS | 28 |
| 71D6 | ELQLVESGGGLVQPGGSLRLSCAASGFTFS | 29 | SYGMS | 30 | WVRQAPGKGLEWVS | 31 | AINSYGSTSYADSVKG | 32 | RFTISRDNAKNTLYLQMNSLKPEDTAVYYCAK | 33 | EVRADLSRYNDYESYDY | 34 | WGQGTQVTVSS | 35 |
| 71A3 | EVQLVESGGGLVQPGGSLRLSCAASGFSFK | 36 | DYDIT | 37 | WVRQAPGKGLEWVS | 38 | TITSRSGSTSYVDSVKG | 39 | RFTISGDNAKNTLYLQMNSLKPEDTAVYYCAK | 40 | VYATTWDVGPLGYGMDY | 41 | WGKGTLVTVSS | 42 |

TABLE 4

Framework regions and CDR sequences for VL domains of Fabs binding to both human and mouse MET.

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 76H10 | QAWTQEPSLSVSPGGTVTLTC | | GLSSGSVTTSNYPG | 78 | WFQQTPGQAPRTLIY | 79 | NTNNRHS | 80 | GVPSRFSGSISGNKAALTITGAQPEDEADYYC | 81 | SLYTGSYTTV | 82 | FGGGTHLTVL | 83 | 84 |
| 71G3 | QAWTQEPSLSVSPGGTVTLTC | | GLSSGSVTTSNYPG | 85 | WFQQTPGQAPRTLIY | 86 | NTNSRHS | 87 | GVPSRFSGSISGNKAALTIMGAQPEDEADYYC | 88 | SLYPGSTTV | 89 | FGGGTHLTVL | 90 | 91 |
| 71C3 | SYELTQPSALSVTLGQTAKITC | | QGGSLGSSYAH | 92 | WYQQKPGQAPVLVIY | 93 | DDDSRPS | 94 | GIPERFSGSSSGGTATLTISGAQAEDEGDYYC | 95 | QSADSSGNAAV | 96 | FGGGTHLTVL | 97 | 98 |
| 71D4 | SSALTQPSALSVTLGQTAKITC | | QGGSLGSSYAH | 99 | WYQQKPGQAPVLVIY | 100 | DDDSRPS | 101 | GIPERFSGSSSGGTATLTISGAQAEDEGDYYC | 102 | QSADSSGNAAV | 103 | FGGGTHLTVL | 104 | 105 |
| 71D6 | QPVLNQPSALSVTLGQTAKITC | | QGGSLGARYAH | 106 | WYQQKPGQAPVLVIY | 107 | DDDSRPS | 108 | GIPERFSGSSSGGTATLTISGAQAEDEGDYYC | 109 | QSADSSGSV | 110 | FGGGTHLTVL | 111 | 112 |
| 71A3 | SYELTQPSALSVTLGQTAKITC | | QGGSLGSSYAH | 113 | WYQQKPGQAPVLVIY | 114 | DDDSRPS | 115 | GIPERFSGSSSGTATLTISGAQAEDEGDYYC | 116 | QSADSSGNAAV | 117 | FGGGTHLTVL | 118 | 119 |
| 71G2 | SSALTQPSALSVSLGQTARITC | | QGGSLGSSYAH | 120 | WYQQKPGQAPVLVIY | 121 | GDDSRPS | 122 | GIPERFSGSSSGTATLTISGAQAEDEDDYYC | 123 | QSTDSSGNTV | 124 | FGGGTRLTVL | 125 | 126 |
| 76G7 | QAGLTQPPSVSGSPGKTVTISC | | AGNSSDVGYGNYVS | 127 | WYQQFPGMAPKLLIY | 128 | LVNKRAS | 129 | GITDRFSGSKSGNTASLTISGLQSEDEADYYC | 130 | ASYTGSNNIV | 131 | FGGGTHLTVL | 132 | 133 |
| 71G12 | EIVLTQSPSSVTASVGKVTINC | | KSSQSVFIASNQKTYLN | 134 | WYQQRPGQSPRLVIS | 135 | YASTRES | 136 | GIPDRFSGSGSTTDFTLTISSVQP | 137 | QQAYSHPT | 138 | FGQGTKVELK | 139 | 140 |

TABLE 4-continued

Framework regions and CDR sequences for VL domains of Fabs binding to both human and mouse MET.

| Clone | FR1 | SEQ ID NO. | CDR1 | SEQ ID NO. | FR2 | SEQ ID NO. | CDR2 | SEQ ID NO. | FR3 | SEQ ID NO. | CDR3 | SEQ ID NO. | FR4 | SEQ ID NO. |
|---|---|---|---|---|---|---|---|---|---|---|---|---|---|---|
| 74C8 | QTWTQEPSLSVSPGGTVTLTC | 141 | GLSSGSVTTSNYPG | 142 | WFQQTPGQAPRTLIY | 143 | NTNSRHS | 144 | GVPSRFSGSISGNKAALTITGAQPEDEAVYYC | 145 | SLYPGSYTNV | 146 | FGGGTHLTVL | 147 |
| 72F8 | QSALTQPPSLSASPGSSVRLTC | 148 | TLSSGNNIGSYDIS | 149 | WYQQKAGSPPRYLLN | 150 | YYTDSRKHQDS | 151 | GVPSRFSGSKDASANAGLLLISGLQPEDEADYYC | 152 | SAYKSGSYRWV | 153 | FGGGTHVTVL | 154 |

TABLE 5

Variable domain amino acid sequences of Fabs binding to both human and mouse MET.

| CLONE | VH | SEQ ID NO. | VL | SEQ ID NO. |
|---|---|---|---|---|
| 76H10 | QLQLVESGGGLVQPGGSLRVSCTASGFTFNTYYMTWVRQAPGKGLEWVSDINSGGGTYYADSVKGRFTISRDNAKNTLYLQMNSLKPEDTALYYCVRVRIWPVGYDYWGQGTQVTVSS | 155 | QAWTQEPSLSVSPGGTVTLTCGLSSGSVTTSNYPGWFQQTPGQAPRTLIYNTNNRHSGVPSRFSGSISGNKAALTITGAQPEDEADYYCSLYTGSYTTVFGGGTHLTVL | 156 |
| 71G3 | QVQLVESGGGLVQPGGSLRVSCAASGFTFSTYYMSWVRQAPGKGLEWVSDIRTDGGTYYADSVKGRFTMSRDNAKNTLYLQMNSLKPEDTALYYCARTRIFPSGYDYWGQGTQVTVSS | 157 | QAWTQEPSLSVSPGGTVTLTCGLSSGSVTTSNYPGWFQQTPGQAPRTLIYNTNSRHSGVPSRFSGSISGNKAALTIMGAQPEDEADYYCSLYPGSTTVFGGGTHLTVL | 158 |
| 71C3 | QLQLVESGGGLVQPGGSLRLSCAASGFTFSSHAMSWVRQAPGKGLEWVSAINSGGGTSYADSVKGRFTISRDNAKNTLYLQMNSLKPEDTAVYYCAKELRFDLARYTDYEAWDYWGQGTQVTVSS | 159 | SYELTQPSALSVTLGQTAKITCQGGSLGSSYAHWYQQKPGQAPVLVIYDDDSRPSGIPERFSGSSSGGTATLTISGAQAEDEGDYYCQSADSSGNAAVFGGGTHLTVL | 160 |
| 71D4 | ELQLVESGGGLVQPGGSLRLSCAASGFTFSGYMSWVRQAPGKGLEWVSDINSGGGTSYADSVKGRFTISRDNAKNTLYLQMNSLKPEDTAVYYCAKDMRLYLARYNDYEAWDYWGQGTQVTVSS | 161 | SSALTQPSALSVTLGQTAKITCQGGSLGSSYAHWYQQKPGQAPVLVIYDDDSRPSGIPERFSGSSSGGTATLTISGAQAEDEGDYYCQSADSSGNAAVFGGGTHLTVL | 162 |
| 71D6 | ELQLVESGGGLVQPGGSLRLSCAASGFTFSSYGMSWVRQAPGKGLEWVSAINSYGGSTSYADSVKGRFTISRDNAKNTLYLQMNSLKPEDTAVYYCAKEVRADLSRYNDYESYDYWGQGTQVTVSS | 163 | QPVLNQPSALSVTLGQTAKITCQGGSLGARYAHWYQQKPGQAPVLVIYDDDSRPSGIPERFSGSSSGGTATLTISGAQAEDEGDYYCQSADSSGSVFGGGTHLTVL | 164 |
| 71A3 | EVQLVESGGGLVQPGGSLRLSCAASGFSFKDYDITWVRQAPGKGLEWVSTITSRSGSTSYVDSVKGRFTISGDNAKNTLYLQMNSLKPEDTAVYYCAKVYATTWDVGPLGYGMDYWGKGTLVTVSS | 165 | SYELTQPSALSVTLGQTAKITCQGGSLGSSYAHWYQQKPGQAPVLVIYDDDSRPSGIPERFSGSSSGGTATLTISGAQAEDEGDYYCQSADSSGNAAVFGGGTHLTVL | 166 |
| 71G2 | EVQLQESGGGLVQPGGSLRLSCAASGFTFSIYDMSWVRQAPGKGLEWVSTINSDGSSTSYVDSVKGRFTISRDNAKNTLYLQMNSLKPEDTAVYYCAKVYGSTWDVGPMGYGMDYWGKGTLVTVSS | 167 | SSALTQPSALSVSLGQTARITCQGGSLGSSYAHWYQQKPGQAPVLVIYDDDSRPSGIPERFSGSSSGGTATLTISGAQAEDEDDYYCQSTDSSGNTVFGGGTRLTVL | 168 |
| 76G7 | QVQLVESGGNLVQPGGSLRLSCAASGFTFSNYYMSWVRQAPGKGLEWVSDIYSDGSTTWYSDSVKGRFTISRDNAKNTLSLQMNSLKSEDTAVYYCARVKIYPGGYDAWGQGTQVTVSS | 169 | QAGLTQPPSVSGSPGKTVTISCAGNSSDVGYGNYVSWYQQFPGMAPKLLIYLVNKRASGITDRFSGSKSGNTASLTISGLQSEDEADYYCASYTGSNNIVFGGGTHLTVL | 170 |
| 71G12 | QVQLQESGGDLVQPGGSLRVSCVVSGFTFSRYYMSWVRQAPGKGLEWVSSIDSYGYSTYYTDSVKGRFTISRDNAKNTLYLQMNSLKPEDTALYYCARAKTTWSYDYWGQGTQVTVSS | 171 | EIVLTQSPSSVTASVGGKVTINCKSSQSVFIASNQKTYLNWYQQRPGQSPRLVISYASTRESGIPDRFSGSGSTTDFTLTISSVQPEDAAVYYCQQAYSHPTFGQGTKVELK | 172 |
| 74C8 | EVQLVESGGGLVQPGGSLRLSCAASGFTFRNYHMSWVRQVPGKGFEWISDINSAGGSTYYADSVKGRFTISRDNAKNTLYLEMNSLKPEDTALYYCARVNVWGVNYWGKGTLVSVSS | 173 | QTVVTQEPSLSVSPGGTVTLTCGLSSGSVTTSNYPGWFQQTPGQAPRTLIYNTNSRHSGVPSRFSGSISGNKAALTITGAQPEDEADYYCSLYPGSYTNVFGGGTHLTVL | 174 |

TABLE 5-continued

Variable domain amino acid sequences of Fabs binding to both human and mouse MET.

| CLONE | VH | SEQ ID NO. | VL | SEQ ID NO. |
|---|---|---|---|---|
| 72F8 | ELQLVESGGGLVQPGGSLR LSCAASGFTFSNYVMSWVR QAPGKGLEWVSDTNSGGST SYADSVKGRFTISRDNAKN TLYLQMNSLKPEDTALYYC ARSFFYGMNYWGKGTQVTV SS | 175 | QSALTQPPSLSASPGSSVR LTCTLSSGNNIGSYDISWY QQKAGSPPRYLLNYYTDSR KHQDSGVPSRFSGSKDASA NAGLLLISGLQPEDEADYY CSAYKSGSYRWVFGGGTHV TVL | 176 |

TABLE 6

Variable domain nucleotide sequences of Fabs binding to both human and mouse MET.

| Clone | VH | SEQ ID NO. | VL | SEQ ID NO. |
|---|---|---|---|---|
| 76H10 | CAGTTGCAGCTGGTGGAGTCTGGGGGAGGCTTGGTGCAGCCTGGGGGGTCTCTGAGAGTTTCCTGTACAGCCTCTGGATTCACCTTCAATACCTACTACATGACCTGGGTCCGCCAGGCTCCAGGGAAGGGGCTCGAGTGGGTCTCAGATATTAATAGTGGTGGTGGTACATACTATGCAGACTCCGTGAAGGGCCGATTCACCATCTCCAGAGACAACGCCAAGAACACGCTATATCTGCAAATGAACAGCCTGAAACCTGAGGACACGGCCCTGTATTACTGTGTAAGAGTTCGTATTTGGCCAGTGGGATATGACTACTGGGGCCAGGGGACCCAGGTCACCGTTTCCTCA | 177 | CAGGCTGTGGTGACCCAGGAGCCGTCCCTGTCAGTGTCTCCAGGAGGGACGGTCACACTCACCTGCGGCCTCAGCTCTGGGTCTGTCACTACCAGTAACTACCCTGGTTGGTTCCAGCAGACCCGGGCCAGGCTCCACGCACTCTTATCTACAACACAAACAACCGCCACTCTGGGGTCCCCAGTCGCTTCTCCGGATCCATCTCTGGGAACAAAGCCGCCCTCACCATCACGGGGGCCCAGCCCGAGGACGAGGCCGACTATTACTGTTCTCTATATACTGGCAGTTACACTACTGTGTTCGGCGGAGGGACCCATCTGACCGTCCTG | 178 |
| 71G3 | CAGGTGCAGCTCGTGGAGTCTGGGGGAGGCTTGGTGCAGCCTGGGGGGTCTCTGAGAGTCTCCTGTGCAGCCTCTGGATTCACCTTCAGTACCTACTACATGAGCTGGGTCCGCCAGGCTCCAGGGAAGGGGCTCGAGTGGGTCTCAGATATTCGTACTGATGGTGGCACATACTATGCAGACTCCGTGAAGGGCCGATTCACCATGTCCAGAGACAACGCCAAGAACACGCTGTATCTACAAATGAACAGCCTGAAACCTGAGGACACGGCCCTGTATTACTGTGCAAGAACTGAATTTTCCCCTCGGGGTATGACTACTGGGGCCAGGGGACCCAGGTCACCGTCTCCTCA | 179 | CAGGCTGTGGTGACCCAGGAGCCGTCCCTGTCAGTGTCTCCAGGAGGGACGGTCACACTCACCTGCGGCCTCAGCTCTGGGTCTGTCACTACCAGTAACTACCCTGGTTGGTTCCAGCAGACCCAGGCCAGGCTCCGCGCACTCTTATCTACAACACAAACAGCCGCCACTCTGGGGTCCCCAGTCGCTTCTCCGGATCCATCTCTGGGAACAAAGCCGCCCTCACCATCATGGGGGCCCAGCCCGAGGACGAGGCCGACTATTACTGTTCTCTGTACCCTGGTAGTACCACTGTGTTCGGCGAGGGACCCATCTGACCGTCCTG | 180 |
| 71C3 | CAGTTGCAGCTGGTGGAGTCTGGGGGAGGCTTGGTGCAGCCTGGGGGGTCTCTGAGACTCTCCTGTGCAGCCTCTGGATTCACCTTCAGTAGCCATGCCATGAGCTGGGTCCGCCAGGCTCCAGGGAAGGGGCTCGAGTGGGTCTCAGCTATTAATAGTGGTGGTGGTAGCACAAGCTATGCAGACTCCGTGAAGGGCCGATTCACCATCTCCAGAGACAACGCCAAGAACACGCTGTACCTGCAAATGAACAGCCTGAAACCTGAGGACACGGCCGTGTATTACTGTGCAAAAGAGCTGAGATTCGACCTAGCAAGGTATACCGACTATGAGGCCTGGGACTACTGGGGCCAGGGGACCCAGGTCACCGTCTCCTCA | 181 | TCCTATGAGCTGACTCAGCCCTCCGCGCTGTCCGTAACCTTGGGACAGACGGCCAAGATCACCTGCCAAGGTGGCAGCTTAGGTAGCAGTTATGCTCACTGGTACCAGCAGAAGCCAGGCCAGGCCCCTGTGCTGGTCATCTATGATGATGACAGCAGGCCCTCAGGGATCCCTGAGCGGTTCTCTGGCTCCAGCTCTGGGGGCACAGCCACCCTGACCATCAGCGGGGCCCAGGCCGAGGACGAGGGTGACTATTACTGTCAGTCAGCAGACAGCAGTGGTAATGCTGCTGTGTTCGGCGGAGGGACCCATCTGACCGTCCTG | 182 |
| 71D4 | GAGTTGCAGCTGGTGGAGTCTGGGGGAGGCTTGGTGCAGCCTGGGGGGTCTCTGAGACTCTCCTGTGCAGCCTCTGGATTCACCTTCAGTGGCTATGGCATGAGCTGGGTCCGCCAGGCTCCAGGGAAGGGGCTCGAGTGGGTCTCAGATATTAATAGTGGTGGTGGTAGCACAAGCTATGCAGACTCCGTGAAGGGCCGATTCACCATCTCCAGAGACAACGCCAAGAACACGCTGTATCTGCAAATGAACAGCCTGAAACCTGAGGACACGGCCGTGTATTACTGTGCAAAAGATATGAGATTATACCTAGCAAGGTATAACGACTATGAGGCCTGGGACTACTGGGGCCAGGGGACCCAGGTCACCGTCTCCTCA | 183 | TCCTCTGCACTGACTCAGCCCTCCGCGCTGTCCGTAACCTTGGGACAGACGGCCAAGATCACCTGCCAAGGTGGCAGCTTAGGTAGCAGTTATGCTCACTGGTACCAGCAGAAGCCAGGCCAGGCCCCTGTGCTGGTCATCTATGATGATGACAGCAGGCCCTCAGGGATCCCTGAGCGGTTCTCTGGCTCCAGCTCTGGGGGCACAGCCACCCTGACCATCAGCGGGGCCCAGGCCGAGGACGAGGGTGACTATTACTGTCAGTCAGCAGACAGCAGTGGTAATGCTGCTGTGTTCGGCGGAGGGACCCATCTGACCGTCCTG | 184 |
| 71D6 | GAGTTGCAGCTGGTGGAGTCTGGGGGAGGCTTGGTGCAGCCTGGGGGGTCTCTGAGACTCTCCTGTGCAGCCTCTGGATTCACCTTCAGTAGCTATGGCATGAGCTGGGTCCGCCAGGCTCCAGGGAAGGGGCTCGAGTGGGTCTCAGCTATTAATAGTTATGGTGGTAGCACAAGCTATGCAGACTCCGTGAAGGGCCGATTCACCATCTCCAGAGACAACGCCAAGAACACGCTGTATCTGCAAATGAACAGCCTGAAACCTGAGGACACGGCCGTGTATTACTGTGCAAAAGAAGTGCGGGCCGACCTAAGCCGCTATAACGACTATGAGTCGTATGACTACTGGGGCCAGGGGACCCAGGTCACCGTCTCCTCA | 185 | CAGCCGGTGCTGAATCAGCCCTCCGCGCTGTCCGTAACCTTGGGACAGACGGCCAAGATCACCTGCCAAGGTGGCAGCTTAGGTGCGCGTTATGCTCACTGGTACCAGCAGAAGCCAGGCCAGGCCCCTGTGCTGGTCATCTATGATGATGACAGCAGGCCCTCAGGGATCCCTGAGCGGTTCTCTGGCTCCAGCTCTGGGGGCACAGCCACCCTGACCATCAGCGGGGCCCAGGCCGAGGACGAGGGTGACTATTACTGTCAGTCAGCAGACAGCAGTGGTTCTGTGTTCGGCGGAGGGACCCATCTGACCGTCCTG | 186 |

TABLE 6-continued

Variable domain nucleotide sequences of Fabs binding to both human and mouse MET.

| Clone | VH | SEQ ID NO. | VL | SEQ ID NO. |
|---|---|---|---|---|
| 71A3 | GAGGTGCAGCTCGTGGAGTCTGGGGGAGGCTTGGTGCA GCCTGGGGGGTCTCTGAGACTCTCCTGTGCAGCCTCTG GATTCAGCTTCAAGGACTATGACATAACCTGGGTCCGC CAGGCTCCGGGAAAGGGGCTCGAGTGGGTCTCAACTAT TACTAGTCGTAGTGGTAGCACAAGCTATGTAGACTCCG TAAAGGGCCGATTCACCATCTCCGGAGACAACGCCAAG AACACGCTGTATCTGCAAATGAACAGCCTGAAACCTGA GGACACGGCCGTGTATTACTGTGCAAAAGTTTACGCGA CTACCTGGGACGTCGGCCCTCTGGGCTACGGCATGGAC TACTGGGGCAAGGGGACCCTGGTCACCGTCTCCTCA | 187 | TCCTATGAGCTGACTCAGCCCTCCGCGCTGTCCGTAAC CTTGGGACAGACGGCCAAGATCACCTGCCAAGGTGGCA GCTTAGGTAGCAGTTATGCTCACTGGTACCAGCAGAAG CCAGGCCAGGCCCCTGTGCTGGTCATCTATGATGATGA CAGCAGGCCCTCAGGGATCCCTGAGCGGTTCTCTGGCT CCAGCTCTGGGGGCACAGCCACCCTGACCATCAGCGGG GCCCAGGCCGAGGACGAGGGTGACTATTACTGTCAGTC AGCAGACAGCAGTGGTAATGCTGCTGTGTTCGGCGGAG GGACCCATCTGACCGTCCTG | 188 |
| 71G2 | GAGGTGCAGCTGCAGGAGTCGGGGGGAGGCTTGGTGCA GCCTGGGGGGTCTCTGAGACTCTCCTGTGCAGCCTCTG GATTCACCTTCAGTATATATGACATGAGCTGGGTCCGC CAGGCTCCAGGAAAGGGGCTCGAGTGGGTCTCAACTAT TAATAGTGATGGTAGTAGCACAAGCTATGTAGACTCCG TGAAGGGCCGATTCACCATCTCCAGAGACAACGCCAAG AACACGCTGTATCTGCAAATGAACAGCCTGAAACCTGA GGACACGGCCGTGTATTACTGTGCAAAAGTTTACGGTA GTACCTGGGACGTCGGCCCTATGGGCTACGGCATGGAC TACTGGGGCAAAGGGACCCTGGTCACTGTCTCCTCA | 189 | TCCTCTGCACTGACTCAGCCCTCCGCGCTGTCCGTGTC CTTGGGACAGACGGCCAGGATCACCTGCCAAGGTGGCA GCTTAGGTAGCAGTTATGCTCACTGGTACCAGCAGAAG CCAGGCCAGGCCCCTGTGCTGGTCATCTATGGTGATGA CAGCAGGCCCTCAGGGATCCCTGAGCGGTTCTCTGGCT CCAGCTCTGGGGGCACAGCCACCCTGACCATCAGCGGG GCCCAGGCCGAGGACGAGGATGACTATTACTGTCAGTC AACAGACAGCAGTGGTAATACTGTGTTCGGCGGAGGGA CCCGACTGACCGTCCTG | 190 |
| 76G7 | CAGGTGCAGCTGGTGGAGTCTGGGGGAAACTTGGTGCA GCCTGGGGGTTCTCTGAGACTCTCCTGTGCAGGAAACA GATTCACCTTCAGTAACTACTACATGAGCTGGGTCCGC CAGGCTCCAGGGAAGGGGCTGGAATGGGTGTCCGATAT TTATAGTGACGGTAGTACCACATGGTATTCAGACTCCG TCAAGGGCCGATTCACCATCTCCAGAGACAACGCCAAG AACACGCTGTCTCTGCAAATGAACAGTCTGAAATCTGA GGACACGGCCGTCTATTACTGTGCGCGCGTGAAGATCT ATCCGGGGGGTATGACGCCTGGGGCCAGGGGACCCAG GTCACCGTCTCCTCA | 191 | CAGGCAGGGCTGACTCAGCCTCCCTCCGTGTCTGGGTC TCCAGGAAAGACGGTCACCATCTCCTGCACTGGAAACA GCAGTGATGTTGGGTATGGAAACTATGTCTCCTGGTAC CAGCAGTTCCCAGGAATGGCCCCCAAACTCCTGATATA TCGTCAATAAACGGGCCTCAGGGATCACTGATCGCT TCTCTGGCTCCAAGTCAGGCAACACGGCCTCCCTGACC ATCTCTGGGCTCCAGTCTGAGGACGAGGCTGATTATTA CTGTGCCTCATATACAGGTAGCAACAATATCGTGTTCG GCGGAGGGACCCATCTAACCGTCCTC | 192 |
| 71G12 | CAGGTGCAGCTGCAGGAGTCGGGGGGAGACTTGGTGCA GCCTGGGGGGTCTCTGAGAGTCTCCTGTGTAGTCTCTG GATTCACCTTCAGTCGCTACTACATGAGCTGGGTCCGC CAGGCTCCAGGGAAGGGGCTCGAGTGGGTCTCATCTAT TGATAGTTATGGTTACAGCACATACTATACAGACTCCG TGAAGGGCCGATTCACCATCTCCAGAGACAACGCCAAG AACACGCTGTATCTGCAAATGAACAGCCTGAAACCTGA GGACACGGCCCTGTATTACTGTGCAAGAGCGAAAACGA CTTGGAGTTATGACTACTGGGGCCAGGGGACCCAGGTC ACCGTCTCCTCA | 193 | GAAATTGTGTTGACGCAGTCTCCCAGCTCCGTGACTGC ATCTGTAGGAGGGAAGGTCACTATCAACTGTAAGTCCA GCCAGAGCGTCTTCATAGCTTCTAATCAGAAAACCTAC TTAAACTGGTACCAGCAGAGACCTGGACAGTCTCCGAG GTTGGTCATCAGCTATGCGTCCACCCGTGAATCGGGGA TCCCTGATCGATTCAGCGGCAGTGGGTCCACAACAGAT TTCACTCTCACGATCAGCAGTGTCCAGCCTGAAGATGC GGCCGTGTATTACTGTCAGCAGGCTTATAGCCATCCAA CGTTCGGCCAGGGGACCAAGGTGGAACTCAAA | 194 |
| 74C8 | GAGGTGCAGCTCGTGGAGTCTGGGGGAGGCTTGGTGCA ACCTGGGGGTTCTCTGAGACTCTCCTGTGCAGCCTCTG GATTCACCTTCAGGAATTACCACATGAGTTGGGTCCGC CAGGTTCCAGGGAAGGGGTTCGAGTGGATCTCAGATAT TAATAGTGCAGGTGGTAGCACATACTATGCAGACTCCG TGAAGGGCCGATTCACCATCTCCAGAGACAACGCCAAG AACACGCTGTATCTGGAAATGAACAGCCTGAAACCTGA GGACACGGCCCTGTATTACTGTGCAAGAGTCAACGTCT GGGGGGGTGAACTACTGGGGCAAAGGGACCCTGGTCAGC GTCTCCTCA | 195 | CAGACTGTGGTGACTCAGGAGCCGTCCCTGTCAGTGTC TCCAGGAGGGACGGTCACACTCACCTGCGGCCTCAGCT CTGGGTCTGTCACTACCAGTAACTACCCTGGTTGGTTC CAGCAGACACCAGGCCAGGCTCCACGCACTCTTATCTA CAACACAAACAGCCGCCACTCTGGGGTCCCCAGTCGCT TCTCCGGATCCATCTCTGGGAACAAAGCCGCCCTCACC ATCACGGGGGCCCAGCCCGAGGACGAGGCCGACTATTA CTGTTCTCTGTACCCTGGTAGTTACACTAATGTGTTCG GCGGAGGGACCCATCTGACCGTCCTG | 196 |
| 72F8 | GAGTTGCAGCTGGTGGAGTCTGGGGGAGGCTTGGTGCA GCCTGgGGGGTCTCTGAGACTCtCCTGTGCAGCCTCTG GATTCACCTTCAGCAACTATGTCATGAGCTGGGTCCGC CAGGCTCCAGGGAAGGGGCTCGAGTGGGTCTCAGATAC TAATAGTGGTGGTAGCACAAGCTATGCAGACTCCGTGA AGGGCCGATTCACCATCTCTAGAGACAACGCCAAGAAC ACGCTGTATTTGCAAATGAACAGCCTGAAACCTGAGGA CACGGCATTGTATTACTGTGCGAGATCATTTTTCTACG GCATGAACTACTGGGGCAAAGGGACCCAGGTCACCGTG TCCTCA | 197 | CAGTCTGCCCTGACTCAGCCGCCCTCCCTCTCTGCATC TCCGGGATCATCTGTCAGACTCACCTGCACCCTGAGCA GTGGAAACAATATTGGCAGCTATGACATAAGTTGGTAC CAGCAGAAGGCAGGGAGCCCTCCCCGGTACCTCCTGAA CTACTACACCGACTCACGCAAGCACCAGGACTCCGGGG TCCCGAGCCGCTTCTCTGGGTCCAAAGATGCCTCGGCC AACGCAGGGCTTCTGCTCATCTCTGGGCTTCAGCCCGA GGACGAGGCTGACTATTACTGTTCTGCATACAAGAGTG GTTCTTACCGTTGGGTGTTCGGCGGAGGGACGCACGTG ACCGTCCTG | 198 |

The various Fab families and their ability to bind human and mouse MET are shown in Table 7.

TABLE 7

Fabs binding to both human MET (hMET) and mouse MET (mMET). Fabs are grouped in families based on their VH CDR3 sequence. Binding of Fabs to human and mouse MET ECD was determined by Surface Plasmon Resonance (SPR) and by ELISA. SPR values represent the koff ($s^{-1}$). ELISA values represent the Optical Density (OD) at 450 nm (AU, arbitrary units). Both SPR and ELISA were performed using crude periplasmic extracts. Fab concentration in the extract was not determined. Values are the mean of three independent measurements.

| Fab | VH | VL | SPR ($K_{off}$; $s^{-1}$) | | ELISA ($OD_{450}$; AU) | |
| --- | --- | --- | --- | --- | --- | --- |
| | | | hMET | mMET | hMET | mMET |
| 76H10 | VH 1 | Lambda | 5.68E−03 | 5.44E−03 | 3.704 | 3.697 |
| 71G3 | VH 2 | Lambda | 1.42E−03 | 1.41E−03 | 3.462 | 3.443 |
| 71D6 | VH 3a | Lambda | 2.94E−03 | 2.67E−03 | 3.261 | 3.072 |
| 71C3 | VH 3b | Lambda | 2.25E−03 | 2.58E−03 | 1.650 | 1.643 |
| 71D4 | VH 3c | Lambda | 2.17E−03 | 2.38E−03 | 0.311 | 0.307 |
| 71A3 | VH 4 | Lambda | 4.92E−03 | 4.74E−03 | 0.581 | 0.524 |
| 71G2 | VH 4 | Lambda | 1.21E−03 | 1.48E−03 | 0.561 | 0.543 |
| 76G7 | VH 5 | Lambda | 4.32E−03 | 4.07E−03 | 3.199 | 3.075 |
| 71G12 | VH 6 | Kappa | 2.28E−03 | 2.55E−03 | 0.450 | 0.420 |
| 74C8 | VH 9 | Lambda | 3.48E−03 | 3.70E−03 | 2.976 | 2.924 |
| 72F8 | VH 10 | Lambda | 4.96E−03 | 4.58E−03 | 3.379 | 3.085 |

Example 3: Chimerization of Fabs into mAbs

The cDNAs encoding the VH and VL (K or A) domains of selected Fab fragments were engineered into two separate pUPE mammalian expression vectors (U-protein Express) containing the cDNAs encoding CH1, CH2 and CH3 of human IgG1 or the human CL (K or A), respectively.

Production (by transient transfection of mammalian cells) and purification (by protein A affinity chromatography) of the resulting chimeric llama-human IgG1 molecules was outsourced to U-protein Express. Binding of chimeric mAbs to MET was determined by ELISA using hMET or mMET ECD in solid phase and increasing concentrations of antibodies (0-20 nM) in solution. Binding was revealed using HRP-conjugated anti-human Fc antibodies (Jackson Immuno Research Laboratories). This analysis revealed that all chimeric llama-human antibodies bound to human and mouse MET with picomolar affinity, displaying an $EC_{50}$ comprised between 0.06 nM and 0.3 nM. Binding capacity ($E_{MAX}$) varied from antibody to antibody, possibly due to partial epitope exposure in the immobilized antigen, but was similar in the human and mouse setting. $EC_{50}$ and $E_{MAX}$ values are shown in Table 9.

TABLE 9

Binding of chimeric mAbs to human and mouse MET as determined by ELISA using immobilized MET ECD in solid phase and increasing concentrations (0-20 nM) of antibodies in solution.

| mAb | hMET | | mMET | |
| --- | --- | --- | --- | --- |
| | $EC_{50}$ | $E_{MAX}$ | $EC_{50}$ | $E_{MAX}$ |
| 76H10 | 0.090 | 2.669 | 0.062 | 2.662 |
| 71G3 | 0.067 | 2.835 | 0.057 | 2.977 |
| 71D6 | 0.026 | 2.079 | 0.049 | 2.009 |
| 71C3 | 0.203 | 2.460 | 0.293 | 2.238 |
| 71D4 | 0.207 | 1.428 | 0.274 | 1.170 |
| 71A3 | 0.229 | 2.401 | 0.176 | 2.730 |
| 71G2 | 0.112 | 3.094 | 0.101 | 3.168 |
| 76G7 | 0.128 | 2.622 | 0.103 | 2.776 |
| 71G12 | 0.106 | 3.076 | 0.127 | 2.973 |
| 74C8 | 0.090 | 0.994 | 0.116 | 0.896 |
| 72F8 | 0.064 | 2.779 | 0.048 | 2.903 |

$EC_{50}$ values are expressed as nMol/L.
$E_{MAX}$ values are expressed as Optical Density (OD) at 450 nm (AU, arbitrary units).

We also analysed whether chimeric anti-MET antibodies bound to native human and mouse MET in living cells. To this end, increasing concentrations of antibodies (0-100 nM) were incubated with A549 human lung carcinoma cells (American Type Culture Collection) or MLP29 mouse liver precursor cells (a gift of Prof. Enzo Medico, University of Torino, Strada Provinciale 142 km 3.95, Candiolo, Torino, Italy; Medico et al., Mol Biol Cell 7, 495-504, 1996), which both express physiological levels of MET. Antibody binding to cells was analysed by flow cytometry using phycoerythrin-conjugated anti-human IgG1 antibodies (eBioscience) and a CyAn ADP analyser (Beckman Coulter). As a positive control for human MET binding, we used a commercial mouse anti-human MET antibody (R&D Systems) and phycoerythrin-conjugated anti-mouse IgG1 antibodies (eBioscience). As a positive control for mouse MET binding we used a commercial goat anti-mouse MET antibody (R&D Systems) and phycoerythrin-conjugated anti-goat IgG1 antibodies (eBioscience). All antibodies displayed dose-dependent binding to both human and mouse cells with an $EC_{50}$ varying between 0.2 nM and 2.5 nM. Consistent with the data obtained in ELISA, maximal binding ($E_{MAX}$) varied depending on antibody, but was similar in human and mouse cells. These results indicate that the chimeric llama-human antibodies recognize membrane-bound MET in its native conformation in both human and mouse cellular systems. $EC_{50}$ and $E_{MAX}$ values are shown in Table 10.

TABLE 10

Binding of chimeric mAbs to human and mouse cells as determined by flow cytometry using increasing concentrations (0-50 nM) of antibodies.

| mAb | Human cells (A549) | | Mouse cells (MLP29) | |
| --- | --- | --- | --- | --- |
| | $EC_{50}$ | $E_{MAX}$ | $EC_{50}$ | $E_{MAX}$ |
| 76H10 | 2.345 | 130.2 | 1.603 | 124.3 |
| 71G3 | 0.296 | 116.9 | 0.214 | 116.2 |
| 71D6 | 0.259 | 112.7 | 0.383 | 121.2 |
| 71C3 | 0.572 | 106.5 | 0.585 | 115.1 |
| 71D4 | 0.371 | 107.2 | 0.498 | 94.8 |
| 71A3 | 0.514 | 160.8 | 0.811 | 144.2 |
| 71G2 | 0.604 | 144.4 | 0.688 | 129.9 |
| 76G7 | 2.298 | 121.2 | 2.371 | 114.8 |
| 71G12 | 2.291 | 109.9 | 2.539 | 121.2 |
| 74C8 | 0.235 | 85.7 | 0.208 | 73.8 |
| 72F8 | 0.371 | 156.3 | 0.359 | 171.6 |

$EC_{50}$ values are expressed as nMol/L.
$E_{MAX}$ values are expressed as % relative to control.

Example 4: Receptor Regions Responsible for Antibody Binding

In order to map the receptor regions recognized by antibodies binding to both human and mouse MET (herein after referred to as human/mouse equivalent anti-MET antibodies), we measured their ability to bind to a panel of engineered proteins derived from human MET generated as described (Basilico et al, J Biol. Chem. 283, 21267-21227, 2008). This panel included: the entire MET ECD (Decoy MET); a MET ECD lacking IPT domains 3 and 4 (SEMA-PSI-IPT 1-2); a MET ECD lacking IPT domains 1-4 (SEMA-PSI); the isolated SEMA domain (SEMA); a fragment containing IPT domains 3 and 4 (IPT 3-4). Engineered MET proteins were immobilized in solid phase and exposed to increasing concentrations of chimeric antibodies (0-50 nM) in solution. Binding was revealed using HRP-conjugated anti-human Fc antibodies (Jackson Immuno Research Laboratories). As shown in Table 11, this analysis revealed that 7 mAbs recognize an epitope within the SEMA domain, while the other 4 recognize an epitope within the PSI domain.

2014). Chimeras were immobilized in solid phase and then exposed to increasing concentrations of mAbs (0-20 nM) in solution. Binding was revealed using HRP-conjugated anti-human Fc antibodies (Jackson Immuno Research Laboratories). This analysis unveiled that 5 SEMA-binding mAbs (71D6, 71C3, 71D4, 71A3, 71G2) recognize an epitope localized between aa 314-372 of human MET, a region that corresponds to blades 4-5 of the 7-bladed SEMA β-propeller (Stamos et al., EMBO J. 23, 2325-2335, 2004). The other 2 SEMA-binding mAbs (74C8, 72F8) recognize an epitope localized between aa 123-223 and 224-311, respectively, corresponding to blades 1-3 and 1-4 of the SEMA β-propeller. The PSI-binding mAbs (76H10, 71G3, 76G7, 71G12) did not appear to display any significant binding to any of the two PSI chimeras. Considering the results presented in Table 11, these antibodies probably recognize an epitope localized between aa 546 and 562 of human MET. These results are summarized in Table 12.

TABLE 12

Mapping of the epitopes recognized by human/mouse equivalent anti-MET antibodies as determined by ELISA. Human MET ECD (hMET) or llama MET ECD (lMET) as well as the llama-human MET chimeric proteins (CH1-7) were immobilized in solid phase and then exposed to increasing concentrations of mAbs.

| mAb | hMET | lMET | CH1 | CH2 | CH3 | CH4 | CH5 | CH6 | CH7 | Epitope (aa) |
|---|---|---|---|---|---|---|---|---|---|---|
| 76H10 | + | − | + | + | + | + | + | − | − | 546-562 |
| 71G3  | + | − | + | + | + | + | + | − | − | 546-562 |
| 71D6  | + | − | + | + | + | − | − | + | + | 314-372 |
| 71C3  | + | − | + | + | + | − | − | + | + | 314-372 |
| 71D4  | + | − | + | + | + | − | − | + | + | 314-372 |
| 71A3  | + | − | + | + | + | − | − | + | + | 314-372 |
| 71G2  | + | − | + | + | + | − | − | + | + | 314-372 |
| 76G7  | + | − | + | + | + | + | + | − | − | 546-562 |
| 71G12 | + | − | + | + | + | + | + | − | − | 546-562 |
| 74C8  | + | − | + | − | − | − | − | + | + | 123-223 |
| 72F8  | + | − | + | + | − | − | − | + | + | 224-311 |

TABLE 11

Binding of human/mouse equivalent anti-MET antibodies to the panel of MET deletion mutants. The MET domain responsible for antibody binding is indicated in the last column to the right.

| mAb | Decoy MET | SEMA-PSI-IPT 1-2 | SEMA-PSI | SEMA | IPT 3-4 | Binding domain |
|---|---|---|---|---|---|---|
| 76H10 | + | + | + | − | − | PSI |
| 71G3  | + | + | + | − | − | PSI |
| 71D6  | + | + | + | + | − | SEMA |
| 71C3  | + | + | + | + | − | SEMA |
| 71D4  | + | + | + | + | − | SEMA |
| 71A3  | + | + | + | + | − | SEMA |
| 71G2  | + | + | + | + | − | SEMA |
| 76G7  | + | + | + | − | − | PSI |
| 71G12 | + | + | + | − | − | PSI |
| 74C8  | + | + | + | + | − | SEMA |
| 72F8  | + | + | + | + | − | SEMA |

To more finely map the regions of MET responsible for antibody binding, we exploited the absence of cross-reactivity between our antibodies and llama MET (the organism used for generating these immunoglobulins). To this end, we generated a series of llama-human and human-llama chimeric MET proteins spanning the entire MET ECD as described (Basilico et al., J Clin Invest. 124, 3172-3186, Example 5: HGF Competition Assays The above analysis suggests that the epitopes recognized by some of the human/mouse equivalent anti-MET antibodies may overlap with those engaged by HGF when binding to MET (Stamos et al., EMBO J. 23, 2325-2335, 2004; Merchant et al., Proc Natl Acad Sci USA 110, E2987-2996, 2013; Basilico et al., J Clin Invest. 124, 3172-3186, 2014). To investigate along this line, we tested the competition between mAbs and HGF by ELISA. Recombinant human and mouse HGF (R&D Systems) were biotinylated at the N-terminus using NHS-LC-biotin (Thermo Scientific). MET-Fc protein, either human or mouse (R&D Systems), was immobilized in solid phase and then exposed to 0.3 nM biotinylated HGF, either human or mouse, in the presence of increasing concentrations of antibodies (0-120 nM). HGF binding to MET was revealed using HRP-conjugated streptavidin (Sigma-Aldrich). As shown in Table 13, this analysis allowed to divide human/mouse equivalent anti-MET mAbs into two groups: full HGF competitors (71D6, 71C3, 71D4, 71A3, 71G2), and partial HGF competitors (76H10, 71G3, 76G7, 71G12, 74C8, 72F8).

TABLE 13

Ability of human/mouse equivalent anti-MET antibodies to compete with HGF for binding to MET as determined by ELISA.

| mAb | hHGF on hMET | | mHGF on mMET | |
|---|---|---|---|---|
| | $IC_{50}$ (nM) | $I_{MAX}$ (%) | $IC_{50}$ (nM) | $I_{MAX}$ (%) |
| 76H10 | 1.86 | 64.22 | 2.01 | 62.71 |
| 71G3 | 0.49 | 63.16 | 0.53 | 62.87 |
| 71D6 | 0.29 | 98.34 | 0.34 | 90.54 |
| 71C3 | 1.42 | 93.64 | 1.56 | 89.23 |
| 71D4 | 0.34 | 95.62 | 0.40 | 91.34 |
| 71A3 | 0.51 | 93.37 | 0.54 | 87.74 |
| 71G2 | 0.23 | 97.84 | 0.26 | 91.86 |
| 76G7 | 1.47 | 69.42 | 1.56 | 62.52 |
| 71G12 | 3.87 | 51.39 | 4.05 | 50.67 |
| 74C8 | 0.43 | 76.89 | 0.49 | 71.55 |
| 72F8 | 0.45 | 77.34 | 0.52 | 72.79 |

A MET-Fc chimeric protein (either human or mouse) was immobilized in solid phase and exposed to a fixed concentration of biotinylated HGF (either human or mouse), in the presence of increasing concentrations of antibodies. HGF binding to MET was revealed using HRP-conjugated streptavidin. Antibody-HGF competition is expressed as $IC_{50}$ (the concentration that achieves 50% competition) and $I_{MAX}$ (the maximum % competition reached at saturation).

As a general rule, SEMA binders displaced HGF more effectively than PSI binders. In particular, those antibodies that recognize an epitope within blades 4 and 5 of the SEMA β-propeller were the most potent HGF competitors (71D6, 71C3, 71D4, 71A3, 71G2). This observation is consistent with the notion that SEMA blade 5 contains the high affinity binding site for the α-chain of HGF (Merchant et al., Proc Natl Acad Sci USA 110, E2987-2996, 2013). The PSI domain has not been shown to participate directly with HGF, but it has been suggested to function as a 'hinge' regulating the accommodation of HGF between the SEMA domain and the IPT region (Basilico et al., J Clin Invest. 124, 3172-3186, 2014). It is therefore likely that mAbs binding to PSI (76H10, 71G3, 76G7, 71G12) hamper HGF binding to MET by interfering with this process or by steric hindrance, and not by direct competition with the ligand. Finally, blades 1-3 of the SEMA β-propeller have been shown to be responsible for low-affinity binding of the p-chain of HGF, which plays a central role in MET activation but only partially contributes to the HGF-MET binding strength (Stamos et al., EMBO J. 23, 2325-2335, 2004). This could explain why mAbs binding to that region of MET (74C8, 72F8) are partial competitors of HGF.

Example 6: MET Activation Assays

Due to their bivalent nature, immunoglobulins directed against receptor tyrosine kinases may display receptor agonistic activity, mimicking the effect of natural ligands. To investigate along this line, we tested the ability of human/mouse equivalent anti-MET antibodies to promote MET auto-phosphorylation in a receptor activation assay. A549 human lung carcinoma cells and MLP29 mouse liver precursor cells were deprived of serum growth factors for 48 hours and then stimulated with increasing concentrations (0-5 nM) of antibodies or recombinant HGF (A549 cells, recombinant human HGF, R&D Systems; MLP29 cells, recombinant mouse HGF, R&D Systems). After 15 minutes of stimulation, cells were washed twice with ice-cold phosphate buffered saline (PBS) and then lysed as described (Longati et al., Oncogene 9, 49-57, 1994). Protein lysates were resolved by electrophoresis and then analysed by Western blotting using antibodies specific for the phosphorylated form of MET (tyrosines 1234-1235), regardless of whether human or mouse (Cell Signaling Technology). The same lysates were also analysed by Western blotting using anti-total human MET antibodies (Invitrogen) or anti-total mouse MET antibodies (R&D Systems). This analysis revealed that all human/mouse equivalent antibodies display MET agonistic activity. Some antibodies promoted MET auto-phosphorylation to an extent comparable to that of HGF (71G3, 71D6, 71C3, 71D4, 71A3, 71G2, 74C8). Some others (76H10, 76G7, 71G12, 72F8) were less potent, and this was particularly evident at the lower antibody concentrations. No clear correlation between MET activation activity and HGF-competition activity was observed.

To obtain more quantitative data, the agonistic activity of antibodies was also characterized by phospho-MET ELISA. To this end, A549 and MLP29 cells were serum-starved as above and then stimulated with increasing concentrations (0-25 nM) of mAbs. Recombinant human (A549) or mouse (MLP29) HGF was used as control. Cells were lysed and phospho-MET levels were determined by ELISA as described (Basilico et al., J Clin Invest. 124, 3172-3186, 2014). Briefly, 96 well-plates were coated with mouse anti-human MET antibodies or rat anti-mouse MET antibodies (both from R&D Systems) and then incubated with cell lysates. After washing, captured proteins were incubated with biotin-conjugated anti-phospho-tyrosine antibodies (Thermo Fisher), and binding was revealed using HRP-conjugated streptavidin (Sigma-Aldrich).

The results of this analysis are consistent with the data obtained by Western blotting. As shown in Table 14, 71G3, 71D6, 71C3, 71D4, 71A3, 71G2 and 74C8 potently activated MET, while 76H10, 76G7, 71G12 and 72F8 caused a less pronounced effect. In any case, all antibodies displayed a comparable effect in human and in mouse cells.

TABLE 14

Agonistic activity of human/mouse equivalent anti-MET antibodies in human and mouse cells as measured by ELISA.

| mAb | A549 cells | | MLP29 cells | |
|---|---|---|---|---|
| | $EC_{50}$ (nM) | $E_{MAX}$ (%) | $EC_{50}$ (nM) | $E_{MAX}$ (%) |
| 76H10 | 1.77 | 61.23 | 2.91 | 64.10 |
| 71G3 | 0.41 | 95.72 | 0.37 | 97.81 |
| 71D6 | 0.32 | 101.57 | 0.21 | 114.56 |
| 71C3 | 0.35 | 86.19 | 0.33 | 98.85 |
| 71D4 | 0.59 | 84.63 | 0.51 | 95.34 |
| 71A3 | 0.31 | 86.56 | 0.26 | 95.95 |
| 71G2 | 0.37 | 101.35 | 0.25 | 109.87 |
| 76G7 | 1.86 | 62.34 | 1.19 | 71.45 |
| 71G12 | 2.48 | 70.61 | 2.01 | 75.39 |
| 74C8 | 0.52 | 87.63 | 0.41 | 102.15 |
| 72F8 | 1.51 | 69.74 | 0.79 | 66.82 |
| HGF | 0.19 | 100.00 | 0.23 | 100.00 |

A549 human lung carcinoma cells and MLP29 mouse liver precursor cells were serum-starved and then stimulated with increasing concentrations of mAbs. Recombinant human HGF (hHGF; A549) or mouse HGF (mHGF; MLP29) was used as control. Cell lysates were analysed by ELISA using anti-total MET antibodies for capture and anti-phospho-tyrosine antibodies for revealing. Agonistic activity is expressed as $EC_{50}$ (nM) and $E_{MAX}$ (% HGF activity).

Example 7: Scatter Assay

To evaluate whether the agonistic activity of human/mouse equivalent anti-MET antibodies could translate into biological activity, we performed scatter assays with both human and mouse epithelial cells. To this end, HPAF-II human pancreatic adenocarcinoma cells (American Type Culture Collection) and MLP29 mouse liver precursor cells were stimulated with increasing concentrations of recombinant HGF (human or mouse; both from R&D Systems) and cell scattering was determined 24 hours later by microscopy as described previously (Basilico et al., J Clin Invest. 124, 3172-3186, 2014). This preliminary analysis revealed that HGF-induced cell scattering is linear until it reaches saturation at approximately 0.1 nM in both cell lines. Based on these HGF standard curves, we elaborated a scoring system ranging from 0 (total absence of cell scattering in the absence of HGF) to 4 (maximal cell scattering in the presence of 0.1 nM HGF). HPAF-II and MLP29 cells were stimulated with increasing concentrations of human/mouse equivalent anti-MET antibodies, and cell scattering was determined 24 hours later using the scoring system described above. As shown in Table 15, this analysis revealed that all mAbs tested promoted cell scattering in both the human and the mouse cell systems, with substantially overlapping results on both species. 71 D6 and 71G2 displayed the very same activity as HGF; 71G3 and 71A3 were just slightly less potent than HGF; 71C3 and 74C8 required a substantially higher concentration in order to match the activity of HGF; 71D4, 76G7, 71G12 and 72F8 did not reach saturation in this assay.

TABLE 15

Biological activity of human/mouse equivalent anti-MET antibodies as measured in a cell-based scatter assay. HPAF-II human pancreatic adenocarcinoma cells and MLP29 mouse liver precursor cells were stimulated with increasing concentrations of human/mouse equivalent anti-MET antibodies, and cell scattering was determined 24 hours later using the scoring system described in the text (0, absence of cell scattering; 4, maximal cell scattering).

| mAb | mAb concentration (nM) | | | | | | | | |
|---|---|---|---|---|---|---|---|---|---|
| | 9.000 | 3.000 | 1.000 | 0.333 | 0.111 | 0.037 | 0.012 | 0.004 | 0.001 |
| HPAF-II human pancreatic adenocarcinoma cells | | | | | | | | | |
| 76H10 | 3 | 2 | 1 | 0 | 0 | 0 | 0 | 0 | 0 |
| 71G3 | 4 | 4 | 4 | 4 | 3 | 2 | 1 | 0 | 0 |
| 71D6 | 4 | 4 | 4 | 4 | 4 | 3 | 2 | 1 | 0 |
| 71C3 | 4 | 4 | 3 | 2 | 1 | 0 | 0 | 0 | 0 |
| 71D4 | 2 | 2 | 1 | 0 | 0 | 0 | 0 | 0 | 0 |
| 71A3 | 4 | 4 | 4 | 4 | 3 | 3 | 2 | 0 | 0 |
| 71G2 | 4 | 4 | 4 | 4 | 4 | 3 | 2 | 1 | 0 |
| 76G7 | 3 | 2 | 1 | 0 | 0 | 0 | 0 | 0 | 0 |
| 71G12 | 3 | 2 | 2 | 1 | 0 | 0 | 0 | 0 | 0 |
| 74C8 | 4 | 4 | 3 | 3 | 2 | 1 | 0 | 0 | 0 |
| 72F8 | 3 | 2 | 1 | 0 | 0 | 0 | 0 | 0 | 0 |
| hHGF | 4 | 4 | 4 | 4 | 4 | 3 | 2 | 1 | 0 |
| IgG1 | 0 | 0 | 0 | 0 | 0 | 0 | 0 | 0 | 0 |
| MLP29 mouse liver precursor cells | | | | | | | | | |
| 76H10 | 3 | 2 | 1 | 0 | 0 | 0 | 0 | 0 | 0 |
| 71G3 | 4 | 4 | 4 | 4 | 2 | 1 | 0 | 0 | 0 |
| 71D6 | 4 | 4 | 4 | 4 | 4 | 3 | 2 | 1 | 0 |
| 71C3 | 4 | 4 | 3 | 2 | 1 | 0 | 0 | 0 | 0 |
| 71D4 | 2 | 2 | 1 | 0 | 0 | 0 | 0 | 0 | 0 |
| 71A3 | 4 | 4 | 4 | 4 | 3 | 3 | 2 | 0 | 0 |
| 71G2 | 4 | 4 | 4 | 4 | 4 | 2 | 1 | 0 | 0 |
| 76G7 | 3 | 2 | 1 | 0 | 0 | 0 | 0 | 0 | 0 |
| 71G12 | 3 | 2 | 2 | 1 | 0 | 0 | 0 | 0 | 0 |
| 74C8 | 4 | 4 | 3 | 3 | 2 | 1 | 0 | 0 | 0 |
| 72F8 | 3 | 2 | 1 | 0 | 0 | 0 | 0 | 0 | 0 |
| mHGF | 4 | 4 | 4 | 4 | 4 | 3 | 2 | 1 | 0 |
| IgG1 | 0 | 0 | 0 | 0 | 0 | 0 | 0 | 0 | 0 |

Example 8: Protection Against Drug-Induced Apoptosis

Several lines of experimental evidence indicate that HGF display a potent anti-apoptotic effect on MET-expressing cells (reviewed by Nakamura et al., J Gastroenterol Hepatol. 26 Suppl 1, 188-202, 2011). To test the potential anti-apoptotic activity of human/mouse equivalent anti-MET antibodies, we performed cell-based drug-induced survival assays. MCF10A human mammary epithelial cells (American Type Culture Collection) and MLP29 mouse liver precursor cells were incubated with increasing concentrations of staurosporine (Sigma Aldrich). After 48 hours, cell viability was determined by measuring total ATP concentration using the Cell Titer Glo kit (Promega) with a Victor X4 multilabel plate reader (Perkin Elmer). This preliminary analysis revealed that the drug concentration that induced about 50% cell death is 60 nM for MCF10A cells and 100 nM for MLP29 cells. Next, we incubated MCF10A cells and MLP29 cells with the above determined drug concentrations in the presence of increasing concentrations (0-32 nM) of anti-MET mAbs or recombinant HGF (human or mouse; both from R&D Systems). Cell viability was determined 48 hours later as described above. The results of this analysis, presented in Table 16, suggest that human/mouse equivalent antibodies protected human and mouse cells against staurosporine-induced cell death to a comparable extent. While some mAbs displayed a protective activity similar or superior to that of HGF (71G3, 71 D6, 71G2), other molecules displayed only partial protection (76H10, 71C3, 71D4, 71A3, 76G7, 71G12, 74C8, 72F8), either in the human or in the mouse cell system.

TABLE 16

Biological activity of human/mouse equivalent anti-MET antibodies as measured by a cell-based drug-induced apoptosis assay.

| | MCF10A cells | | MLP29 cells | |
|---|---|---|---|---|
| mAb | $EC_{50}$ (nM) | $E_{MAX}$ (%) | $EC_{50}$ (nM) | $E_{MAX}$ (%) |
| 76H10 | >32.00 | 22.75 | >32.00 | 27.21 |
| 71G3 | 5.04 | 65.23 | 4.85 | 62.28 |
| 71D6 | 1.48 | 66.81 | 0.95 | 68.33 |
| 71C3 | 31.87 | 50.16 | 31.03 | 51.32 |
| 71D4 | 30.16 | 51.71 | 29.84 | 52.13 |
| 71A3 | <0.50 | 71.70 | <0.50 | 70.54 |
| 71G2 | 1.06 | 64.85 | 1.99 | 58.29 |
| 76G7 | 25.41 | 51.93 | 30.08 | 50.16 |
| 71G12 | >32.00 | 39.35 | >32.00 | 39.73 |
| 74C8 | >32.00 | 41.74 | >32.00 | 37.52 |
| 72F8 | >32.00 | 35.79 | >32.00 | 43.81 |
| HGF | 4.57 | 59.28 | 5.35 | 58.65 |

MCF10A human mammary epithelial cells and MLP29 mouse liver precursor cells were incubated with a fixed concentration of staurosporine in the the presence of increasing concentrations of anti-MET mAbs or recombinant HGF (human or mouse), and total ATP content was determined 48 hours later. Cell viability was calculated as % total ATP content relative to cells treated with neither staurosporine nor antibodies, and is expressed as $EC_{50}$ and $E_{MAX}$.

Example 9: Branching Morphogenesis Assay

HGF is a pleiotropic cytokine which promotes the harmonic regulation of independent biological activities, including cell proliferation, motility, invasion, differentiation and survival. The cell-based assay that better recapitulates all of these activities is the branching morphogenesis assay, which replicates the formation of tubular organs and glands during embryogenesis (reviewed by Rosário and Birchmeier, Trends Cell Biol. 13, 328-335, 2003). In this assay, a spheroid of epithelial cells is seeded inside a 3D collagen matrix and is stimulated by HGF to sprout tubules which eventually form branched structures. These branched tubules resemble the hollow structures of epithelial glands, e.g. the mammary gland, in that they display a lumen surrounded by polarized cells. This assay is the most complete HGF assay that can be run in vitro.

In order to test whether human/mouse equivalent anti-MET antibodies displayed agonistic activity in this assay, we seeded LOC human kidney epithelial cells (Michieli et al. Nat Biotechnol. 20, 488-495, 2002) and MLP29 mouse liver precursor cells in a collagen layer as described (Hultberg et al., Cancer Res. 75, 3373-3383, 2015), and then exposed them to increasing concentrations of mAbs or recombinant HGF (human or mouse, both from R&D Systems). Branching morphogenesis was followed over time by microscopy, and colonies were photographed after 5 days. Quantification of branching morphogenesis activity was obtained by counting the number of branches for each spheroid. As shown in Table 17, all antibodies tested induced dose-dependent formation of branched tubules. However, consistent with the data obtained in MET auto-phosphorylation assays and cell scattering assays, 71D6, 71A3 and 71G2 displayed the most potent agonistic activity, similar or superior to that of recombinant HGF.

TABLE 17

Branching morphogenesis assay.

| mAb | 0 nM | 0.5 nM | 2.5 nM | 12.5 nM |
|---|---|---|---|---|
| LOC cells | | | | |
| 76H10 | 3.3 ± 1.5 | 7.3 ± 0.6 | 11.7 ± 1.5 | 16.7 ± 1.5 |
| 71G3 | 3.0 ± 1.0 | 13.7 ± 1.5 | 19.0 ± 2.6 | 22.3 ± 2.1 |
| 71D6 | 3.0 ± 1.0 | 29.0 ± 2.0 | 29.0 ± 2.6 | 32.7 ± 1.5 |
| 71C3 | 3.3 ± 0.6 | 8.7 ± 1.5 | 12.7 ± 2.1 | 15.7 ± 2.1 |
| 71D4 | 3.0 ± 1.0 | 9.0 ± 2.6 | 15.7 ± 1.2 | 18.7 ± 1.5 |
| 71A3 | 3.0 ± 1.7 | 24.0 ± 4.6 | 30.3 ± 3.2 | 31.3 ± 1.5 |
| 71G2 | 3.7 ± 1.5 | 25.3 ± 2.1 | 29.3 ± 3.5 | 31.7 ± 3.5 |
| 76G7 | 2.7 ± 0.6 | 6.7 ± 0.6 | 13.3 ± 4.2 | 16.3 ± 5.7 |
| 71G12 | 3.3 ± 0.6 | 7.0 ± 2.6 | 15.3 ± 5.5 | 16.0 ± 4.6 |
| 74C8 | 3.0 ± 1.0 | 10.3 ± 4.2 | 17.0 ± 4.6 | 18.7 ± 4.9 |
| 72F8 | 3.3 ± 1.5 | 9.0 ± 3.5 | 12.3 ± 2.1 | 16.0 ± 3.0 |
| hHGF | 3.0 ± 1.0 | 18.0 ± 2 | 27.7 ± 2.5 | 20.3 ± 2.1 |
| MLP29 cells | | | | |
| 76H10 | 0.3 ± 0.6 | 10.7 ± 4.0 | 14.3 ± 3.2 | 24.7 ± 6.0 |
| 71G3 | 0.3 ± 0.6 | 24.7 ± 4.5 | 34.3 ± 5.5 | 29.3 ± 8.0 |
| 71D6 | 1.3 ± 1.2 | 32.7 ± 3.5 | 39.0 ± 7.5 | 41.3 ± 8.0 |
| 71C3 | 0.3 ± 0.6 | 11.7 ± 3.5 | 15.7 ± 6.5 | 24.7 ± 6.5 |
| 71D4 | 0.7 ± 1.2 | 16.0 ± 2.6 | 14.7 ± 4.5 | 21.7 ± 5.5 |
| 71A3 | 0.7 ± 0.6 | 30.3 ± 2.1 | 42.0 ± 6.2 | 42.7 ± 8.0 |
| 71G2 | 1.0 ± 1.0 | 34.0 ± 2.6 | 46.3 ± 4.7 | 45.0 ± 7.0 |
| 76G7 | 0.3 ± 0.6 | 14.7 ± 2.1 | 18.7 ± 4.5 | 24.7 ± 6.5 |
| 71G12 | 1.0 ± 1.0 | 14.0 ± 2.6 | 14.7 ± 5.5 | 22.7 ± 6.0 |
| 74C8 | 0.7 ± 0.6 | 17.3 ± 2.5 | 15.3 ± 6.0 | 22.3 ± 9.0 |
| 72F8 | 1.0 ± 1.0 | 12.7 ± 3.1 | 11.7 ± 3.5 | 18.7 ± 2.5 |
| mHGF | 0.7 ± 1.2 | 32.3 ± 4.0 | 43.7 ± 4.2 | 36.0 ± 7.2 |

Cell spheroids preparations of LOC human kidney epithelial cells or MLP29 mouse liver precursor cells were seeded in a collagen layer and then incubated with increasing concentrations (0, 0.5, 2.5 and 12.5 nM) of mAbs or recombinant HGF (LOC, human HGF; MLP29, mouse HGF). Branching morphogenesis was followed over time by microscopy, and colonies were photographed after 5 days. Branching was quantified by counting the number of branches for each spheroid (primary branches plus secondary branches).

Example 10: Fine Epitope Mapping

In order to finely map the epitopes of MET recognized by human/mouse equivalent anti-MET antibodies we pursued the following strategy. We reasoned that, if an antibody generated in llamas and directed against human MET cross-reacts with mouse MET, then this antibody probably recognizes a residue (or several residues) that is (or are) conserved between *H. sapiens* and *M. musculus* but not among *H. sapiens*, *M. musculus* and *L. glama*. The same reasoning can be extended to *R. norvegicus* and *M. fascicularis*.

To investigate along this line, we aligned and compared the amino acid sequences of human (UniProtKB #P08581; aa 1-932), mouse (UniProtKB #P16056.1; aa 1-931), rat (NCBI #NP_113705.1; aa 1-931), cynomolgus monkey (NCBI #XP_005550635.2; aa 1-948) and llama MET (GenBank #KF042853.1; aa 1-931) among each other. With reference to Table 12, we concentrated our attention within the regions of MET responsible for binding to the 71 D6, 71C3, 71D4, 71A3 and 71G2 antibodies (aa 314-372 of human MET) and to the 76H10 and 71G3 antibodies (aa 546-562 of human MET). Within the former region of human MET (aa 314-372) there are five residues that are conserved in human and mouse MET but not in llama MET (Ala 327, Ser 336, Phe 343, Ile 367, Asp 372). Of these, four residues are also conserved in rat and cynomolgus monkey MET (Ala 327, Ser 336, Ile 367, Asp 372). Within the latter region of human MET (aa 546-562) there are three residues that are conserved in human and mouse MET but not in llama MET (Arg 547, Ser 553, Thr 555). Of these, two residues are also conserved in rat and cynomolgus monkey MET (Ser 553 and Thr 555).

Using human MET as a template, we mutagenized each of these residues in different permutations, generating a series of MET mutants that are fully human except for specific residues, which are llama. Next, we tested the affinity of selected SEMA-binding mAbs (71D6, 71C3, 71D4, 71A3, 71G2) and PSI-binding mAbs (76H10 and 71G3) for these MET mutants by ELISA. To this end, the various MET proteins were immobilized in solid phase (100 ng/well in a 96-well plate) and then exposed to increasing concentrations of antibodies (0-50 nM) solution. As the antibodies used were in their human constant region format, binding was revealed using HRP-conjugated anti-human Fc secondary antibody (Jackson Immuno Research Laboratories). Wild-type human MET was used as positive control. The results of this analysis are presented in Table 18.

TABLE 18

The epitopes of MET responsible for agonistic antibody binding represent residues conserved among *H. sapiens*, *M. musculus*, *R. norvegicus*, *M. fascicularis* but not among the same species and *L. glama*. The relevance of residues conserved among human, mouse, rat, cynomolgus monkey but not llama MET for binding to agonistic mAbs was tested by ELISA. Wild-type (WT) or mutant (MT) human MET ECD was immobilized in solid phase and exposed to increasing concentrations of mAbs in solution. Binding was revealed using anti-human Fc secondary antibodies. All binding values were normalized to the WT protein and are expressed as % binding ($E_{MAX}$) compared to WT MET.

| MUTA-MT | TIONS | mAb binding (% WT MET ECD) | | | | | | |
|---|---|---|---|---|---|---|---|---|
| | | SEMA BINDERS | | | | | PSI BINDERS | |
| | | 71D6 | 71C3 | 71D4 | 71A3 | 71G2 | 76H10 | 71G3 |
| WT | — | 100.0 | 100.0 | 100.0 | 100.0 | 100.0 | — | — |
| A | 1, 2, 3 | 103.3 | 99.8 | 114.5 | 116.8 | 92.1 | — | — |
| B | 4, 5 | 0.0 | 0.0 | 0.0 | 0.0 | 0.0 | — | — |
| C | 1, 2, 3, 4, 5 | 0.0 | 0.0 | 0.0 | 0.0 | 0.0 | — | — |
| D | 1, 2 | 128.0 | 101.8 | 119.6 | 127.9 | 113.5 | — | — |
| E | 2, 3, 4 | 43.6 | 59.6 | 57.2 | 65.4 | 41.4 | — | — |
| F | 2, 4, 5 | 0.0 | 0.0 | 0.0 | 0.0 | 0.0 | — | — |
| G | 3, 4, 5 | 0.0 | 0.0 | 0.0 | 0.0 | 0.0 | — | — |
| H | 2, 4 | 38.6 | 61.6 | 58.7 | 76.7 | 40.2 | — | — |
| I | 6, 7, 8 | — | — | — | — | — | 100.0 | 100.0 |
| J | 6, 7 | — | — | — | — | — | 89.0 | 91.2 |
| K | 6, 8 | — | — | — | — | — | 0.0 | 0.0 |
| L | 7, 8 | — | — | — | — | — | 0.0 | 0.0 |

The results presented above provide a definite and clear picture of the residues relevant for binding to our agonistic antibodies.

All the SEMA binders tested (71D6, 71C3, 71D4, 71A3, 71G2) appear to bind to an epitope that contains 2 key amino acids conserved in human, mouse, cynomolgus and rat MET but not in llama MET lying within blade 5 of the SEMA β-propeller: Ile 367 and Asp 372. In fact, mutation of Ala 327, Ser 336 or Phe 343 did not affect binding at all; mutation of Ile 367 partially impaired binding; mutation of Ile 367 and Asp 372 completely abrogated binding. We conclude that both Ile 367 and Asp 372 of human MET are important for binding to the SEMA-directed antibodies tested.

Also the PSI binders tested (76H10, 71G3) appear to bind to a similar or the same epitope. In contrast to the SEMA epitope, however, the PSI epitope contains only one key amino acid also conserved in human, mouse, cynomolgus and rat MET but not in llama MET: Thr 555. In fact, mutation of Arg 547 or Ser 553 did not affect binding at all, while mutation of Thr 555 completely abrogated it. We conclude that Thr 555 represents the crucial determinant for binding to the PSI-directed antibodies tested.

Example 11: Design, Generation and Characterization of a One-Armed MET-Specific Antagonistic Antibody Blocking the Biological Activity of Hepatocyte Growth Factor and Cross-Reactive with Human, Mouse, Rat and Monkey MET As the results presented so far suggest, all anti-MET antibodies described in this document display agonistic activity, although with different potency. This depends on the ability of the immunoglobulin molecule, which is bivalent, to stabilize the bound antigen (MET) in a dimeric form, leading to receptor trans-phosphorylation and activation. In order to generate a MET antagonistic antibody, also cross-reactive with human, mouse, rat and monkey MET, we transformed a bivalent agonistic antibody selected from the above panel (74C8) into a monovalent, one-armed form (74C8-OA). 74C8-OA consists of a single antigen-binding fragment (Fab) fused to a complete constant domain fragment (Fc) as described before (Merchant et al., Proc Natl Acad Sci. 110:2987-2996, 2013). The one-armed antibody was produced in mammalian cells and gel-purified as described for the other antibodies. The ability of 74C8-OA to bind to human, mouse, rat and monkey MET was assessed by ELISA using a MET ECD in solid phase and increasing concentrations of the antibody in solution. This analysis revealed that 74C8-OA binds with similar affinity to all of these MET proteins. The binding of 74C8-OA to native MET was determined by flow cytometry on human and mouse epithelial cells expressing MET. Cells were incubated with increasing concentrations of the antibody, and binding was revealed by flow cytometry analysis. The results obtained in these experiments indicated that 74C8-OA binds to native MET on the surface of living cells. In order to assess the ability of 74C8-OA to displace human or mouse HGF, an HGF competition assay was performed by ELISA. MET-Fc protein, either human or mouse, was immobilized in solid phase and then exposed to biotinylated human or mouse HGF in the presence of increasing concentrations of the antibody. HGF binding was measured by horse radish-conjugated streptavidin. This analysis revealed that 74C8-OA is a potent displacer of HGF in both human and mouse HGF/MET systems.

Both the agonistic and antagonistic activity of 74C8-OA were characterized by phospho-MET ELISA on mouse and human epithelial cells. For the agonistic activity assay, serum-starved cells were stimulated with increasing concentrations of 74C8-OA, lysed and then adsorbed on goat anti-human MET antibody (R&D Systems) in solid phase. Phospho-MET was revealed using a rabbit anti-pMET (Y1234-Y1235) antibody (Cell Signaling) and a secondary HRP-conjugated goat anti-rabbit antibody (Pierce). This analysis revealed that the agonistic activity of 74C8-OA is negligible at all concentrations tested. For the antagonistic activity, serum-starved mouse and human epithelial cells were stimulated with a fixed concentration (100 ng/ml) of recombinant human HGF (R&D Systems) in the presence of increasing concentrations of 74C8-OA. MET activation was determined by phospho-MET ELISA as described above. This analysis demonstrated that 74C8-OA displays strong MET antagonistic activity by inhibiting HGF-induced MET auto-phosphorylation.

We conclude that the 74C8-OA antibody is a potent MET antagonistic antibody that, in contrast to the MET agonist antibodies provided herein, does not display any significant MET agonistic activity.

Example 12: The 71 D6 MET Agonistic Antibody Inhibits Chronic Inflammation-Induced Colorectal Fibrosis and Carcinogenesis To cast light onto the potential pro-tumorigenic effect of MET activation in a chronic colon inflammation setting, we compared the pharmacological effect of a MET agonistic antibody (71 D6) with that of a MET antagonistic antibody (74C8-OA) in a classic two-hit colon carcinogenesis mouse model. To this end, we exposed 8 week-old female BALB/c mice (Charles River) to a single i.p. injection with azoxymethane (AOM; a potent mutagen for epithelial cells of the gastro-intestinal tract) at a dose of 12.5 mg/kg followed by three cycles of dextran sodium sulphate (DSS; a potent inducer of colon inflammation and ulceration) dissolved in the drinking water at a concentration of 6% (weight/volume). Each inflammatory cycle consisted of 7 days of DSS administration followed by 14 days on regular water. On day 8, when the first cycle of DSS started, mice were randomized into 4 arms of 11 mice each which received respectively: (i) vehicle only (PBS); (ii) the MET agonistic 71 D6 antibody at a dose of 1 mg/kg; (iii) the MET agonistic 71 D6 antibody at a dose of 5 mg/kg; (iv) the MET antagonistic antibody 74C8-OA at a dose of 5 mg/kg. An additional, fifth control arm contained 7 mice that received no AOM-DSS or antibody and served as healthy control. Mice were sacrificed 16 days after the third DSS cycle was interrupted. At autopsy, colons were collected, washed through, and their length and weight were determined. Following measurement, colons were cut open longitudinally and stained with 1% Alcian Blue solution to highlight tumour masses. Tumours were counted and photographed under a stereo-microscope. At the end of this procedure, colons were fixed in 4% paraformaldehyde, embedded in paraffin and processed for histological analysis. During the whole course of the experiment, mouse weight was monitored on a regular basis, and the clinical symptoms of ulcerative colitis were assessed by determining fecal blood, rectal bleeding and stool consistency. Quantification was achieved using a standard scoring system used in pre-clinical models (Kim et al., J Vis Exp. 60, pii: 3678, 2012): each parameter scored from 0 (absence of the symptom) to 3 (maximal manifestation of the symptom). Scores relative to the single parameters were summed together to give rise to the Disease Activity Index (DAI) ranging from 0 to 9.

As shown in FIG. 1A, exposure to DSS caused a weight loss that increased at each cycle (cycle 1, up to 15%; cycle 2, up to 20%; cycle 3, up to 25%). The DAI increased to a score of 3 or higher during cycle 1 and significantly worsened during cycles 2 and 3, reaching values higher than 4 during the last cycle (FIG. 1B). Remarkably, animals fail to recover after the last cycle and continued to display a DAI of 3 or higher, indicating that the inflammatory state could not be reverted at this stage. Consistent with the idea that HGF promotes colonic mucosa integrity and inhibits inflammation, the 71 D6 agonistic antibody reduced DSS-induced weight loss and accelerated recover, as well as dramatically inhibited the clinical symptoms of colon inflammation throughout the experiment as measured by DAI analysis. The 74C8-OA antagonistic antibody did not have any effect on either body weight or DAI until cycle 2 but, consistent with the idea that endogenous HGF may act as a natural factor against tissue injury, appeared to worsen the clinical signs of colon inflammation at cycle 3 and after.

As determined at autopsy, DSS reduced colon length by 30% (FIG. 2A), while it increased colon specific weight (expressed as grams/cm) up to 93% (FIG. 2B). Notably, 71 D6 treatment both at 1 and 5 mg/kg prevented colon shortage limiting it to non-significant variations, and maintained colon specific weight values very close to those of healthy control mice. On the contrary, the 74C8-OA MET antagonistic antibody performed similar to vehicle alone both in terms of colon length and colon specific weight.

Following length and weight measurement, colons were opened with a longitudinal cut and stained with 1% Alcian Blue solution, as described above. Colon specimens were analyzed by placing the flattened tissue under a stereomicroscope with their inner (lumen) side towards the lens, and photographed. This analysis revealed that AOM/DSS treatment resulted in the induction of a plethora of polyps at the level of the mid-colon, at approximately half way between the cecum joint and the anus (FIG. 3). Surprisingly, the agonistic 71 D6 antibody dramatically reduced colorectal carcinogenesis in this model, while the antagonistic 74C8-OA antibody did not affect AOM/DSS-induced tumour formation at all. Tumour number was assessed by counting the number of polyps that were protruding from the otherwise flat mucosa over the entire colon. All mice exposed to AOM/DSS displayed some tumour in the colon. However, remarkably, the 71 D6 agonistic antibody reduced the number of tumour masses by more than 50% (FIG. 4A). Notably, this reduction was statistically significant ($p<0.05$) compared to the vehicle alone arm both at 1 and 5 mg/kg, thus confirming the efficacy of the treatment even at the lower dose tested. On the contrary, the antagonistic anti-MET 74C8-OA antibody did not significantly reduce the number of tumours, thus implying that MET agonistic activity and not just MET binding is essential for inhibiting colon carcinogenesis in the presence of persistent inflammation. Colon images were analysed using Image J software (National Instututes of Health) and the volume of the polyps was calculated using the formula $V=\frac{3}{4}\pi(X/2)-(Y/2)^2$, where V is the volume of the polyp, and X and Y are the major and minor dimensions of the polyp section, respectively (in mm). As shown in FIG. 4B, 71D6 reduced not only the number but also the size of tumour masses in a dose-dependent manner (1 mg/kg 50% reduction; 5 mg/kg, 25% reduction) compared to the vehicle alone arm. Even more strikingly, 71 D6 was very effective in decreasing total tumour burden, reaching 77% reduction at the 1 mg/kg dose and 89% at the 5 mg/kg dose (FIG. 4C). Not less importantly, treatment with the antagonistic anti-MET 74C8-OA antibody did not affect any of the tumour parameters measured, i.e. mean polyp number, mean tumour volume and total tumour burden.

Following tissue processing and paraffin embedding, colon specimens were cut using a microtome and prepared for histological and immunohistochemical analysis. First, sections were stained with hematoxylin and eosin and examined by microscopy. This analysis confirmed that AOM/DSS treatment caused chronic inflammation of the colonic mucosa leading to the development of large malignant lesions (FIG. 5). Histological analysis of tumours revealed that all lesions represent high grade adenomas of the colonic epithelium (also known as in situ carcinoma of the colon). Strikingly, the 71 D6 antibody at both doses almost completely suppressed adenoma formation, maintaining a normal morphology of the mucosa, substantially indistinguishable from the control group. The antagonistic 74C8-OA antibody, on the contrary, did not affect AOM/DSS-induced tumour formation at all.

Next, we determined whether chronic colon inflammation resulted in fibrosis. To this end, colon sections were stained by various techniques specific for the detection of fibrotic tissue, including the Picro Sirius red method, which highlights collagen, and anti-alpha smooth muscle actin ($\alpha$-SMA) antibodies, which specifically stain myofibroblasts. These analysis revealed that repeated DSS administration caused the insurgence of massive fibrosis in colonic tissue. Collagen-rich fibrotic tissue is particularly evident where tumour masses are present (FIG. 6). Remarkably, colon sections derived from animals treated with both AOM-DSS and 71 D6 showed a significant lower collagen deposition and milder fibrosis at 1 mg/kg as well as at the higher dose without any evident difference between the two. Colon sections derived from 74C8-OA-treated animals displayed an extent of collagen deposition and fibrosis comparable to that of the vehicle alone arm. A similar pattern of the distribution was observed with $\alpha$-SMA staining, with higher presence of myofibroblasts in the vehicle alone control arm as well as in the 74C8-OA arm, compared to mice that received 71D6 at either doses (FIG. 7).

Colon sections were also stained for the expression of transforming growth factor beta (TGF-$\beta$). TGF-$\beta$ signalling has been demonstrated to be frequently deregulated in human cancers, including colorectal cancer (Massagué, Cell 134:251-230, 2008; Xu et al., Hum Mol Genet. 16 (SPEC): R14-R20, 2009). While in normal or premalignant cells it usually acts as a tumour suppressor, in advanced cancer it is frequently overexpressed and the growth inhibitory function switch to an oncogenic one thus promoting tumour cell proliferation and invasion (Nagaraj et al., Expert Opin Investig Drugs 19:77-91, 2010). Staining of colon sections with anti-TGF-$\beta$ antibodies revealed that TGF-$\beta$ expression is increased by the AOM-DSS treatment and particularly in tumour tissue (FIG. 8). Notably, treatment with the 71 D6 agonistic antibody restored TGF-$\beta$ levels comparable to those observed in control healthy mice both at 1 and at 5 mg/kg. In contrast, colon sections from mice treated with the 74C8-OA antagonistic antibody displayed a TGF-$\beta$ expression indistinguishable from that of the vehicle alone arm.

These data suggest that MET activation and not blockade is beneficial in chronic inflammatory pathologies of the intestine, and that administration of a MET-activating drug can both reduce the clinical signs of chronic colon inflammation (such as weight loss, diarrhoea, rectal bleeding, blood in stool, colon thickening, collagen deposition, myofibroblast proliferation and fibrosis) and suppress the development of chronic inflammation-induced colorectal cancer. We suggest that the 71D6 antibody or other similar MET agonistic antibodies may be used in the clinic to treat pathological conditions associated with chronic colon inflammation, including colitis-associated fibrosis and especially cancer.

Example 13: The 71 D6 MET Agonistic Antibody Inhibits DNA-Damaging Agent-Induced Colorectal Carcinogenesis The results obtained in the AOM/DSS model suggest that MET activation using an agonistic antibody dramatically reduces the risk of developing colorectal cancer, typically associated with chronic inflammation of the intestine. However, colorectal cancer may also arise from gene mutations in the epithelial cells of the colonic mucosa that accumulate during long periods of time. The particular anatomical site of these epithelial cells expose them to a number of agents introduced with the food or drink that may cause DNA mutations, particularly if food is contaminated with pollutants. Furthermore, pathological conditions of the intestine such as disbiosys or altered permeability can enhance the occurrence of gene mutations in the colonic mucosa.

In order to determine whether MET activation via an agonistic antibody can affect mutagenesis-promoted colorectal carcinogenesis, we tested the 71 D6 molecule in a the following setting. We injected 7 week-old female BALB/c mice (Charles River) with the colon-specific mutagen AOM at a dose of 5 mg/kg once a week for 6 weeks. Starting from day 1, mice were randomized into 2 arms of 21 mice each which received treatment with 71D6 (at a dose of 5 mg/kg) or vehicle only (PBS). Antibody was administered two times a week by i.p. injection. An additional, third control arm contained 7 mice that received no AOM or antibody and served as healthy control. Mice were sacrificed 8 weeks after the last AOM injection, i.e. 14 weeks after the experiment started. At autopsy, colons were collected and washed through. Explanted colons were measured using a ruler and weighed. Following measurements, colons were cut open longitudinally to expose tumour masses. Tissues were stained ex vivo with a 1% Alcian Blue solution in order to highlight tumour borders. Polyps were counted and photographed under a stereo-microscope. At the end of this procedure, colons were fixed in 4% paraformaldehyde, embedded in paraffin and processed for histological analysis.

In contrast to AOM/DSS, and consistent with the absence of inflammation, AOM alone did not affect colon length (FIG. 9A) or specific weight (FIG. 9B) compared to control mice. 71 D6 treatment also did not change significantly either parameter. However, AOM-induced mutagenesis did result in the development of colorectal cancer, although to a reduced extent compared to AOM/DSS in terms of both incidence (FIG. 10A) and number (FIG. 10B). This is consistent with the idea that chronic inflammation boosts tumour progression in many organs, including the intestine. Interestingly, treatment with the 71 D6 agonistic antibody significantly inhibited AOM-promoted cancer: in fact, both tumour incidence (FIG. 10A) and number (FIG. 10B) decreased by approximately 60% in the arm receiving 71 D6.

FIG. 11 shows two representative images of explanted colons for each arm. Colon samples were stained using a 1% Alcian Blue solution. The arrows indicate macroscopically evident tumour masses. Colon sections were then processed for histology. This analysis indicated that the polyps observed under the stereo-microscope are low grade adenomas, therefore less malignant than those observed in the AOM/DSS model.

Example 14: Reduction of Colonic Inflammation by MET Agonist Antibodies

We tested whether agonistic anti-MET antibodies could reduce intestinal inflammation in a mouse model, since intestinal (colorectal) inflammation is a major risk factor in developing colorectal cancer. To this end, we exposed 7 week-old female BALB/c mice (Charles River) to dextran sodium sulphate (DSS) in the drinking water for 10 days. On day 10, DSS treatment was interrupted and mice were put back on normal water. Starting from day 1, mice were randomized into 7 arms of 7 mice each which received treatment with 71G3, 71 D6, 71G2 (at a dose of 1 mg/kg or 5 mg/kg) or vehicle only (PBS). Antibodies were administered three times a week by i.p. injection. An additional, eighth control arm contained 7 mice that received no DSS or antibody and served as healthy control. Mice were sacrificed on day 12, i.e. 2 days after DSS administration was interrupted. At autopsy, colons were collected, washed through, and their length was determined using a ruler. Following measurement, colons were embedded in paraffin and processed for histological analysis.

During the whole course of the experiment, mouse weight was monitored on a regular basis, and the clinical symptoms of intestinal inflammation were assessed by determining faecal blood, rectal bleeding and stool consistency. Quantification was achieved using a standard scoring system used in pre-clinical models (Kim et al., J Vis Exp. 60, pii: 3678, 2012): each parameter scored from 0 (absence of the symptom) to 3 (maximal manifestation of the symptom). Scores relative to the single parameters were summed together to give rise to the Disease Activity Index (DAI) ranging from 0 to 9.

As shown in FIG. 12, exposure to DSS in the PBS arm caused a weight loss of up to 25%; the DAI increased to a score of 4 or higher; and the length of the colon was reduced by up to 40%. Remarkably, all antibodies analyzed reversed these effects in a dose-dependent fashion, displaying significant activity already at the lower dose tested. 71D6 was the most potent antibody: after a transient decline, it brought body weight back at normal values, comparable to those observed in the PBS group; it curbed the DAI increase, substantially inhibiting all the clinical symptoms; and it prevented colon shortage, limiting it to negligible variations.

Colon sections were stained with hematoxylin and eosin and examined by microscopy. As shown in FIG. 13, DSS administration caused profound damage to the colonic mucosa. The epithelial layer appeared eroded and infiltrated with lymphocytes. The colonic mucosa was disseminated with cryptic abscess sites and was heavily colonized by foamy macrophages, responsible for tissue destruction. Perivisceral lymph nodes appeared enlarged. The muciparous glands were characterized by atrophy and displayed marked mucinous depletion, which was substituted with inflammatory infiltrate including foamy macrophages, lymphocytes and neutrophils. Several ulcers were visibly invaded by granulocytic or macrophage exudate, leading to the total disappearance of the glandular component. Remarkably, mice treated with both DSS and agonistic anti-MET antibodies displayed much milder symptoms of degeneration and inflammation. Specifically, elements of acute inflammation were absent, including macrophages and granulocytes; the mucosa appeared only marginally injured, displaying sparse glandular distortion and rarefaction; mucin secretion was restored, and erosions and ulcers were completely absent. Although these protective effects were dose-dependent in all antibody groups, they were already evident at 1 mg/kg, indicating that the concentrations of antibodies reached with this dose are very close to saturation. In this model as well, the most effective antibody appeared to be 71D6, though all tested agonist antibodies were effective.

CONCLUSION

We conclude that treatment with an HGF-MET agonist (in this case a MET agonistic antibody) can be beneficial in both the treatment of colorectal cancer associated with chronic inflammation, and also in the inhibition of tumours arising from mutations in the colonic tissue. Agonist antibody 71 D6 has been demonstrated to be particularly effective in treating these conditions. Other MET agonist antibodies described herein (for example 71G3 and 71G2) also exhibit a potent ability to reduce intestinal inflammation comparable to 71D6 and will therefore provide similar therapeutic and preventative effects.

Moreover, the results herein demonstrate that MET agonists are more effective at treating (colorectal) cancer than the native MET ligand HGF. Yamaji et al. *Oncology Reports* 26: 335-341, 2011 (incorporated herein by reference) describe administering HGF to mice in similar models to those described herein. However, HGF is not as effective as MET agonists such as anti-MET agonist antibodies—for example, HGF only reduces tumour incidence in AOM-treated mice from 65% to about 30% (Yamaji et al, Table I), compared to MET agonist antibodies which reduce tumour incidence to less than 20% (FIG. 10).

We suggest that treatment with MET agonists, particularly MET agonist antibodies such as 71 D6, may be used in the clinic for reducing the development of colorectal tumours in those individuals predisposed to colorectal cancer, for example in patients affected by familial adenomatous polyposis (FAP; characterized by APC or MUTYH gene mutations) or by other genetic syndromes, as well as those predisposed to colorectal cancer as a result of inflammatory bowel conditions.

The invention claimed is:

1. A method of treating colorectal cancer comprising administering to a subject suffering therefrom a MET agonist;
   wherein the MET agonist is an anti-MET agonist antibody or antigen-binding fragment thereof comprising a VH CDR1 of sequence SEQ ID NO:30, a CDR2 of sequence SEQ ID NO:32, and a CDR3 of sequence SEQ ID NO:34, and a VL CDR1 of sequence SEQ ID NO:107, a CDR2 of sequence SEQ ID NO:109, and a CDR3 of sequence SEQ ID NO: 111, and
   wherein the subject has been diagnosed with colorectal inflammation prior to administration of the MET agonist.

2. The method of claim 1, wherein the cancer is colorectal cancer.

3. The method of claim 1, wherein the subject has been identified as at increased risk of colorectal cancer.

4. The method of claim 1, wherein the subject has inflammatory bowel disease, ulcerative colitis or Crohn's disease.

5. The method of claim 1, wherein the subject has a family history of familial adenomatous polyposis (FAP).

6. The method of claim 1, wherein the MET agonist is administered at a dose in the range from 0.1-10 mg/kg per dose.

7. The method according to claim 1, wherein the MET agonist is administered at least once per week.

8. The method according to claim 1, wherein the MET agonist is a full agonist of MET.

9. The method according to claim 1, wherein the anti-MET agonist antibody or antigen-binding fragment comprises a VH domain at least 90% identical to SEQ ID NO:163 and/or comprises a VL domain at least 90% identical to SEQ ID NO:164.

10. The method according to claim 9, wherein the anti-MET agonist antibody comprises a VH domain consisting of SEQ ID NO:163 and a VL consisting of SEQ ID NO:164.

11. The method according to claim 1, wherein the anti-MET agonist antibody is an IgG4 antibody.

12. The method according to claim 1, wherein the anti-MET agonist antibody or antigen-binding fragment thereof comprises a VH domain at least 95% identical to SEQ ID NO:163.

13. The method according to claim 1, wherein the anti-MET agonist antibody or antigen-binding fragment thereof comprises a VL domain at least 95% identical to SEQ ID NO:164.

14. A method of treating colorectal cancer in a subject, comprising administering to the subject an effective amount of anti-MET antibody which comprises a VH domain consisting of SEQ ID NO:163 and a VL consisting of SEQ ID NO:164, wherein the subject has been diagnosed with colorectal inflammation prior to administration of the MET agonist.

* * * * *